(12) United States Patent
McLoughlin et al.

(10) Patent No.: US 11,944,588 B2
(45) Date of Patent: Apr. 2, 2024

(54) DEVICES AND SYSTEMS FOR DELIVERY OF COMBINATION THERAPIES

(71) Applicant: Bristol-Myers Squibb Company, Princeton, NJ (US)

(72) Inventors: Martin John McLoughlin, Hillsborough, NJ (US); Stephen Lawrence Zieminski, East Brunswick, NJ (US); Chester Larrow, Baltimore, MD (US); Mariano Mumpower, Baltimore, MD (US)

(73) Assignee: Bristol-Myers Squibb Company, Princeton, NJ (US)

( * ) Notice: Subject to any disclaimer, the term of this patent is extended or adjusted under 35 U.S.C. 154(b) by 515 days.

(21) Appl. No.: 17/047,126

(22) PCT Filed: May 10, 2019

(86) PCT No.: PCT/US2019/031727
§ 371 (c)(1),
(2) Date: Oct. 13, 2020

(87) PCT Pub. No.: WO2019/217820
PCT Pub. Date: Nov. 14, 2019

(65) Prior Publication Data
US 2022/0023531 A1    Jan. 27, 2022

Related U.S. Application Data

(60) Provisional application No. 62/670,266, filed on May 11, 2018.

(51) Int. Cl.
*A61M 5/14*   (2006.01)
*A61J 1/20*   (2006.01)
*A61M 5/142*  (2006.01)

(52) U.S. Cl.
CPC .............. *A61J 1/2089* (2013.01); *A61J 1/201* (2015.05); *A61J 1/2058* (2015.05); *A61J 1/2075* (2015.05);
(Continued)

(58) Field of Classification Search
CPC .............. A61M 5/1408; A61M 5/1409; A61M 5/16827; A61J 1/16; A61J 1/20; A61J 1/2089; A61J 1/2096
See application file for complete search history.

(56) References Cited

U.S. PATENT DOCUMENTS

| 4,085,782 A | 4/1978 | Carlson |
| 5,037,390 A | 8/1991 | Raines et al. |

(Continued)

FOREIGN PATENT DOCUMENTS

| CN | 101472641 A | 7/2009 |
| CN | 102652843 A | 9/2012 |

(Continued)

OTHER PUBLICATIONS

Blumenthal machine translation (Year: 2005).*
(Continued)

*Primary Examiner* — Laura A Bouchelle
(74) *Attorney, Agent, or Firm* — Budzyn IP Law, LLC

(57) ABSTRACT

In one aspect, the subject invention is directed to a method of preparing a combinatorial drug delivery device based on a predetermined selection of drug components. The method includes: preparing a plurality of containers, each accommodating one of the selected drug components; coupling the containers to a common outlet so that the drug components may be extracted from the containers and dispensed through the common outlet; and, applying negative pressure to extract the drug components from the containers and urge the drug components towards the common outlet.

23 Claims, 59 Drawing Sheets

Wearable, modular, liquid, partially reusable

(52) U.S. Cl.
CPC ........ *A61M 5/1407* (2013.01); *A61M 5/1408* (2013.01); *A61M 5/1409* (2013.01); *A61M 5/1413* (2013.01); *A61M 5/14248* (2013.01); *A61J 1/2068* (2015.05)

(56) References Cited

U.S. PATENT DOCUMENTS

| | | | |
|---|---|---|---|
| 5,569,181 A * | 10/1996 | Heilman | A61M 5/007 604/30 |
| 6,699,230 B2 * | 3/2004 | Jaafar | A61M 5/44 604/508 |
| 8,114,064 B2 * | 2/2012 | Alferness | A61M 5/1452 604/890.1 |
| 9,173,991 B2 * | 11/2015 | Yodfat | A61M 5/14228 |
| 9,925,333 B2 | 3/2018 | Hooven et al. | |
| 10,569,014 B2 | 2/2020 | Hanson et al. | |
| 2002/0004643 A1 | 1/2002 | Carmel et al. | |
| 2002/0007671 A1 | 1/2002 | Lavi et al. | |
| 2011/0004143 A1 * | 1/2011 | Beiriger | A61M 1/3462 604/6.11 |
| 2013/0253430 A1 * | 9/2013 | Kouyoumjian | A61M 5/16827 604/151 |
| 2013/0269825 A1 | 10/2013 | Osborn et al. | |
| 2013/0274656 A1 | 10/2013 | Dehan et al. | |
| 2015/0257974 A1 | 9/2015 | Demers et al. | |
| 2017/0020784 A1 | 1/2017 | Schweiss et al. | |

FOREIGN PATENT DOCUMENTS

| | | | |
|---|---|---|---|
| DE | 102004010062 B3 * | 9/2005 | .......... A61M 5/1408 |
| JP | 2016524513 A | 8/2016 | |
| JP | 2018507064 A | 3/2018 | |
| WO | 2007107406 A2 | 9/2007 | |
| WO | 2012072555 A1 | 6/2012 | |
| WO | 2012092564 A2 | 7/2012 | |
| WO | 2016205687 A1 | 12/2016 | |

OTHER PUBLICATIONS

CInternational Search Report and Written Opinion of the International Searching Authority from PCT International Application No. PCT/US2019/031727, dated Jul. 18, 2019.

Search Report from Chinese Application No. 2019800318744 dated Dec. 12, 2023.

* cited by examiner

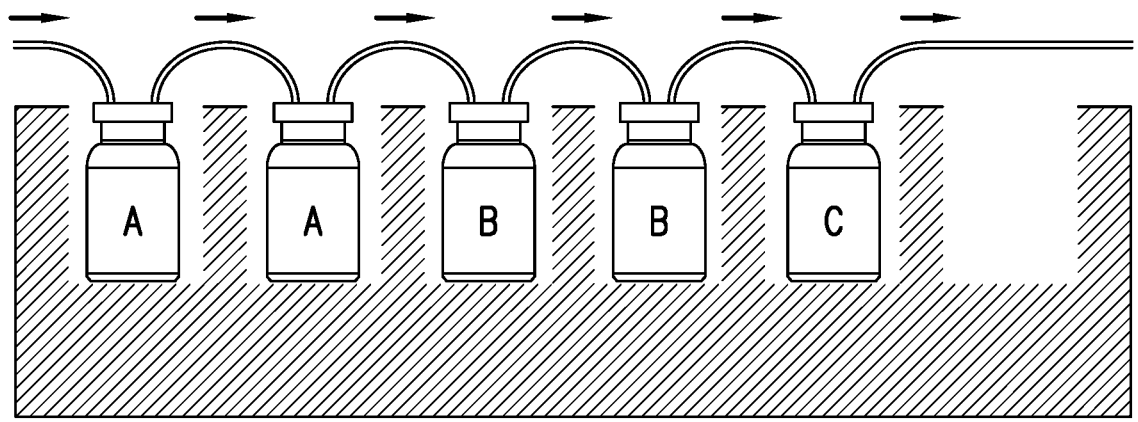
FIG.7A
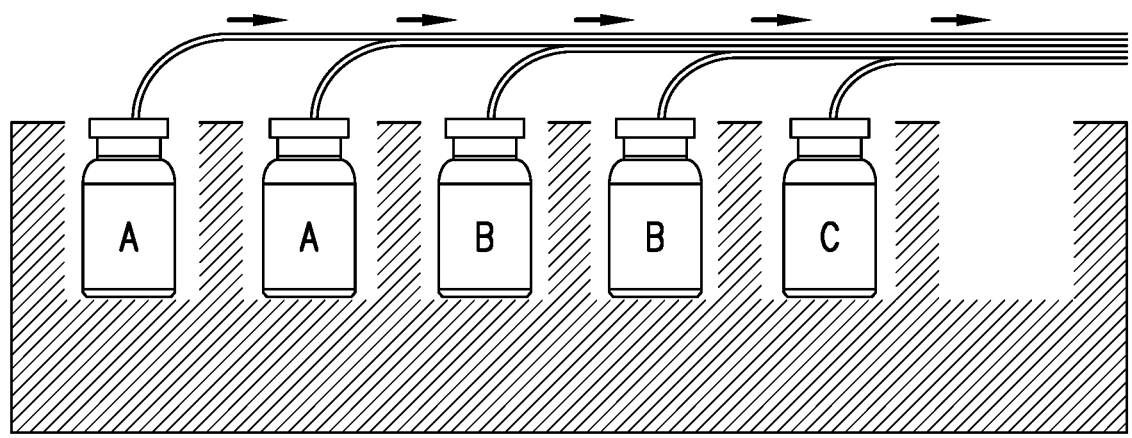
FIG.7A2

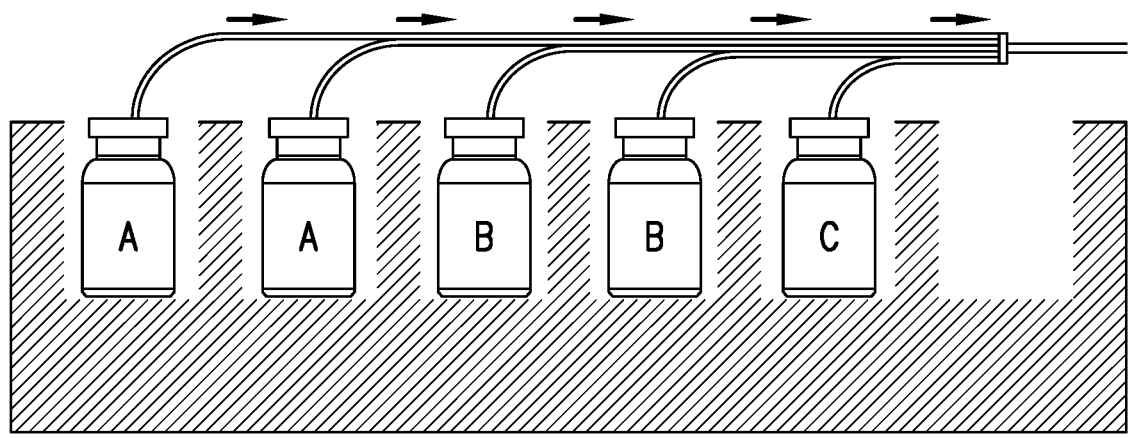
FIG.7A3
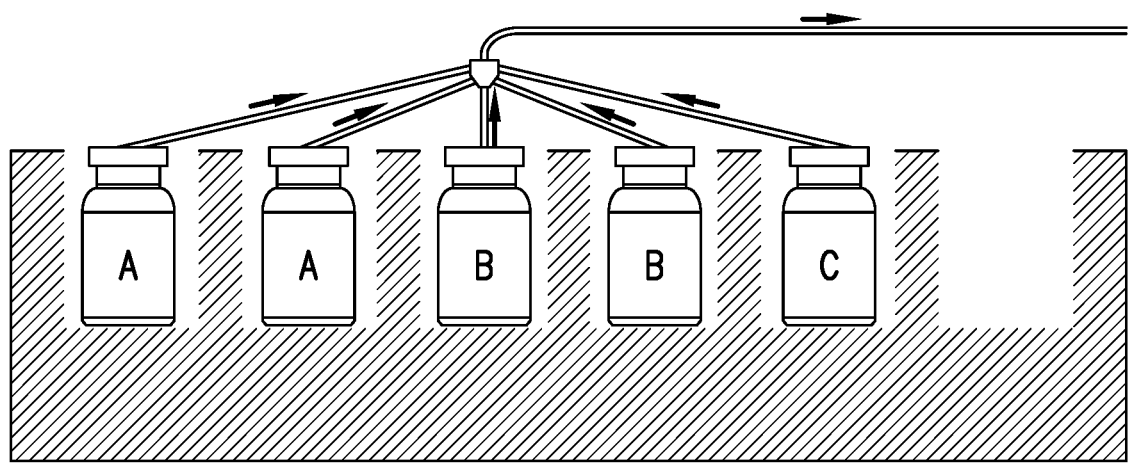
FIG.7A4

Wearable, monolithic, powder w/reconstitution, fully disposable

Wearable, monolithic, liquid, fully disposable

Wearable, modular, powder w/reconstitution, reusable drive system

Wearable, modular, liquid, partially reusable

Belt, powder w/ reconstitution, fully disposable

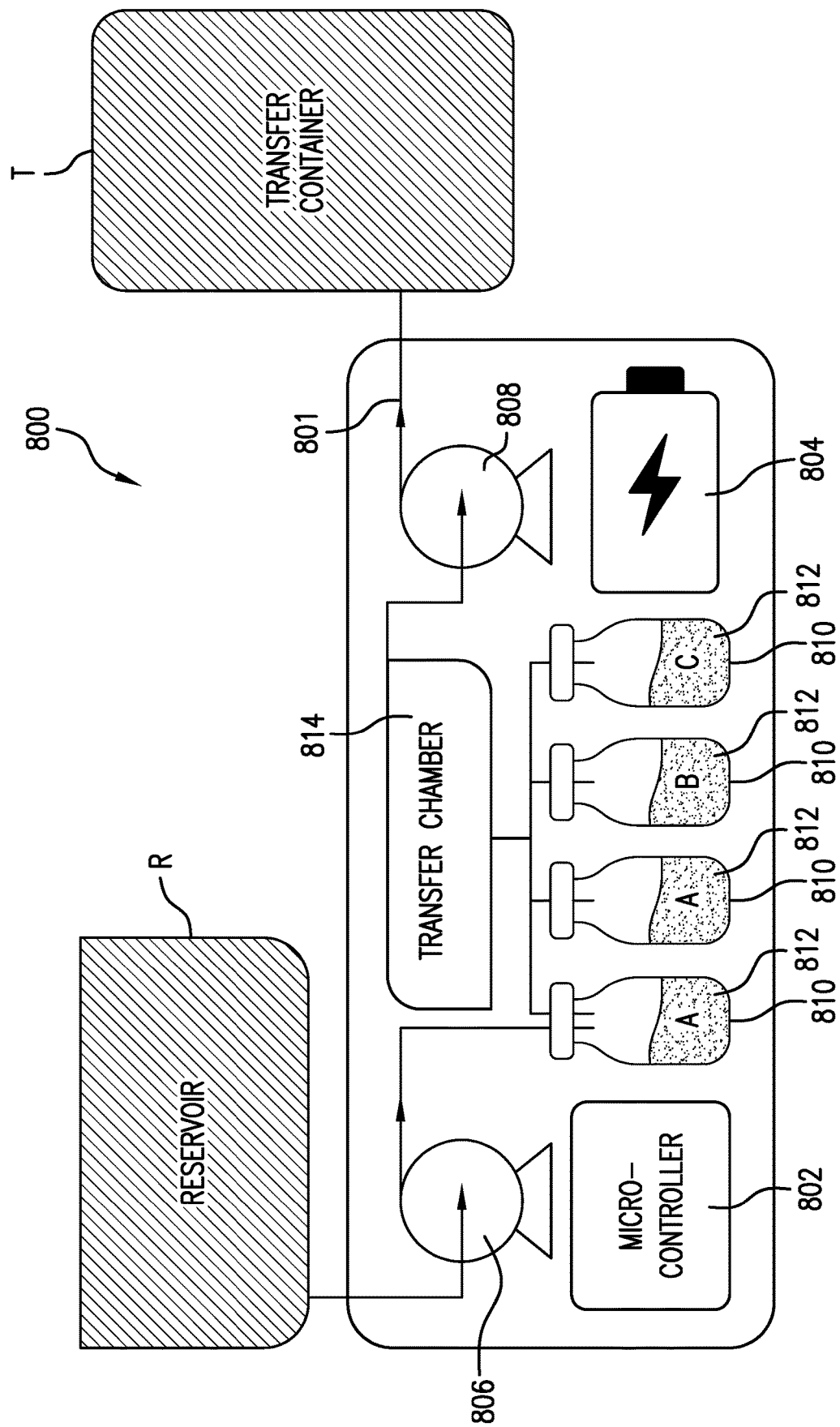

Transfer device, liquid vials, fully disposable

DEVICES AND SYSTEMS FOR DELIVERY OF COMBINATION THERAPIES

FIELD OF THE INVENTION

The field of the invention is the delivery of combination therapies comprised of two or more drugs for the beneficial treatment of patients suffering from any of a wide range of conditions. More particularly the invention is concerned with the parenteral delivery of said combinations of drugs, especially via the intravenous, subcutaneous and intra-tumoral routes of administration, though application of the invention is not limited to these cases.

BACKGROUND OF THE INVENTION

It is well known to the person skilled in the art that the treatment of a particular disease state may be improved by the combined administration of more than one drug. This may be because each drug in the combination treats a different symptom of, or risk factor for, the disease or because each drug has specificity for a molecular target involved in the etiology of the disease. In many combination therapies, the drugs have synergistic interaction where the beneficial effect from use of the drugs in combination is greater than the additive effects that would be expected from the use of each drug singly. In some cases, the synergistic effect may arise from the simple presence of each drug systemically and contemporaneously, whereas in other cases the synergy may rely on the co-administration of the drugs in a specific manner for example where each drug in the combination binds a specific molecular target in a biochemical pathway. An example of combination treatments is the daily oral co-administration of primary prevention regimens for the treatment of cardiovascular disease (CVD) comprising a cholesterol lowering agent such as a member of the statin class of drugs, an antihypertensive such as an angiotensin-converting enzyme (ACE) inhibitor and an anticoagulant such as aspirin or warfarin. This regimen is typically administered in oral solid form with each drug administered as a separate tablet. Because each drug is administered separately, the physician can vary the quantity of each drug prescribed to the specific needs of the individual patient. In multifactorial diseases such as CVD where the various risk factors are to some degree independent, the ability to vary one drug independently of another provides the physician the flexibility to differentially treat the risk factors and manage side effects on a case-by-case basis. For example, a patient who presents with hypertension but only slightly elevated levels of cholesterol could in principle be treated with a smaller dose of statin and a higher dose of ACE inhibitor. Drug products, which contain only one active ingredient, are sometimes referred to as a single-agent therapy or monotherapy.

Another example of oral combination therapies is provided by the anti-retroviral therapies (ART) used in the treatment of HIV and AIDS. Within this field there are numerous examples of tablets which are comprised of two (e.g., Combivir) or three drugs (e.g., Trizivir). When combined together in the same tablet the drugs are present in fixed ratios. This limits the ability of the dose of one drug to be varied independently of the other. Such combinations where ratios are fixed are variously known as fixed ratio combinations (FRC), fixed dose combinations (FDC) or fixed dose ratio combinations (FDRC). For the purposes of the present disclosure, the term FRC shall be used. The decision to co-formulate the drugs in a FRC may be taken for reasons of efficacy (e.g. the particular ratio of drugs has been shown to be particularly beneficial), safety (the FRC reduces the risk of side effects, overdose, underdose and medication errors) or convenience (to reduce the pill burden of the patient).

Another example of a FRC is the combination of a bronchodilator and corticosteroid in an inhalator device for the treatment of asthma or chronic obstructive pulmonary disease (COPD). The device in this case may be a metered dose inhaler or a dry powder inhaler. Examples are Advair (GlaxoSmithKline or "GSK"), Symbicort (Astrazeneca). Trelegy Ellipta (GSK) is an example of a FRC combination therapy for inhalation comprised of three drugs.

FRCs may be created in different states of aggregation. At one extreme, there are FRCs which are intimately mixed at the molecular scale, e.g. two drugs in mutual solution with each other. Such FRCs are effectively inseparable by anything other than advanced and laborious chemical methods. In the case of combination tablets, the drugs are typically physically mixed together in powder or granular form prior to compression. In the case of dry powder inhalers the drugs may be intimately mixed powders with particle sizes in the respirable range, blended with a coarse carrier particle. Alternatively the drugs may be kept separate until inhaled e.g. as in the case of the Breo Ellipta FRC device in which the two drugs are formulated into separate blister strips. An advantage of this arrangement compared to FRCs of the co-formulated type represented by the Advair Diskus device is that configuring the device for different drugs or strengths is transformed from a complex reformulation to a simple assembly process change. In these cases, the drugs are in principle physically separable without chemical processes, however, for all practical purposes they are inseparable. For the purposes of exposition of the present invention, inseparable FRCs of the solution or powder blend types shall be called co-formulated FRCs. The other separable types shall be called co-packaged FRCs.

In some examples of FRCs such as that exemplified by the Omeclamox Pak for the treatment of *H. pylori* infection, the drugs are formulated individually and co-packaged together into a single product. The correct administration of the FRC in this case relies on the user to follow the instructions and take the drugs correctly.

Recent progress in the field of immuno-oncology has led to the development of new biotechnology derived agents, which have particular efficacy in the treatment of certain tumors and other cancers. These agents are typically derived from immunoglobulin antibodies and are therefore proteins and as such typically have no oral bioavailability and must be administered parenterally. Most typically, said biotechnology drugs are administered via intravenous infusion at a hospital or infusion clinic. The drugs are typically supplied in liquid or powder form in vials and are prepared (compounded) for administration in the pharmacy before delivery to the patient for infusion. This requires the patient to attend the hospital or clinic and for some patients may require travel over considerable distances on a frequent basis.

Recent research has shown that the treatment of tumors and other cancers may be beneficially enhanced through the co-administration of two or more drugs, one or more of which may be such biologic agents. For example, considerable success in outcomes has been demonstrated by the inhibition of the PD-1 pathway in certain tumors and other cancers. In certain cases, the two or more agents may have no efficacy individually and rely on their synergistic interaction for their effect. These considerations have led to the development of fixed ratio combinations of two or more biologic agents. Such biologic FRCs are typically co-formulated in liquid form and provided in a vial for compounding for IV infusion. The drugs in such FRCs exist in mutual solution. Provision of the biologic agents in a FRC has several advantages compared to provision as single agents. These include convenience for the patient and pharmacy and reduction in the risk of medication errors that may occur in the pharmacy when two or more single agents are to be combined. There may also be safety and efficacy reasons that make provision as a FRC advantageous. For example, efficacy may rely on contemporaneous delivery of both agents which is guaranteed with such a FRC. Also, as potent immuno-modulators it may be important for safety to ensure that the drugs are provided in a very specific ratio.

Drawbacks of the provision of biologic agents as FRCs include the concomitant complexity that derives from the co-formulation of multiple agents. For example, the mutual solubility of the various agents may make the formulation of a stable liquid formulation difficult to the extent that it may not be achievable at all, or may result in instability and a restricted shelf life. The phase equilibria of the FRC solutions becomes increasingly complex as the number of drugs increases which may require excipients for modification of stability.

The multiple agents may also interact chemically with each other with deleterious effects. For example, it is known to the person skilled in the art that biologic agents based on immunoglobulins can chemically bind as dimers and higher oligomers which may render the active moiety pharmacologically inactive or may introduce toxicity or immunogenicity issues. When multiple agents are present heterodimers and higher oligomers of different agents may form with similar concomitant reductions in activity or increased toxicity or immunogenicity. The more agents that are present then the more heterogeneous species which may be present. This situation brings analytical complexity with the need to develop analytical techniques, which can resolve and identify such species in low concentrations. In addition, because of the potential for unforeseen impact on safety and efficacy the combination itself must be subject to long-term stability studies. Consequently, the investment in time and effort for the development of such FRCs is substantial and will likely be a significant barrier to the development of higher order combinations such as triplet and higher combinations.

Also, as in the aforementioned cases of oral and pulmonary delivery, provision of the agents as a FRC results in a loss of flexibility in dosing of the individual agents.

In certain circumstances, this flexibility must be retained for therapeutic reasons. For example, in some combinations one or more of the agents may require dosing in proportion to the patient's body weight or some other physiological measure. In such cases the ability to vary the dose of said agent independently of the others must be retained which may preclude the use of a FRC including that agent.

Another example is provided by the emergence of personalized medicine in which the treatment regimen is determined at the individual patient level through the use of biomarker assays. In this therapeutic scenario, the patient is tested for biomarkers, which have been shown to have diagnostic power for a specific condition, the results of which tests are subsequently used to design the treatment regimen for that individual patient. Implicit in this is a need for the flexibility to vary the dose of one or more agents independently of the others, which by definition cannot be achieved in a FRC.

Conventional pharmacy practice to vary or titrate the dose of a biologic agent is to draw only the required quantity from its container based on the results of the physiological calculation. Because biologic agents are sterile products, once container closure integrity is breached, the product must be used immediately or discarded. Therefore, any product remaining in the container after dose titration must be discarded. Given the very high cost of biologic agents, the financial impact of waste is significant.

There are also associated complexities in the manufacture and supply of FRCs of biologic agents. The compounding and formulation of biotechnology-derived agents is already extremely complex and their combination into FRCs makes manufacturing more complex still. Biotechnology derived products also typically have a very high cost of goods and are perishable, necessitating careful storage, usually at low temperature to preserve their integrity. The additional steps to create FRCs therefore increase the required investment in capital equipment and storage facilities. The number of single keeping units (SKUs) in the supply chain is increased with the addition of each FRC and work-in-progress and finished goods inventories are also increased which for very high value products comes at considerable cost. Avoidance of waste in manufacture is paramount also for the same reason.

The success of biologic agents, particularly immuno-oncology agents in the treatment of cancer, has the potential to transform the field of oncology such that a future state where the treatment of cancer is more typical of the treatment of a chronic disease is foreseeable. A consequence of this success is the financial burden on the healthcare system of the provision of highly effective, but intrinsically expensive biotechnology products.

These emerging trends in the treatment of cancer and other diseases treated by biologic drugs have indicated a need for more patient friendly drug delivery technologies and routes of administration.

For example, whereas it is tolerable for patients to undergo the expense and disruption to their daily lives from an acute course of therapy for which they have to travel significant distances for an otherwise fatal condition, this may be intolerable for a chronic treatment that may last years or decades.

In addition, there is a desire to reduce the costs of treatment for these intrinsically expensive agents by reducing the supply chain complexity, the need for infusion at clinics with complex pharmacy procedures and so on. Such cost reductions when realized will improve access to such therapies.

In summary, the benefits of formulating biologic agents as FRCs come at the cost of reduced flexibility and increased formulation, analytical and manufacturing complexity which may in some cases be prohibitive to the development of combinations which are otherwise promising candidates for new therapies.

One particular barrier to improved convenience and reduction in cost of treatment with biologic agents is the reliance on the intra-venous route-of-administration, which requires the patient to attend a hospital or clinic or be visited by a nurse or other healthcare practitioner. In contrast, the subcutaneous route-of-administration is procedurally simpler, and carries less risk and can therefore permit administration by laypersons including self-administration by the patient themselves. Within intra-venous administration practices, there remains scope for new technologies to simplify pharmacy procedures, reduce or eliminate waste and reduce the scope for medication errors.

New technologies are therefore required which preserve the benefits of FRCS whilst addressing their drawbacks and enabling greater patient convenience, flexibility in dosing and reductions in waste and the overall costs of treatment.

SUMMARY OF THE INVENTION

In one aspect, the subject invention is directed to a method of preparing a combinatorial drug delivery device based on a predetermined selection of drug components. The method includes: preparing a plurality of containers, each accommodating one of the selected drug components; coupling the containers to a common outlet so that the drug components may be extracted from the containers and dispensed through the common outlet; and, applying negative pressure to extract the drug components from the containers and urge the drug components towards the common outlet.

In a further aspect, the subject invention is directed to a combinatorial drug delivery device for delivering a drug combination based on a predetermined selection of drug components. The device includes: a plurality of containers, each accommodating one of the selected drug components; a body having a common outlet, wherein the containers are configured to couple to the body so that the drug components may be extracted from the containers and dispensed through the common outlet, the containers being accessible externally of the body; and, a source of negative pressure configured to extract the drug components from the containers and urge the drug components towards the common outlet.

In yet a further aspect, the subject invention is directed to a combinatorial drug delivery device for delivering a drug combination based on a predetermined selection of drug components. The device includes: a plurality of containers, each accommodating one of the selected drug components; a plurality of housings, each formed to accommodate one of the containers, wherein each of the housings includes a spike for accessing the drug component of the container located in the associated housing and a fluid path for the drug component; a common outlet; and, a source of negative pressure configured to extract the drug components from the containers and urge the drug components towards the common outlet.

These and other features of the subject invention will be better understood through a study of the following detailed description and accompanying drawings.

BRIEF DESCRIPTION OF THE DRAWINGS

FIG. 5b is an illustration of the two-dimensional composition space for drugs A, B of FIG. 5a where the lattice points have larger area due to less precision of the dispensing mechanism compared to the device of FIG. 5a.

FIGS. 7a, 7a2, 7a3, and 7a4 are schematics of a device comprised of six (6) nests which can be vacant or occupied interchangeably by vials of drugs A, B, C.

FIGS. 21, 21b, 21c, 21d, 21e and 21f are schematics of a device comprising four nests for receipt of powdered drugs A, B, C, a mixing chamber, an external diluent reservoir and transfer container, configured for the reconstitution of the drugs A, B, C using the diluent and subsequent transfer of the final composition to the transfer container ready for further transfer to another reservoir e.g., an intravenous infusion bag or other administration device for administration to the patient.

DETAILED DESCRIPTION OF THE INVENTION

The purpose of the present invention is to address the aforementioned issues arising from the delivery of combinations of biologic agents including the provision of greater flexibility and convenience whilst preserving the benefits of FRCs such as the prevention of medication errors and convenience and simplicity for the end user.

The present invention in all its various embodiments employs the principles of combinatorial theory to enable the flexible combination of biologic agents in a manner that maximizes patient convenience and treatment flexibility, whilst minimizing waste and complexity for the end user.

Combinatorics is that branch of mathematics, which is at least in part concerned with enumerating the ways in which discrete objects can be arranged and selected. Applied to the problem of drug combinations, combinatorics is concerned with analyzing and enumerating the number of ways that drugs may be combined to create a specific combination, or the calculation of the compositions that can be achieved from a given set of drug masses (strengths) and quantities where the permitted arrangements of the discrete objects is given. The results of such calculations can be used to design devices to provide an optimal balance of flexibility and simplicity for a particular therapeutic situation. The discrete objects of concern are the smallest available individual dosage unit. With oral solids, it is typical to think of the lowest strength tablet available as the discrete object of concern. In contrast, in the case of biologic agents which are typically supplied in liquid form and may be further diluted for intra-venous administration and may be titrated on the basis of patient weight for example, it is typical to think of the product as infinitely divisible.

It should be noted that when the formation of a dose is made from indivisible unit doses, e.g. of discrete tablets, there is no waste. In contrast, when vials are titrated, the unused remainder must be discarded and is wasted. One aspect of the present invention is the construction of doses and combinations of biologic agents from small, integral unit doses, which minimizes waste by analogy to the situation with tablets, notwithstanding the inevitable small losses that result from incomplete emptying of containers. It is a feature of the present invention therefore that the small integral dosage units from which combinations are assembled are atomic in the sense that they cannot be further subdivided.

Figure 1:
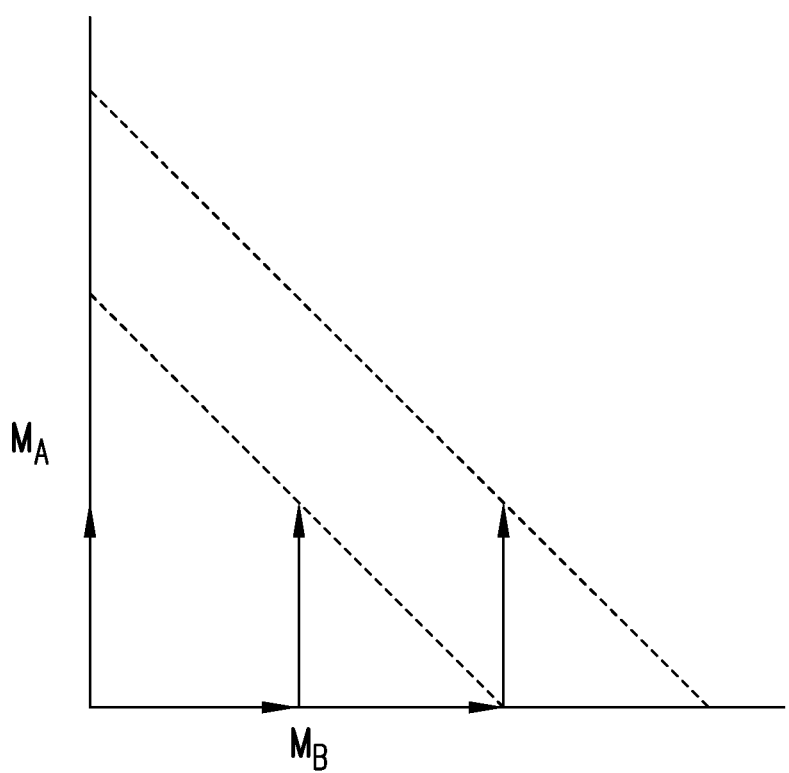
FIG. 1 is a schematic of a two-dimensional binary composition space for drugs A and B with basis vectors, resultant compositions and simplex lines shown.

The combinatorial principle is concerned only with the combinations of masses of each component of a combination and is applicable irrespective of the particular dosage form or container type used. It can therefore apply equally to solutions or solids either individually or in combination. In the combinatorial model, the mass of each component drug in the combination is represented as a dimension in an abstract rectilinear vector space. Because points in this space represent compositions it shall be referred to as composition space. The composition space for a two-drug (binary) combination requires two axes and can be represented as two mutually orthogonal axes in the plane, which is the usual Cartesian coordinate system [FIG. 1]. If the two drugs are called A and B respectively, then the composition space is known as the A-B system or the binary system A-B.

When the masses (strengths) of the smallest individual unit dose of each drug are defined, these can be represented as fixed length vectors collinear with the axes. The set of such vectors for each component of the combination is known as a basis or basis set of the composition space. Once the basis is defined all compositions of the two agents that can be reached (accessible compositions) are completely defined by linear combinations of the basis vectors. Geometrically this is simple vector addition and it follows from the physical principle of conservation of mass. When only discrete combinations of whole unit doses are permitted, the vectors are of fixed length and direction and the accessible compositions (the available combinations) form a rectangular array or lattice of points [FIG. 2A]. In general, the masses of the unit doses of the respective drugs may be different such that their respective vectors have different lengths. In the case where the vectors are of the same length then the resulting lattice is a square grid, otherwise it is rectangular. From the principle of conservation of mass, the component masses $M_A$, $M_B$ of components A and B respectively are subject to the constraint $$M_A + M_B = M_{Tot}$$

where $M_{Tot}$ is the total mass of the composition.

This is the equation for a family of lines that intersect both axes at the same distance from the origin, making a 45 degree angle with the axes. Each accessible composition lies on one of these lines [FIG. 2A].

The segment of such lines which lies in the positive quadrant of the space is called a simplex of the binary system. The simplex is defined mathematically as the simplest geometric figure with dimension one less than its parent space. Since the plane of the binary composition space has dimension two the simplex of the space has dimension one and is therefore a line segment. Compositions which lie on the same simplex all have the same total drug mass (total strength). Mass fractions, usually represented by the symbol X, are composition ratios which are sometimes more convenient to use when describing compositions than actual masses and can be calculated by dividing the mass of a single component in a combination by the total mass.

Therefore, in the binary system A-B, if $M_A$ is the mass of drug A and $M_B$ is the mass of drug B, then the mass fraction $X_A$ of A is given by $$X_A = \frac{M_A}{M_A + M_B}$$

and the mass fraction $X_B$ of drug B is given by:

$$X_B = \frac{M_B}{M_A + M_B}$$

Thus, defined mass fractions obey the identity $$X_A + X_B = 1$$

Mass fractions can be considered as a normalization of the masses such that all compositions with the same mass fractions have the same ratio of components irrespective of total mass. This allows compositions of different masses to be plotted on the same simplex diagram.

Figure 2A:
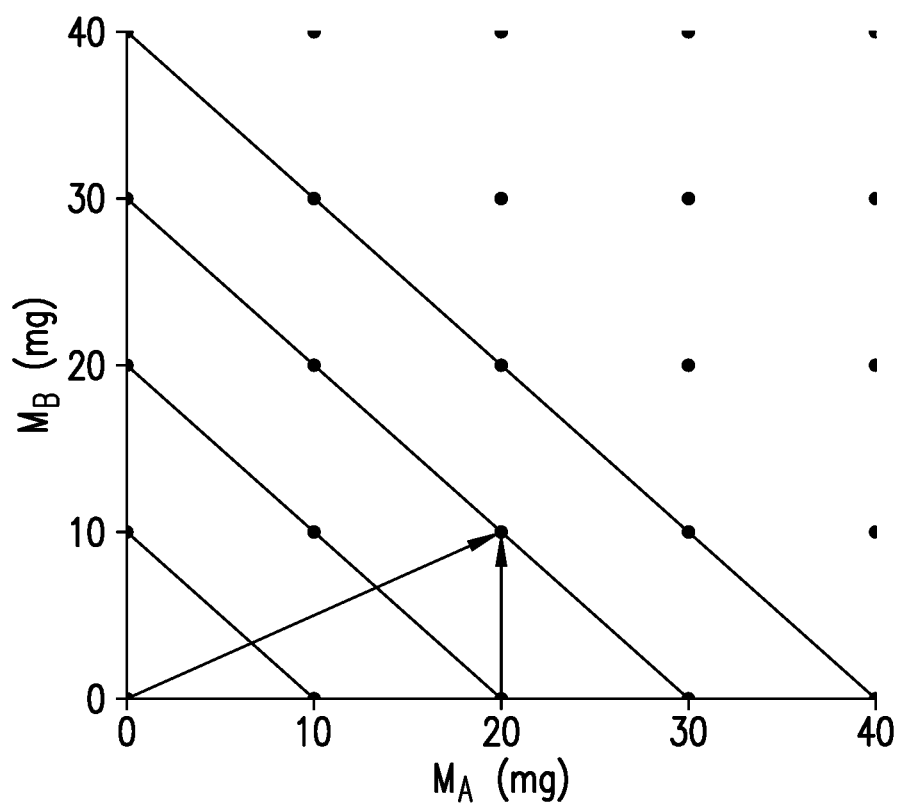
FIG. 2a is an illustration of a two-dimensional binary composition space for drugs A and B where the unit strength of the vials is 10 mg. The composition lattice and a single resultant composition formed from 2×10 mg A and 1×10 mg are shown.
Figure 2B:
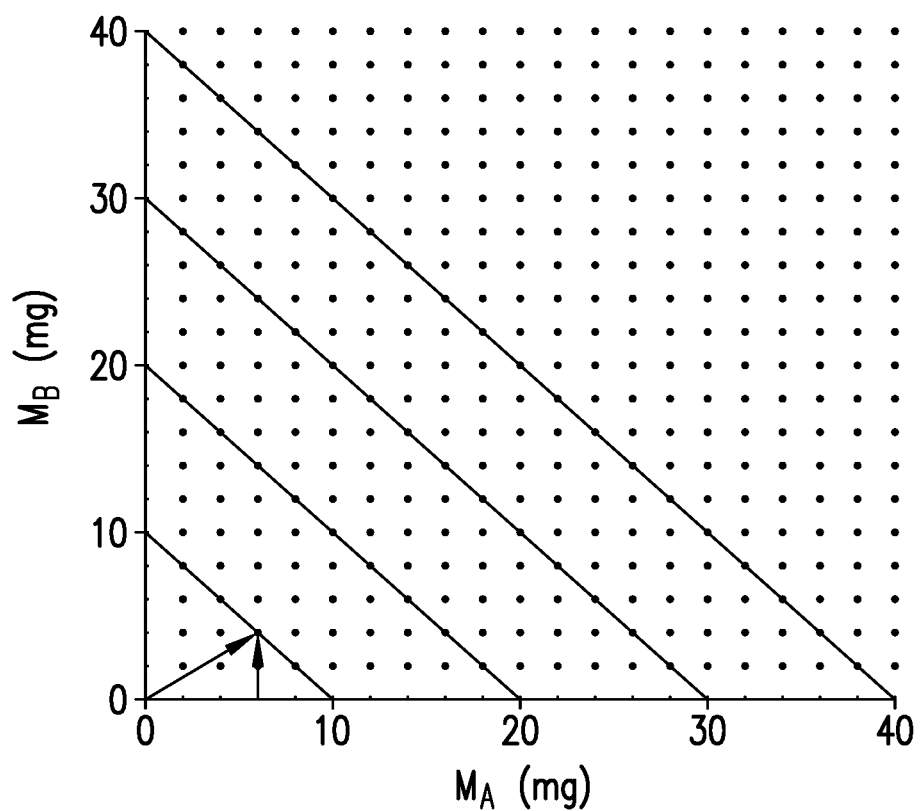
FIG. 2b is an illustration of a two-dimensional composition binary space for drugs A and B where the unit strength of the vials is 2 mg illustrating the increased density of lattice points compared to the situation in 2b. A single resultant composition formed from 2×2 mg A and 3×2 mg B is shown.

If the discrete unit doses are subdivided such that they become progressively smaller, the mass vectors become progressively shorter and the lattice points progressively closer together. FIGS. 2A and 2B show lattices of different density for the A-B system. In the limit the vectors become infinitesimally small and the lattice becomes infinitely dense. The set of accessible compositions is then equal to the set of all points in the space. For the purposes of describing the present invention, the converse of a dense lattice shall be called a sparse lattice and a lattice with a lower density of points than another is more sparse. Physically this represents the case of infinitely variable doses or infinite precision in dose titration. This situation can be represented by vectors where only direction is fixed such that their lengths may vary continuously. In this scenario, every point on the simplex line segment can be reached by a linear combination of basis vectors such that the simplex is the locus of all possible composition vectors. Conversely this can be thought of as the simplex line being complete with no gaps and there being an infinite family of zero spaced simplex lines. However, accessibility of a composition on the simplex is not a sufficient condition for the composition to be realized in practice. For example, extreme ratios of drugs e.g. where $M_A \gg M_B$ may require large volumes or high dilutions, making them unachievable practically. Mathematically this situation is described by saying that the resultant vectors of a series of compositions which are progressively richer in one component approach the axis of that component asymptotically.

This principle can be readily extended to any number of components such that composition spaces may have an infinity of dimensions however there are of course practical limits to how many drugs can be combined. For exposition of the principle and the present invention, discussion will be limited to no more than four component drugs. Three drug systems are called ternary systems, four drug systems are called quaternary systems.

For the ternary case consider the system A-B-C. The composition space A-B-C can be represented by three mutually orthogonal axes equivalent to the regular 3D Cartesian spatial coordinate system. Linear combinations of the fixed length basis vectors in this case form a three dimensional rectangular lattice. In the case where the vectors have the same length then the lattice is cubic.

Figure 3A:
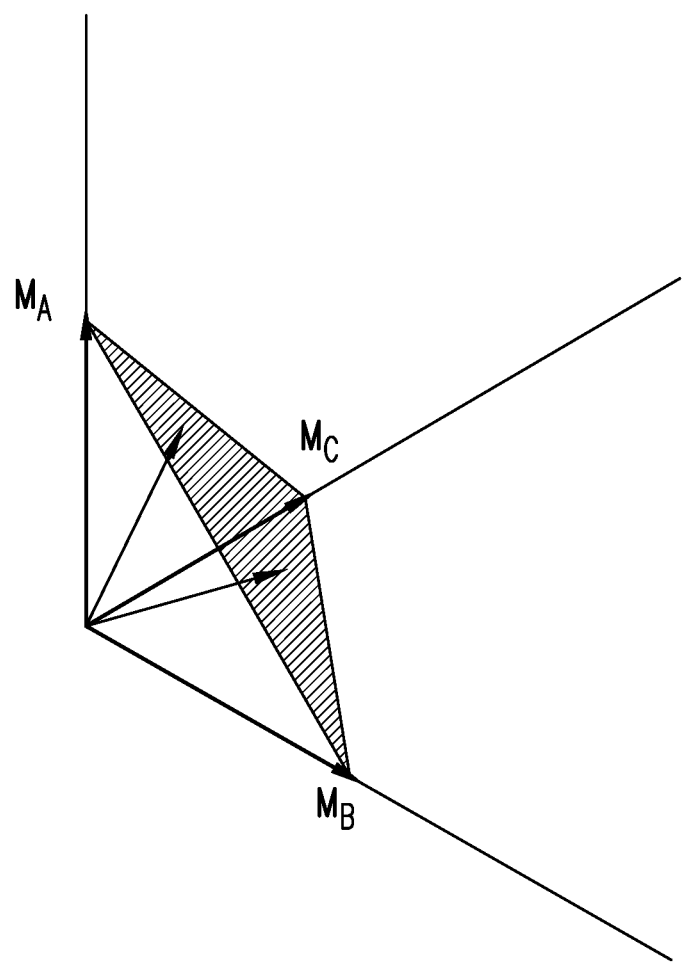
FIG. 3a is a two-dimensional projection of a three-dimensional ternary composition space illustrating basis and resultant vectors and the simplex triangle.
Figure 3B:
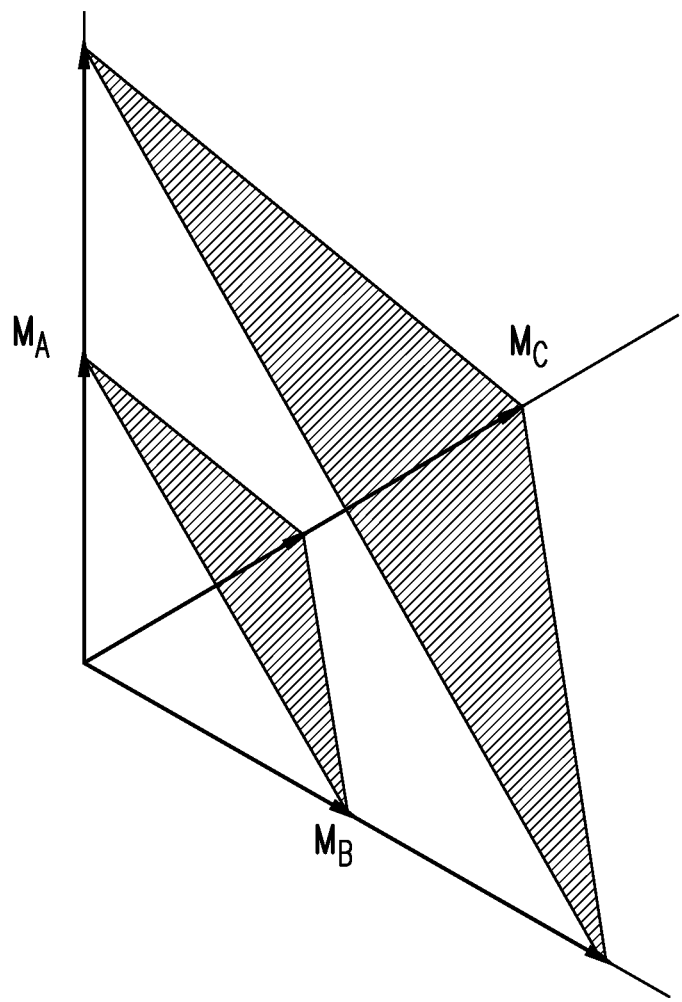
FIG. 3b is a two-dimensional projection of the three-dimensional ternary composition space of FIG. 3a showing the family of parallel simplex triangles.
Figure 3C:
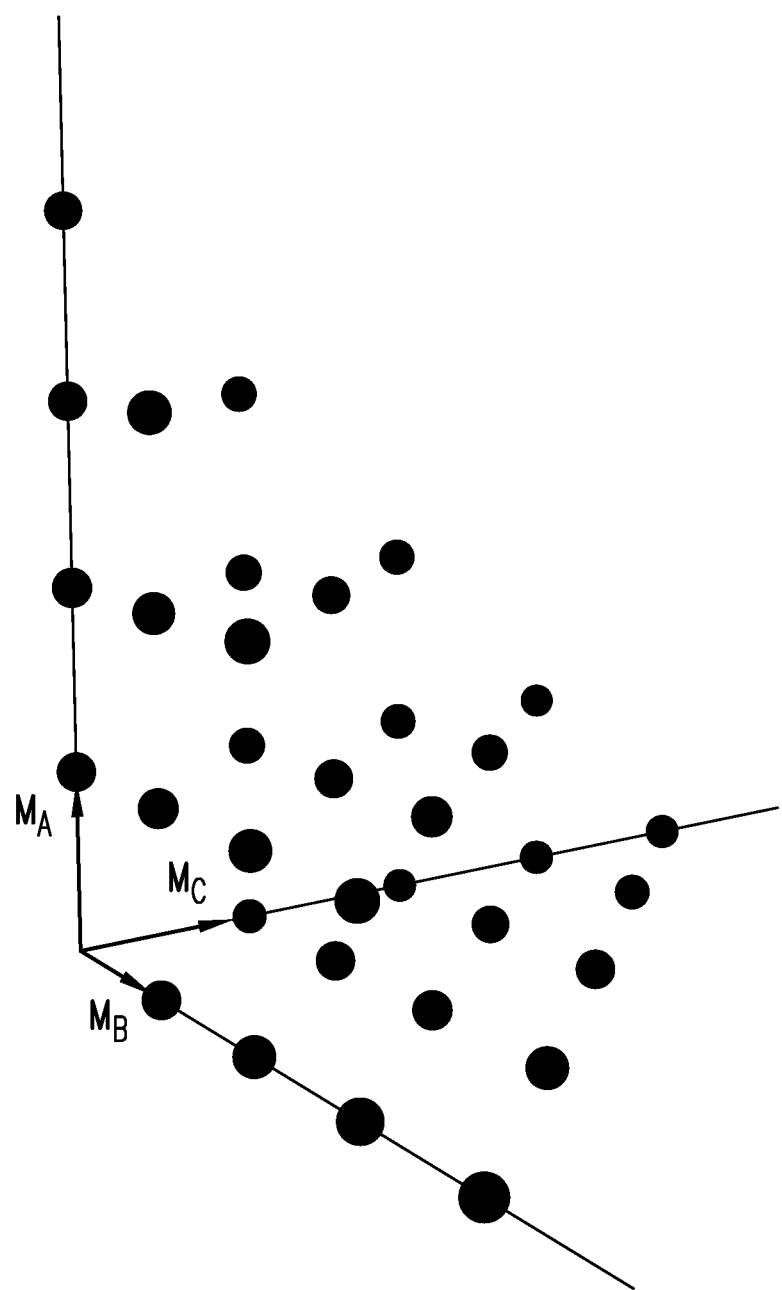
FIG. 3c is a two-dimensional projection of a three-dimensional ternary composition lattice.
Figure 3D:
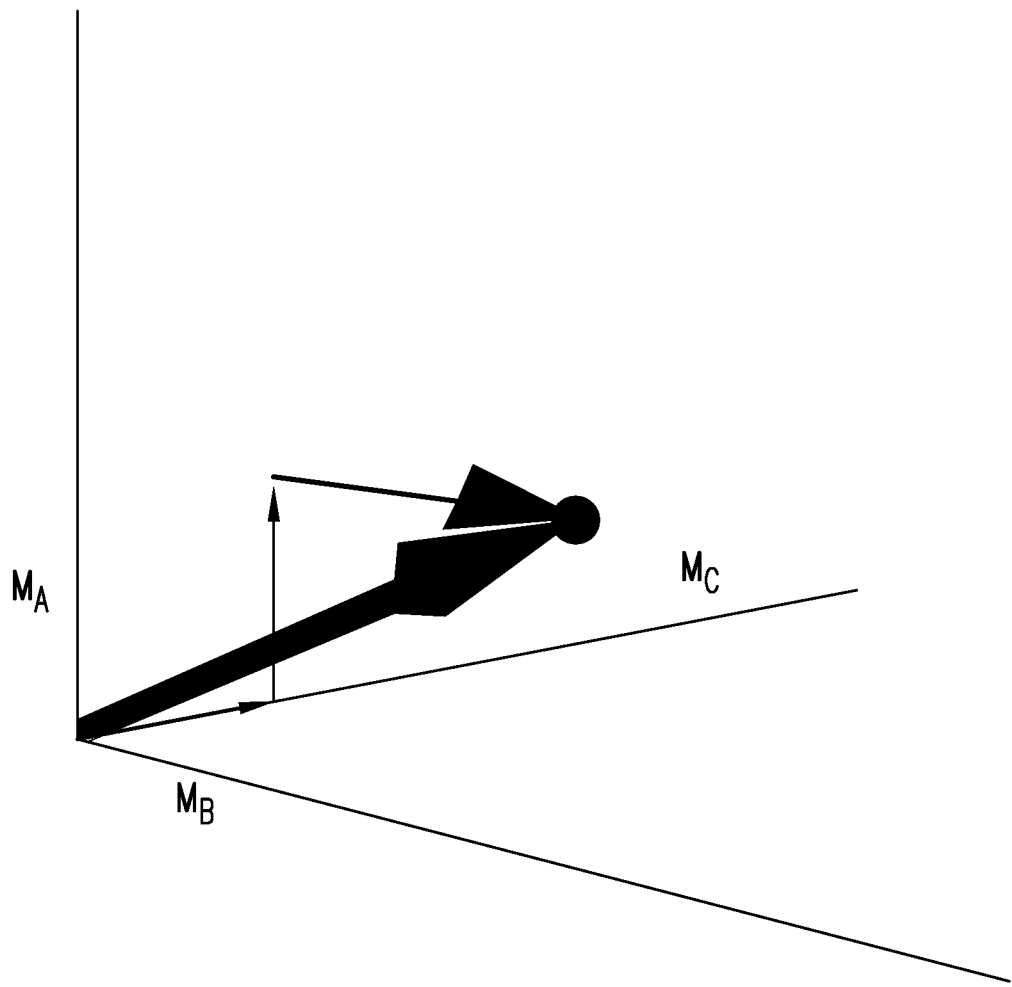
FIG. 3d is a two-dimensional projection of composition vectors in a three-dimensional ternary composition space with the resultant composition vector and lattice point illustrated.

Compositions within this system are the vector sum of masses $M_A + M_B + M_C = M_{Tot}$. As in the binary system case, this represents a constraint on the possible compositions based on the principle of conservation of mass. Geometrically the foregoing equation is the equation of a plane and because only positive masses are permitted then only compositions which lie between the intersections on the positive axes are possible. This section of the plane is the simplex for the space and is an equilateral triangle with vertices coincident with the component axes and equidistant from the origin. FIG. 3A shows a projection of the simplex triangle, FIG. 3B shows how composition vectors of different masses define a family of parallel simplex triangles. FIG. 3C shows a projection of a composition space lattice for a ternary system. FIG. 3D shows a projection of composition space with a resultant vector composition.

Figure 3E:
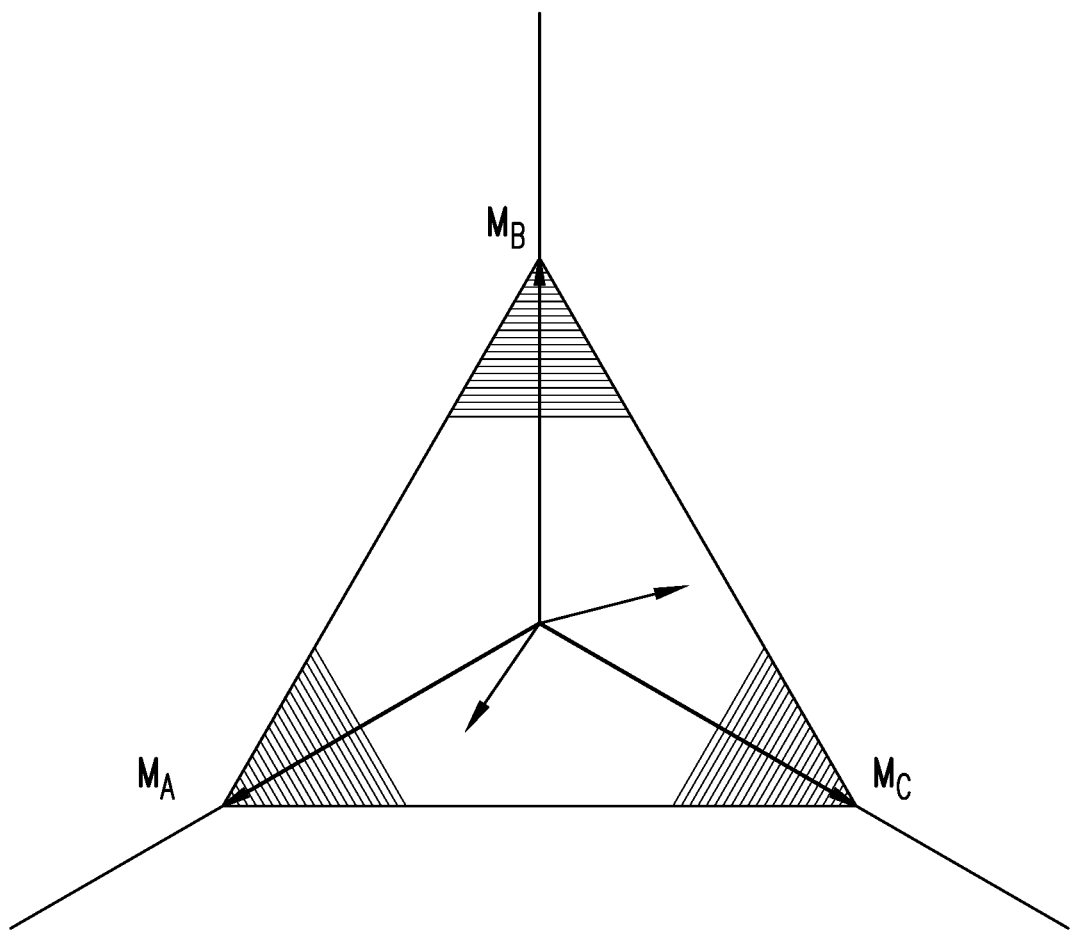
FIG. 3e is a two-dimensional projection of a three-dimensional ternary composition lattice viewed normal to plane of the simplex triangle illustrating the origin of the equilateral ternary composition diagram used to represent ternary compositions in the plane.
Figure 4:
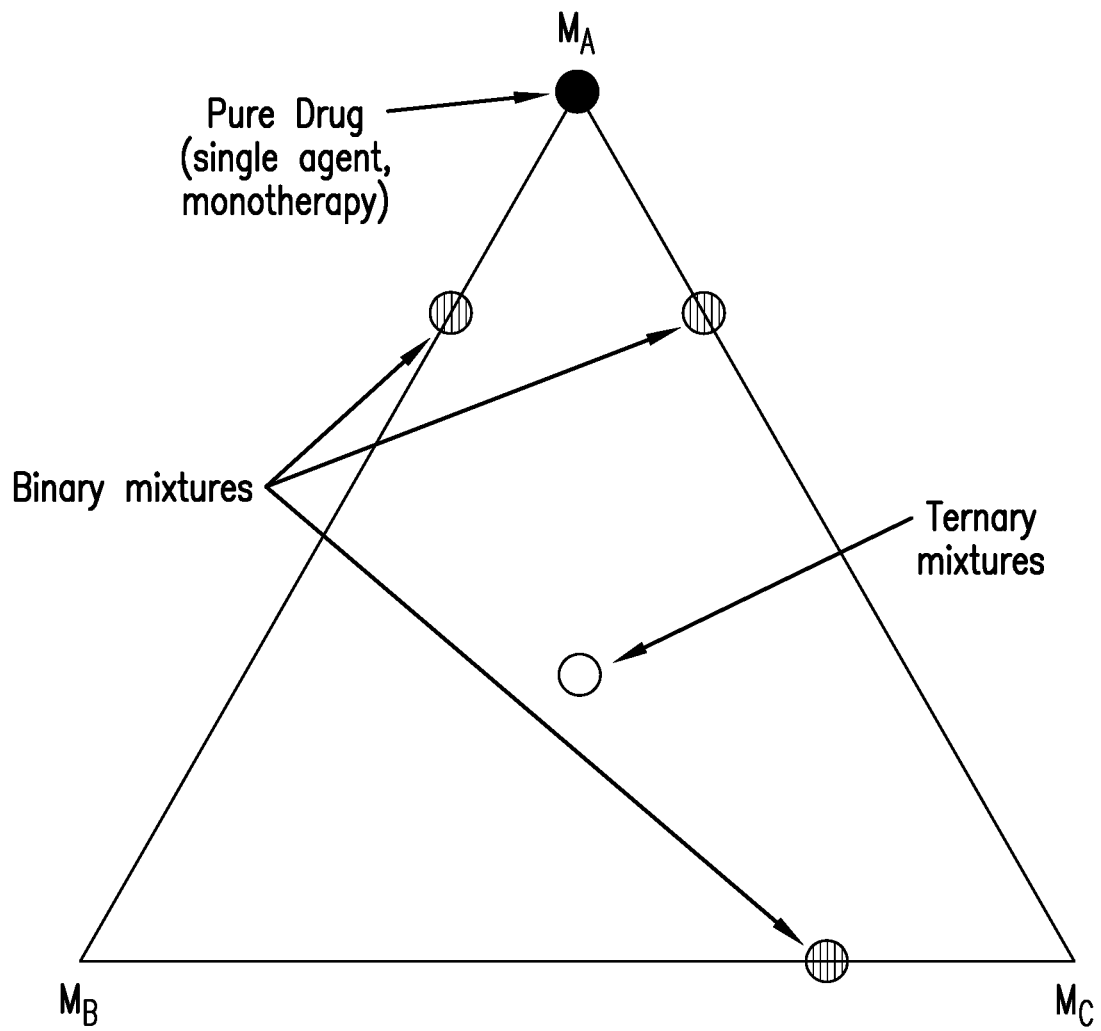
FIG. 4 is a ternary mass composition diagram for drugs A, B, C with pure drug, binary and ternary mixtures indicated.

Because the equilateral triangle simplex is a plane figure (dimension 2) it is useful to represent ternary systems by plotting only the simplex (the equilateral triangle) in two dimensions. When the Cartesian coordinates of the ternary composition space are transformed in this way the simplex diagram forms a barycentric coordinate system. The heads of composition vectors in the ternary composition space then appear as points on the triangle. FIG. 3E shows a (partially hatched for ease of visualization) projection of the ternary simplex triangle normal to its plane such that it is an equilateral triangle in the plane of the page. FIG. 4 shows a ternary composition diagram based on the ternary simplex. Compositions coincident with the triangle vertices are pure (monotherapy) components. Compositions which lie on an edge of the triangle are binary (two drug) compositions. Compositions which lie in the interior of the triangle are ternary (three drug) compositions. The properties of the barycentric coordinate system ensure that the conservation of mass is preserved diagrammatically. The total mass of the combination can be represented by the edge length of the triangle.

The concept of mass fractions extends to any number of dimensions also and in the ternary case the mass fraction $X_A$ of component A is given by:

$$X_A = \frac{M_A}{M_A + M_B + M_C}$$

Similarly, for the binary system case, in the ternary system mass fractions can be plotted on a simplex diagram also, allowing compositions of different masses to be plotted on the same diagram.

The composition space model provides a scheme for classification of drug delivery systems for combination therapies of which there are two limiting cases: single strength FRCs and continuously variable doses.

Single strength FRCs are represented as resultant vectors of fixed length and direction. Equivalently a single strength FRC can be considered as a single point within the composition space such as that shown in FIG. 3D.

Figure 5A:
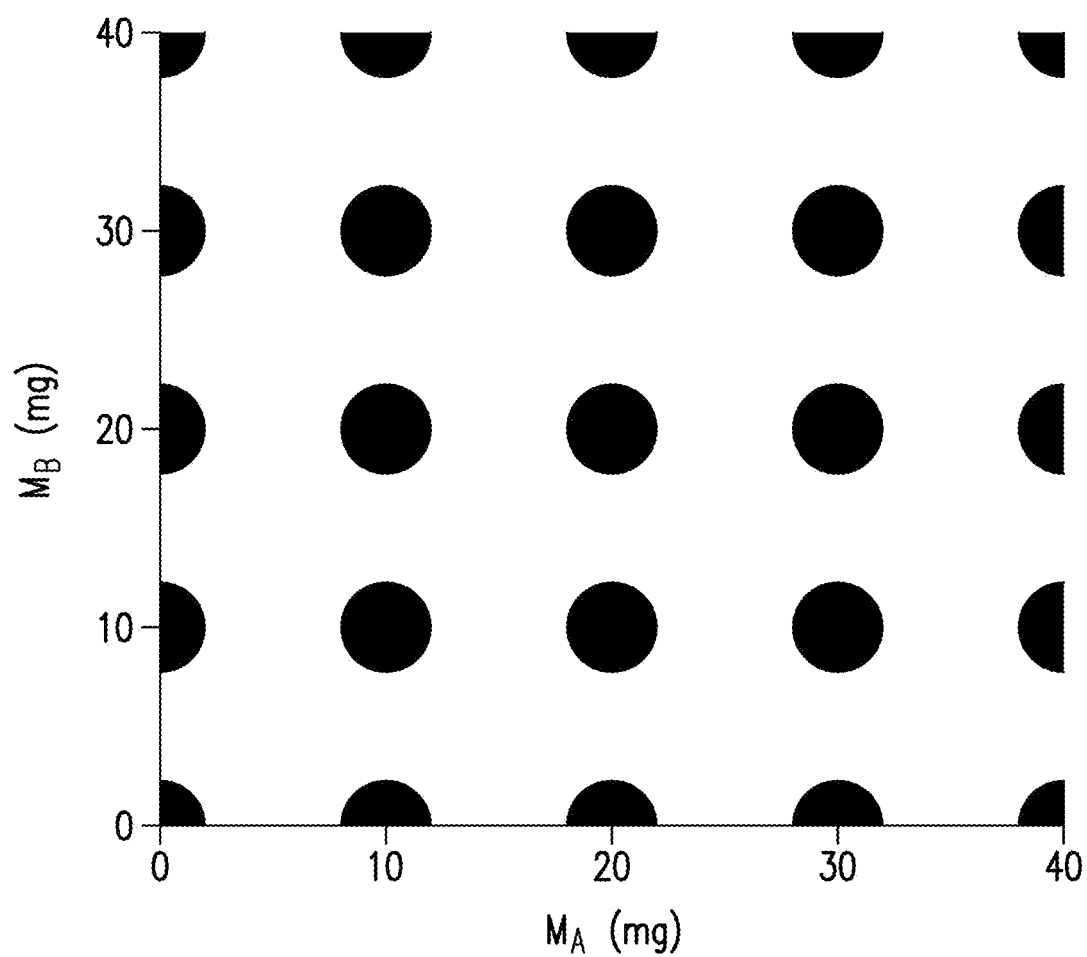
FIG. 5a is an illustration of the two-dimensional composition space for drugs A, B where the lattice points have finite extent due to the limits of precision of the dispensing mechanism.
Figure 5B:
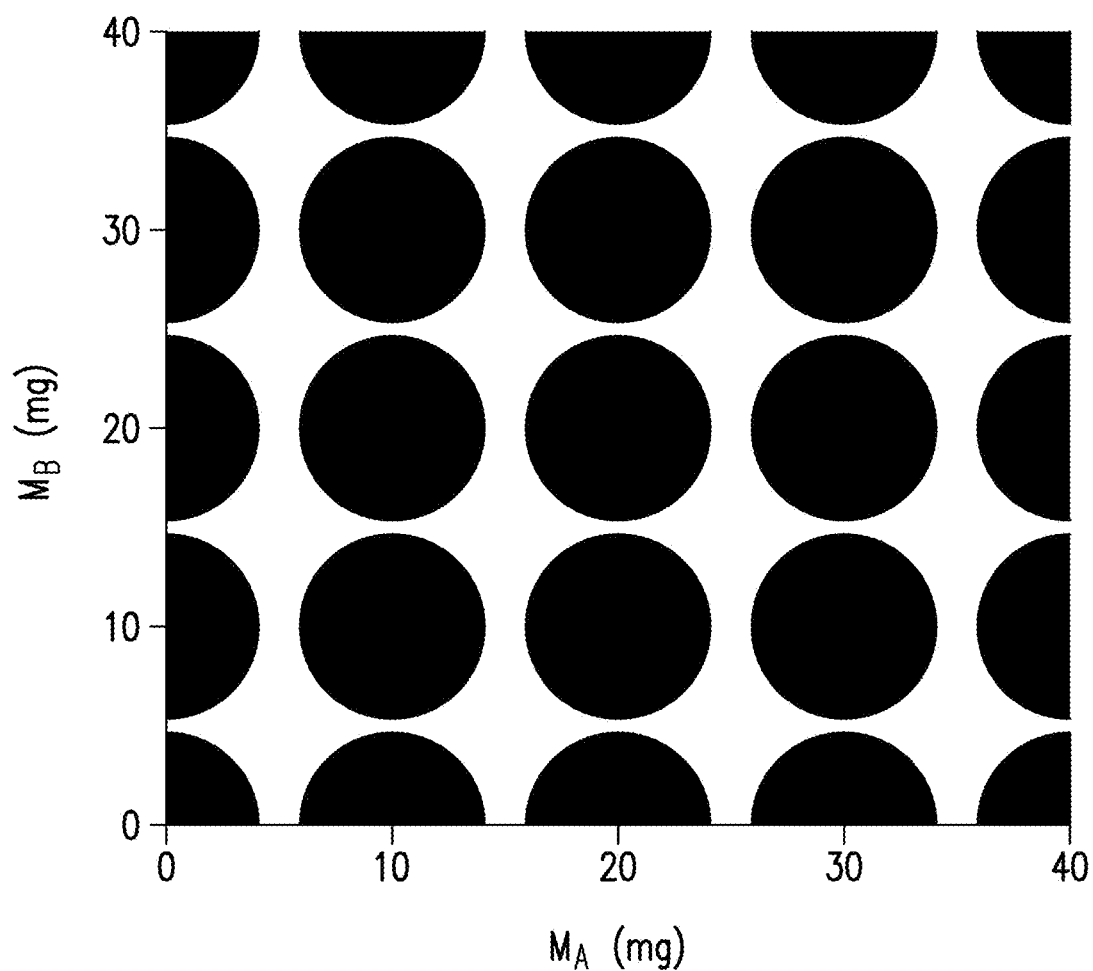
Figure 5C:
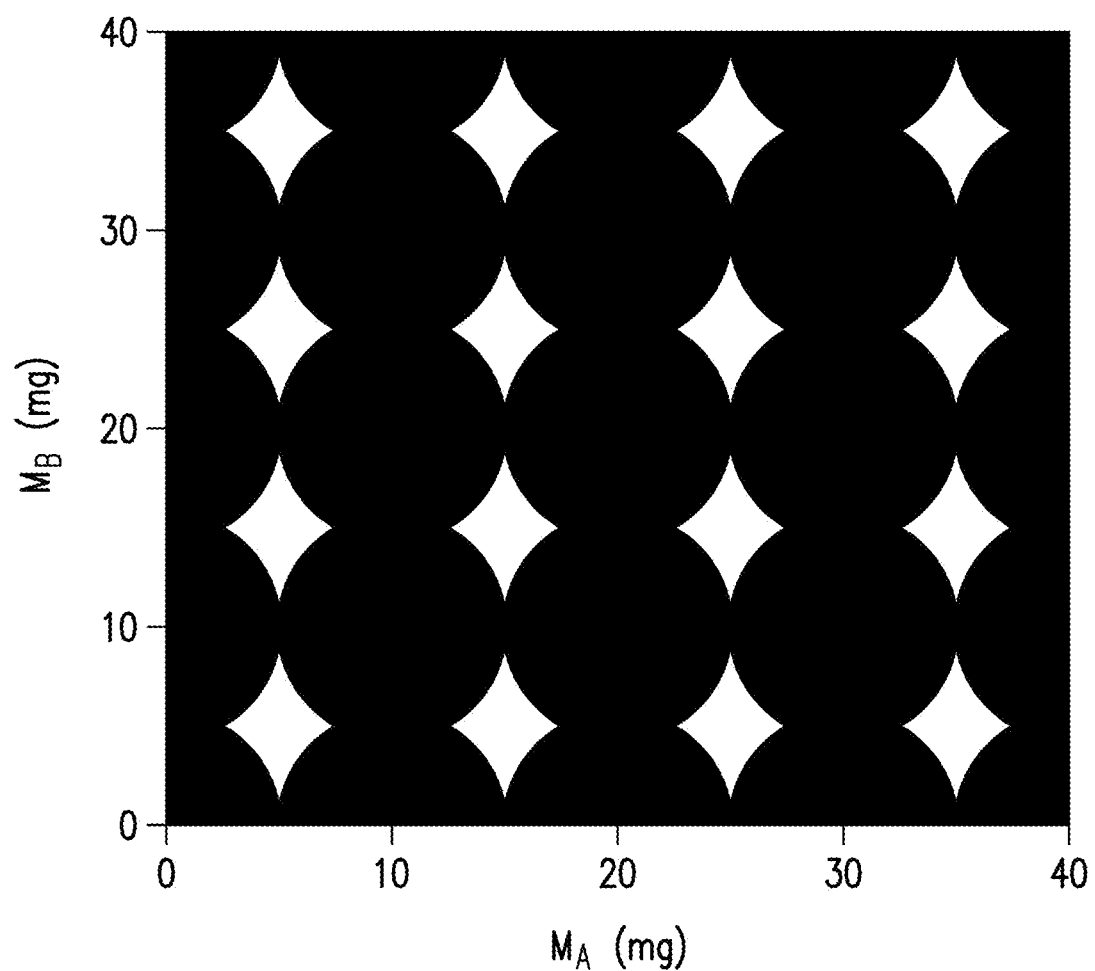
FIG. 5c is an illustration of the two-dimensional composition space for drugs A, B of FIGS. 5a, 5b where the lattice points have merged due to incapability of the dispensing mechanism.

In the other limiting case of continuously variable strengths, the lattice in composition space is fully dense and continuous such that every composition in the space can be reached. This situation is not achievable exactly in practice as it would require infinite precision in dispensing the components of the mixture, however it is possible to achieve sufficient precision in dispensing to approximate continuous dose variability for all practical purposes. That is, where the minimum achievable increment of a drug is very much smaller than the actual dose. Because of the limits of precision of any realizable dispensing device it should be understood that the lattice point model is an idealization. Due to uncertainty in dispensing, the compositions that can actually be achieved are represented by a closed region in the composition space centered on the lattice points (in the 2-dimensional binary system case, the volume is an area in the composition plane). The area or volume of this region is a statistical measure of the uncertainty or limits of precision of the dispensing system which provides a measure of the capability of a particular device design. Devices for which the dimensions of the uncertainty volume are very much smaller than the lattice point separation are capable. Conversely, devices for which the uncertainty volume of one lattice point overlaps with that of adjacent lattice points are incapable as target compositions become indistinguishable. FIGS. 5a, 5b, 5c illustrate progressively more incapable devices on the same composition space lattice using the area of the composition points as a measure of uncertainty. In FIG. 5c the composition areas overlap and the device is incapable.

Between these two limiting cases, there is an infinity of lattices of varying density. The limiting cases represent the scenarios of minimum flexibility for the single strength FRC example and maximum complexity for the continuously variable case. Practical realization of devices based on the continuously variable case for multiple components relies on the provision of an independent precision dispensing system for each component, which requires sophisticated control systems.

According to the present invention, by applying the combinatorial principle to the design of drug delivery devices, it is possible to construct devices which can combine small integral unit doses together in multiple ways such that a wide range of compositions can be reached flexibly and in embodiments said configurations can be realized at the point of care or at any other point in the supply chain. At its simplest, this can be described as follows. If two drugs A, B are desired in ratios of A 60 mg:B 20 mg, A 40 mg:B 40 mg and A 20 mg:B 60 mg, then instead of formulating each of these compositions as an FRC in a single vial for each ratio, instead all of the desired strengths and ratios could be achieved by combinations of A 20 mg and B 20 mg vials. For example, A 60 mg:B 20 mg is achieved by combining 3×20 mg of A and 1×20 mg of B. Similarly for the other ratios, A 40 mg:B 40 mg is 2×20 mg A+2×20 mg B. In principle, all three combinations can be achieved without waste with only two single-agent vial types. All of the manufacturing and analytical complexity of co-formulation as a FRC is avoided. A further advantage over formulation in a FRC is that other combinations can also be readily produced by combining different numbers of 20 mg vials of each component. For example, A 80 mg:B 20 mg is achieved by combining 4×20 mg vials of A and 1×20 mg vials of B. The accessible compositions are limited to multiples of 20 mg which is the vector length for this system. In general, the set of all accessible compositions are described by the planar lattice of points formed from linear combinations of the basis vectors for A and B, each of length 20 mg.

With this example, even in the binary case the usefulness of the combinatorial approach in terms of flexibility and simplicity over co-formulated FRCs can be seen. These advantages become greater still in the case of ternary and higher order mixtures.

Considering now the combination of three drugs A, B, C the composition space is the ternary A-B-C system. Assume again that each drug is individually available in single-agent vials of strength 20 mg. The possible combinations (accessible compositions) are given by the three-dimensional space lattice formed from linear combinations of the basis vectors A, B, C, each of length 20 mg. The addition of an extra dimension greatly multiplies the number of lattice points compared to the planar lattice of the binary example. This is a geometric representation of the fact that many more combinations are possible with three objects than is the case for two objects. FIG. 3D shows a 3-dimensional projection of the combination formed from 2×20 mg A, 3×20 mg B and 1×20 mg C.

In principle, the lattice of accessible compositions is infinite in extent in the positive direction. In practice there are of course limitations on the number of integral unit doses that can be combined which limits the lattice to finite extent determined by the permissible number of unit doses of each type (per dimension). Moreover, there is of course a pharmacological limit to the amount of drug required in a dose, which can or needs to be delivered depending on efficacy and or toxicity. A practical device for the combination of integral unit doses of drug can only have a finite number of positions. For the purposes of exposition, these positions shall be called nests. The integral unit doses of drugs shall be called vials however, it is to be understood that the physical state of the drug and the type of container is arbitrary for the purposes of this analysis. Enumeration of the accessible compositions achievable with a given set of vials of each drug and a finite number of nests makes use of combinatorial formulae. In addition to the number of nests and unit doses, a set of occupancy rules are also required. The occupancy rules include whether it is permissible for a nest to be left vacant and whether the unit doses of the different drugs are interchangeable or if they can only occupy nests of a specific type (e.g. as may be the case where 'poka-yoke' design has been used to ensure that an incorrect vial cannot be inserted into the wrong nest).

For example, consider the case of two drugs A-B each available in 20 mg single-agent vials. In a first example, consider the case of four nests, each of which must be occupied but where the vials (drugs) may be interchanged between nests. The number of accessible compositions is given by the permitted number of arrangements of the vials among the nests. In this case the combinations are easily enumerated as AAAA, AAAB, AABB, ABBB, BBBB, hence there are five accessible compositions: 80 mg A, 80 mg B, 60 mg A:20 mg B, 40 mg A:40 mg B:20 mg A:60 mg B. Note because the order of occupancy is not relevant to the relative masses of the drugs, AABB is equivalent to BBAA, ABAB and BABA and so on.

Now consider the situation when the constraint on occupancy is relaxed. Vacant nests can be treated as a third object type E. In this case, there are 15 accessible combinations including the empty configuration EEEE. Table 1 shows the occupancy of nests and the resulting masses of A and B and the total composition mass.

TABLE 1

| Nest occupancy | Mass A (mg) | Mass B (mg) | Total Mass (mg) |
|---|---|---|---|
| AAAA | 80 | 0 | 80 |
| AAAB | 60 | 20 | 80 |
| AABB | 40 | 40 | 80 |
| ABBB | 20 | 60 | 80 |
| BBBB | 0 | 80 | 80 |
| AAAE | 60 | 0 | 60 |
| AAEE | 40 | 0 | 40 |
| AEEE | 20 | 0 | 20 |
| ABEE | 20 | 20 | 40 |
| AABE | 40 | 20 | 60 |
| ABBE | 20 | 40 | 60 |
| BEEE | 0 | 20 | 20 |
| BBEE | 0 | 40 | 40 |
| BBBE | 0 | 60 | 60 |
| EEEE | 0 | 0 | 0 |

Figure 6A:
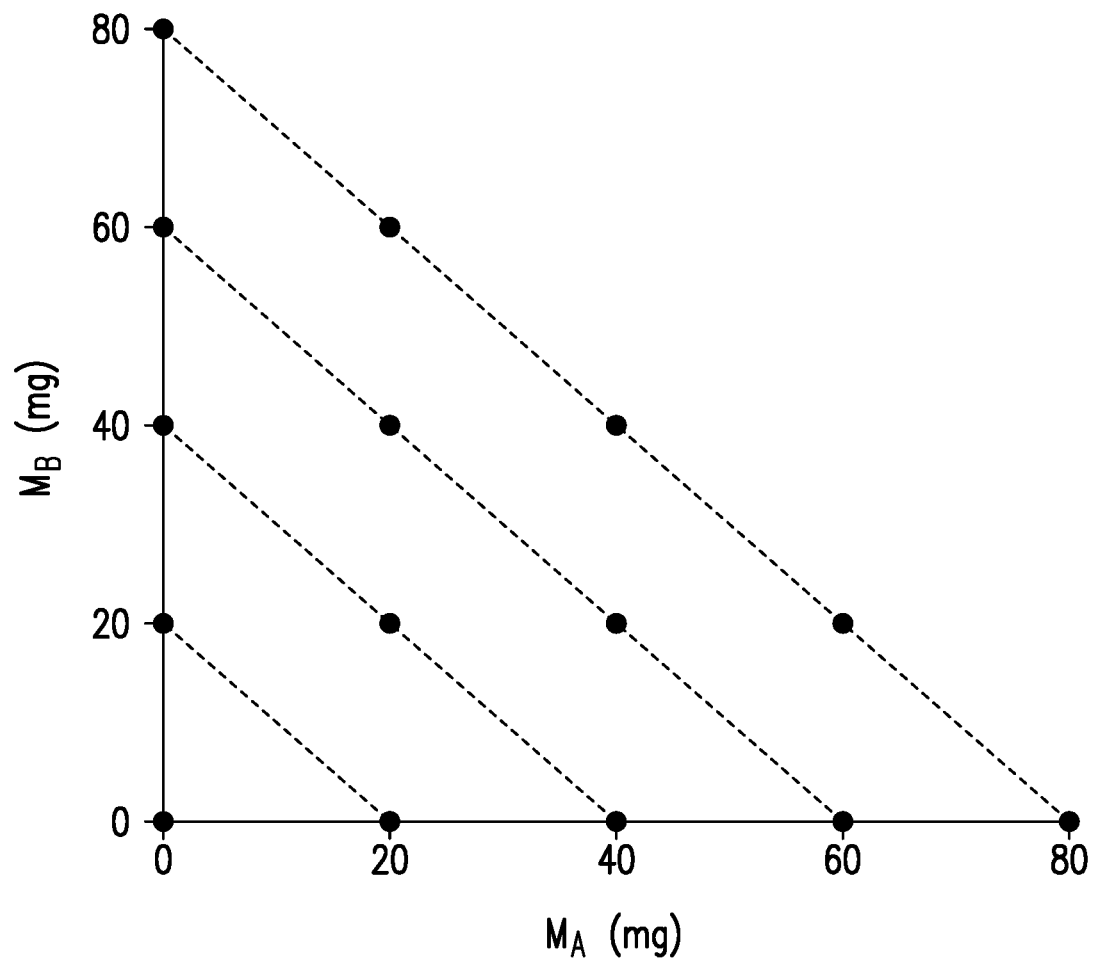
FIG. 6a is an illustration of the finite set of two-dimensional compositions and the simplex lines achievable from a device constructed with four (4) nests each of which can be vacant or receive a 20 mg vial of drug A or B.
Figure 6B:
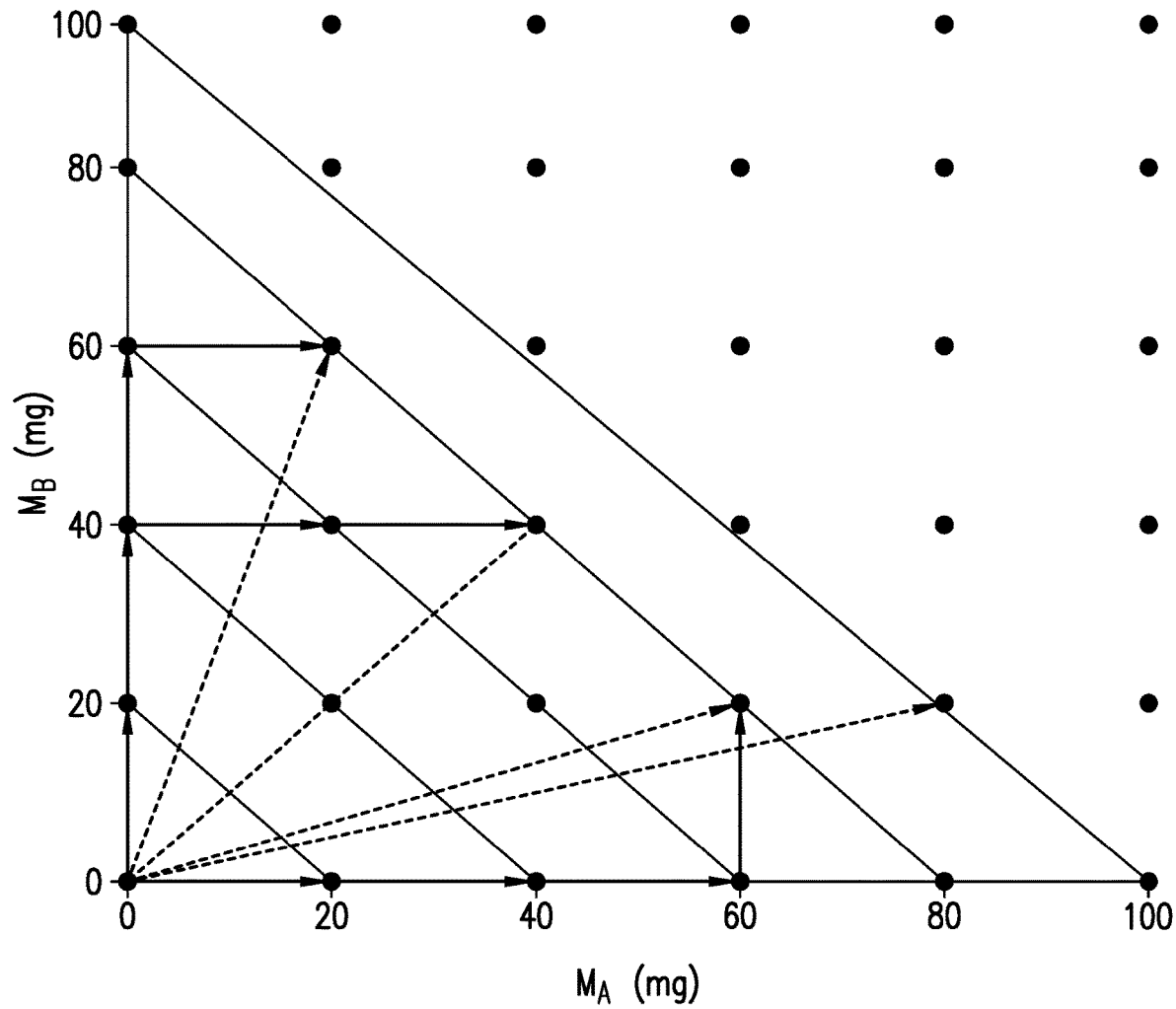
FIG. 6b is an illustration of the extended lattice of two-dimensional compositions and the achievable compositions restricted to the simplex lines achievable from a device constructed with four (4) nests each of which can be vacant or receive a 20 mg vial of drug A or B. Several resultant compositions of strength 80 mg and 100 mg are shown.

FIG. 6a shows the two-dimensional composition space and lattice for these examples. The five compositions from the first example where the constraint of full nest occupancy applies lie on the 80 mg simplex line. The additional ten compositions from the second example where empty nests are permitted lie on the 20, 40 and 60 mg simplex lines. FIG. 6b shows the vector additions and further compositions that can be reached by combinations of this limited of set of vials.

In general, when nests are interchangeable and vacancies are permissible, the number of accessible compositions is given by the multinomial coefficient:

$$(n, k)! = \frac{(n+k)!}{(n! \, k!)}$$

where n is the number of distinct single-agent vials (drugs) and k is the number of nests. With interchangeable nests and vacancies permitted, the nth multinomial coefficient is the nth triangular number.

In the ternary system A-B-C (n=3) with four interchangeable nests which may be vacant, the number of accessible compositions is 35, including the empty composition which can be disregarded. Therefore, for the A-B-C system a device with four nests for single agent vials A, B, C can replace 34 co-formulated FRCs.

Table 2 shows the combination count for the ternary system A-B-C for nest counts n=4 to n=10. By analogy with the binary case A-B where the sequence of accessible compositions increases with the addition of nests in accordance with the sequence of triangular numbers, in the ternary case the number of accessible compositions increases with the addition of nests in accordance with the sequence of tetrahedral numbers. In analogy to the binary case where the accessible compositions for a given number of fully occupied nests lie on a simplex line of constant total mass, in the ternary case, the accessible compositions for a given number of fully occupied nests lie on a ternary simplex triangle of constant total mass.

TABLE 2

| Nests | Combinations (including empty) |
|---|---|
| 4 | 35 |
| 5 | 56 |
| 6 | 84 |
| 7 | 120 |
| 8 | 165 |
| 9 | 220 |
| 10 | 286 |

Figure 7B:
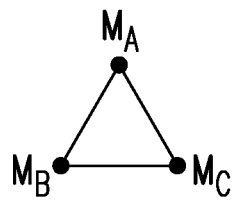
FIGS. 7b-7g are ternary mass composition diagrams of the compositions achievable from the device of FIG. 7a in increasing order of nest occupancy (empty configuration not shown).
Figure 7C:
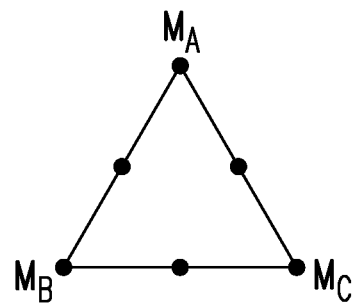
Figure 7D:
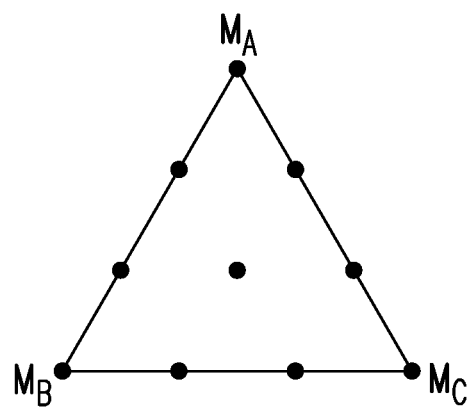
Figure 7E:
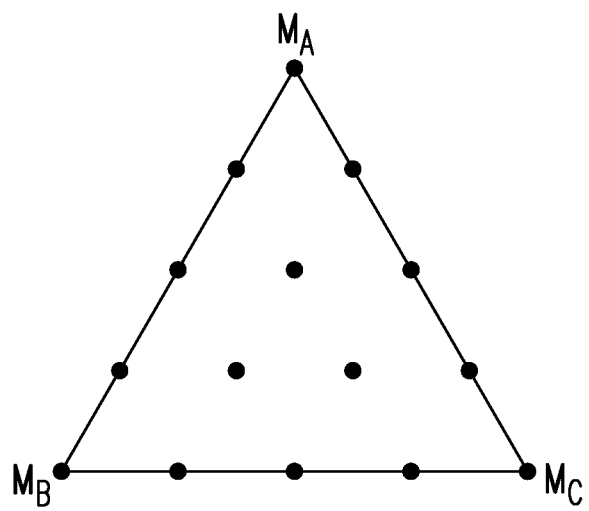
Figure 7F:
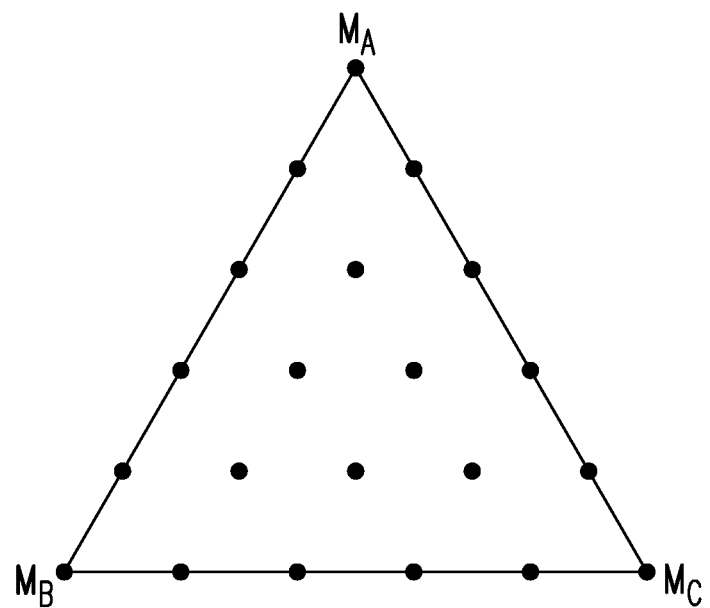
Figure 7G:
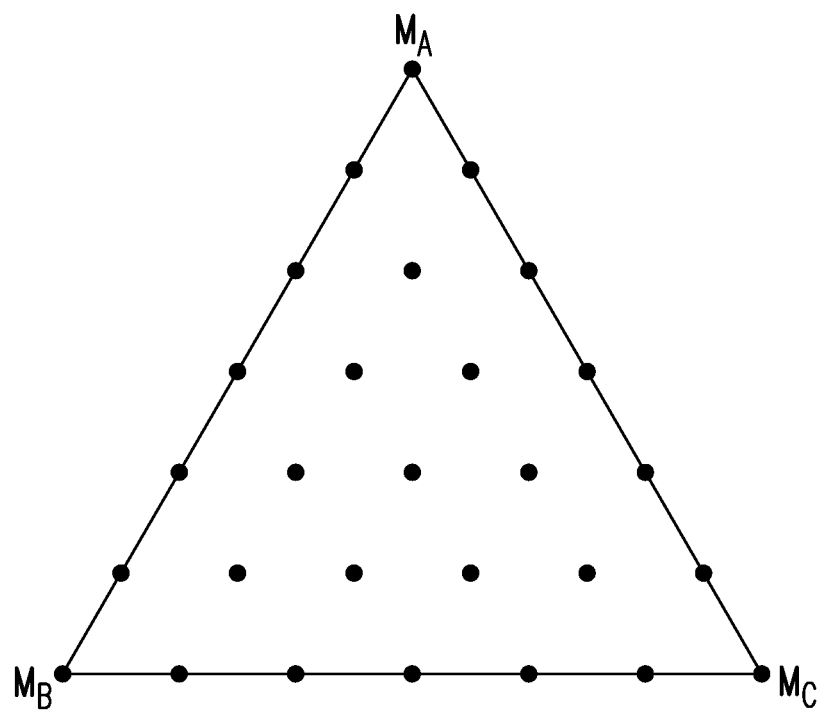
Figure 8A:
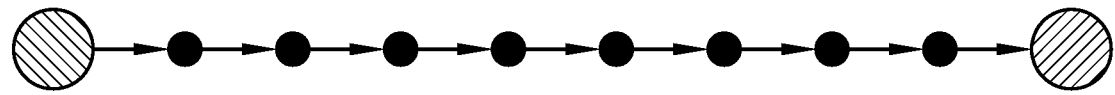
FIGS. 8a-d are schematic illustrations of various arrangements of the connections between nests including series, parallel and series-parallel arrangements.
Figure 8B:
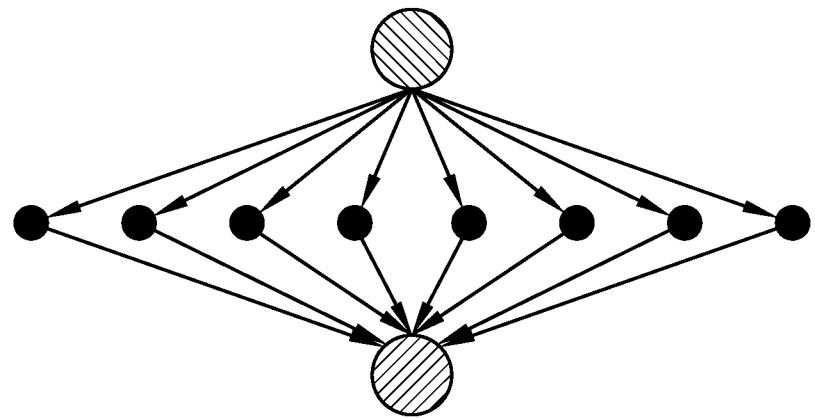
Figure 8C:
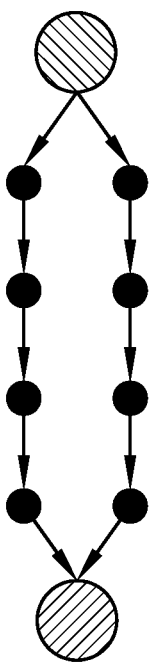
Figure 8D:
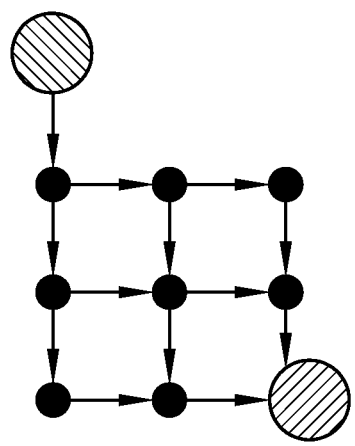

FIG. 7a shows a schematic device with six (6) nests for three (3) different single-agent vials where the nests are interchangeable and vacancies are permissible. The vials in the nests are connected in a series arrangement. FIGS. 7a2, 7a3, and 7a4 show the vials in the nests being connected in various parallel arrangements. FIGS. 7b-g are the family of simplex diagrams with edge length proportional to the composition mass for nest occupancy 1-6 showing all 120 compositions that can be reached with this system (excluding the empty composition).

The foregoing descriptions of the accessible compositions demonstrates that a large number of compositions is accessible with a small number of nests and with fixed strength vials. Further flexibility and fine-tuning of the accessible compositions can be achieved by the provision of multiple strengths (masses) of each drug. For simplicity of exposition also, in the examples, all of the drugs have been limited to a single fixed strength however, it should be understood that this is not a limitation of the invention and the strengths of each drug can be different.

Table 2 illustrates how the number of accessible compositions, and hence how dose flexibility increases, with increasing number of nests. However, the addition of more nests increases device complexity also so that there is a need to balance dose flexibility and device complexity through optimization of the number and configuration of nests. The above examples have used interchangeable nests however, devices can be built in accordance with the present invention with non-interchangeable nests such that only vials of specific drug type can be used in a corresponding nest. This reduces the range of compositions, which can be reached however, it may enable a simpler device and reduce the risk of assembly or loading errors. In such a device, the nests are effectively grouped by vial type and the accessible compositions are the result of the combinations of nest occupancy of each nest group with each other. Mathematically this is the product of the number of combinations per nest group. Consider the example of a device with six (6) nests divided into two groups of three (3) nests for drugs A and B respectively. Assuming that vacancies (E) are permitted and nests are unordered, the number of combinations per nest group is easily enumerated, e.g. for vial A as AAA, AAE, AEE, EEE, giving a result of 4 combinations per nest group and since there are 2 nest groups then the number of accessible compositions is 4×4=16. In this example, the number of combinations per nest group were easily enumerated however more generally the number can be obtained from the binomial formula (available in Microsoft Excel as the function COMBINA):

$$\binom{N+K-1}{N-1}$$

where N is the number of distinct single-agent vials and K is the number of nests. With N=2 (vials and vacancies) and K=3 the formula returns the result four (4). It should be understood that the foregoing example is readily extended to the addition of further nest groups for additional drug vials. For instance, a device with three (3) groups of three (3) nests for three (3) drugs A, B, C has $4^3$=64 accessible compositions.

The connectivity of nests can also have a significant impact on device flexibility and complexity. In general, nests can be connected in several ways such as in series, in parallel or series-parallel. For example, in embodiments, the nests of one nest group may be connected in series with the nest groups themselves connected in parallel. FIGS. 8a, 8b, 8c, 8d respectively illustrate series, parallel and two examples of series-parallel connections of nests. Nests are represented as small solid circles and connections as arrows indicating the flow direction. The larger hatched circles represent the fluid source and sink respectively. It shall be understood that these examples are in no way intended to limit the possible arrangements of nest connections. In embodiments, the drug container may be designed in such a way that the connections between the nests are integral to the design of the container. In such cases, it may be necessary to include empty containers in the configurations where the accessible composition requires some vacant nests, this is especially likely to be the case for nests connected in series where continuity of the fluid path requires a connection.

In embodiments, nests or nest groups may be connected in a parallel arrangement directly to hypodermic needles such that the simultaneous subcutaneous administration of multiple drugs from multiple needles is performed. This may be beneficial for example when due to incompatibilities the drugs of the combination cannot be combined prior to delivery into the patient.

Typically the active ingredient of a drug product is not provided in its pure state but is instead co-formulated with various excipients which may include but are not limited to water (as solvent), pH modifiers, buffers, viscosity modifiers, tonicity modifiers, enzymes. In liquid stable biologic formulations the main component overall by mass is usually water. When using the composition space model only the mass of active ingredients need be considered with no loss of precision or generality. A further advantage of the combinatorial approach over the precise metering approach is that when masses of active drug in each discrete integral unit dose are known, the concentration of the active ingredient in the formulation can be disregarded whereas in the case of precise metering from reservoirs, accurate dispensing of each active ingredient is reliant on precise knowledge of concentration because dosing is indirect based on formulation volume or mass. For precise metering from a reservoir, therefore the concentration must be known with precision. Typically, liquid stable biologic formulations have a tolerance range for concentration from batch to batch therefore precision metering requires the concentration for each batch of each component to be known and entered as a parameter into the control software.

It is a feature of the present invention that a single instance of a device based on the combinatorial principle configured to deliver a specific combination ratio is itself a single strength FRC represented in composition space as a single point, however the design of the device being configurable in accordance with the combinatorial principle, is able to access a range of compositions defined by the lattice for the particular system. The lattice can therefore be thought of as the family of potential device configurations accessible by the system. This systemic feature of the invention has several advantages. It enables the device provided to the end user to be simple in that it has no user configuration options to select from (reducing the risk of medication errors) and does not require the entry of parameters such as drug concentration. In addition, it is not reliant on a complex dose metering system as its purpose is simply to deliver its entire contents. This also means that there is no drug waste (notwithstanding the inevitable small losses due to incomplete emptying of containers). In effect, devices based on the combinatorial principle enable the decoupling of device complexity from dose flexibility.

The person skilled in the art will be familiar with numerous descriptions of devices, which purport to enable the simultaneous parenteral delivery of two or more drugs. For example in U.S. Pat. No. 9,457,142 (Day et al.) disclose a dual chamber injector comprising two independent drive systems and a fluid manifold connected to both cartridges and a needle for simultaneous delivery of both drugs in a controlled ratio. The drugs are mixed in the needle. It is stated that the concept is readily extended to three chambers however, U.S. Pat. No. 9,457,142 (Day et al.) does not teach this. In practice, a device based on this principle with three independent drive systems is likely to be large, complex and cumbersome with power availability issues. The device taught by U.S. Pat. No. 9,457,142 (Day et al.) also is configured for multiple uses from the same two chambers. This, however, may be problematic since preservatives are normally prohibited by sterility concerns in the case of biologic therapies. Furthermore, for precision dosing such a device would require the accurate drug concentration in the container to be entered as a parameter and this would need to be changed from batch to batch.

Descriptions of several other devices purportedly for use in the injected delivery of drug combinations are known to those skilled in the art. However these devices are either capable only of delivering fixed ratios of drugs or are limited to only two drugs and/or are reliant on a complex electronic control system to accurately meter the intended dose. In the framework of the composition space model, devices of the former type are constrained to achieve fixed vector compositions (FRCs), and in some cases single point compositions, whereas devices of the latter type are designed to achieve as closely as practically realizable, infinitely variable compositions represented by vectors of any length and direction. Devices of the latter type, depending on the respective size of the chamber and the dose, are likely to result in unused drug, which will be wasted.

As will be shown in the following detailed description of various embodiments, by means of the aforementioned combinatorial principle the present invention enables the construction of devices configurable for the delivery of a wide range of compositions without limitation to fixed ratios or reliance on complex and highly accurate control systems and such that waste is minimized or entirely eliminated.

Further advantages of the present invention are that it reduces manufacturing complexity of co-formulated FRCs including formulation and analytical complexities and eliminates work-in-progress and finished goods inventories of the FRCs. Also by keeping the drugs separate as single agents for longer, potentially until the point of administration, the risks associated with long-term stability of FRCs is reduced or eliminated.

A characterizing feature of devices constructed according to the present invention is that, in the composition space model, the compositions achievable with the devices lie intermediate of the extremes of single point fixed ratio compositions and infinitely variable compositions. The lattice of compositions achievable from such a device is sparse. In embodiments, the sparsity of the lattice of achievable compositions can be tuned to the specific needs of the therapy to give an optimal balance of flexibility in dosing and complexity in design.

Because the combinatorial approach is independent of the physical state of the drugs involved in the combination, in embodiments, devices based on the present invention may advantageously incorporate drugs in different physical forms. In embodiments devices may be constructed to use drugs in more than one physical form. For example, one of the drugs may be present in liquid form and others present in powder form. An advantage of this configuration for the subcutaneous delivery of antibody drug combinations is that the drug density in powder form is higher than for solutions, which enables a more compact device with a potentially greater number of nests and therefore accessible compositions than could be achieved with liquid drug. In embodiments this may enable the construction of a device that can be body worn and is configurable for a wide range of compositions. If such a device is arranged to contain one drug in liquid form in a liquid reservoir such that the solution has sufficient solubility for the other powdered components of the combination, then the device can perform the in-line reconstitution of the powdered components and deliver the reconstituted solution directly to a patient. In embodiments, due to the kinetics of reconstitution of the powdered drug components it may be advantageous to provide one or more reconstitution chambers to ensure complete reconstitutions and mixing. In embodiments, means may be provided to enhance the mixing and reconstitution e.g. with stirring or shearing mechanisms.

Figure 9A:
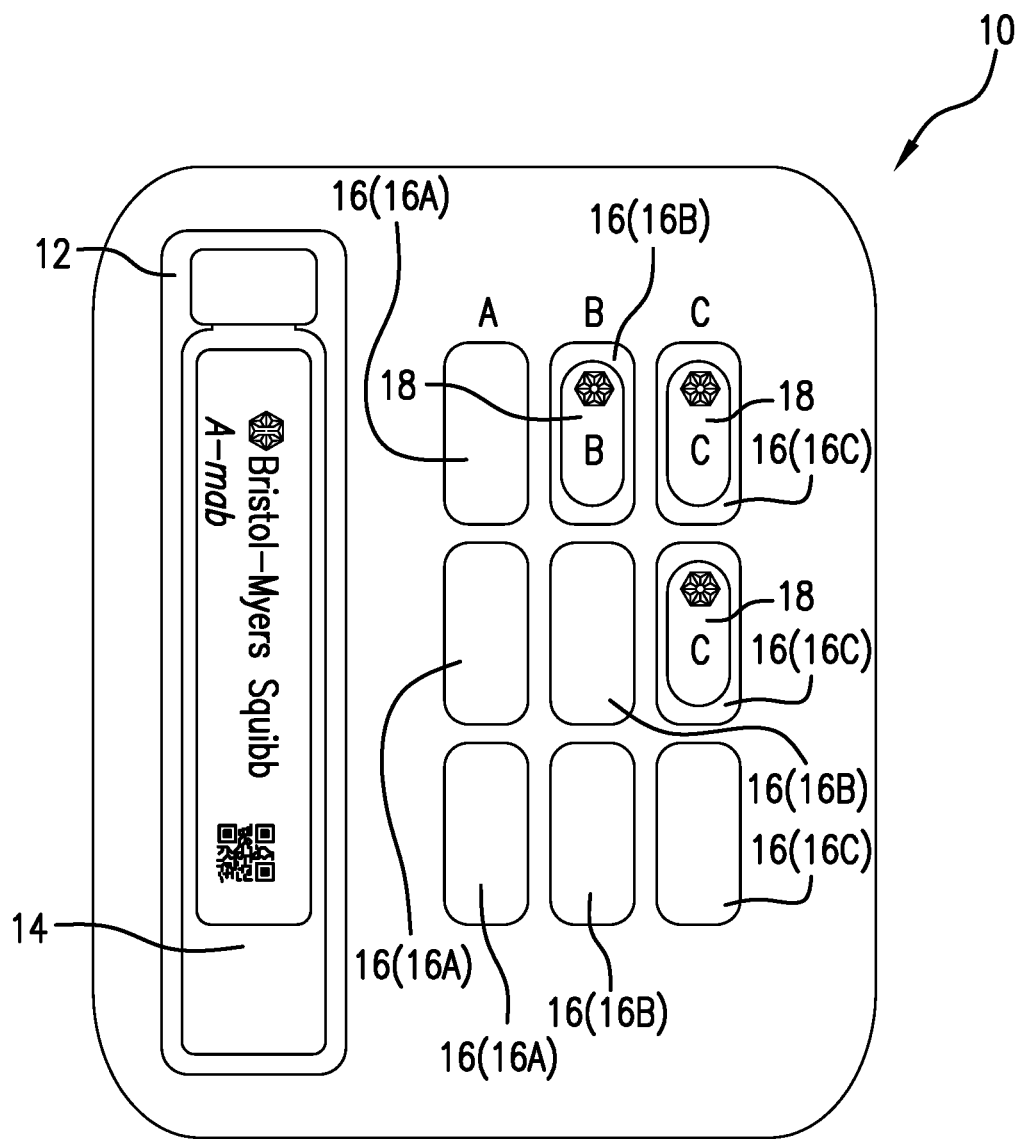
FIGS. 9a-c are schematic illustrations of a device with three groups of three non-interchangeable nests for the receipt of drug capsules and a cavity for receipt of a drug or diluent filled cartridge. In the configurations illustrated, when the cartridge is drug filled the same drug cannot be present in both cartridge and capsule form.
Figure 9B:
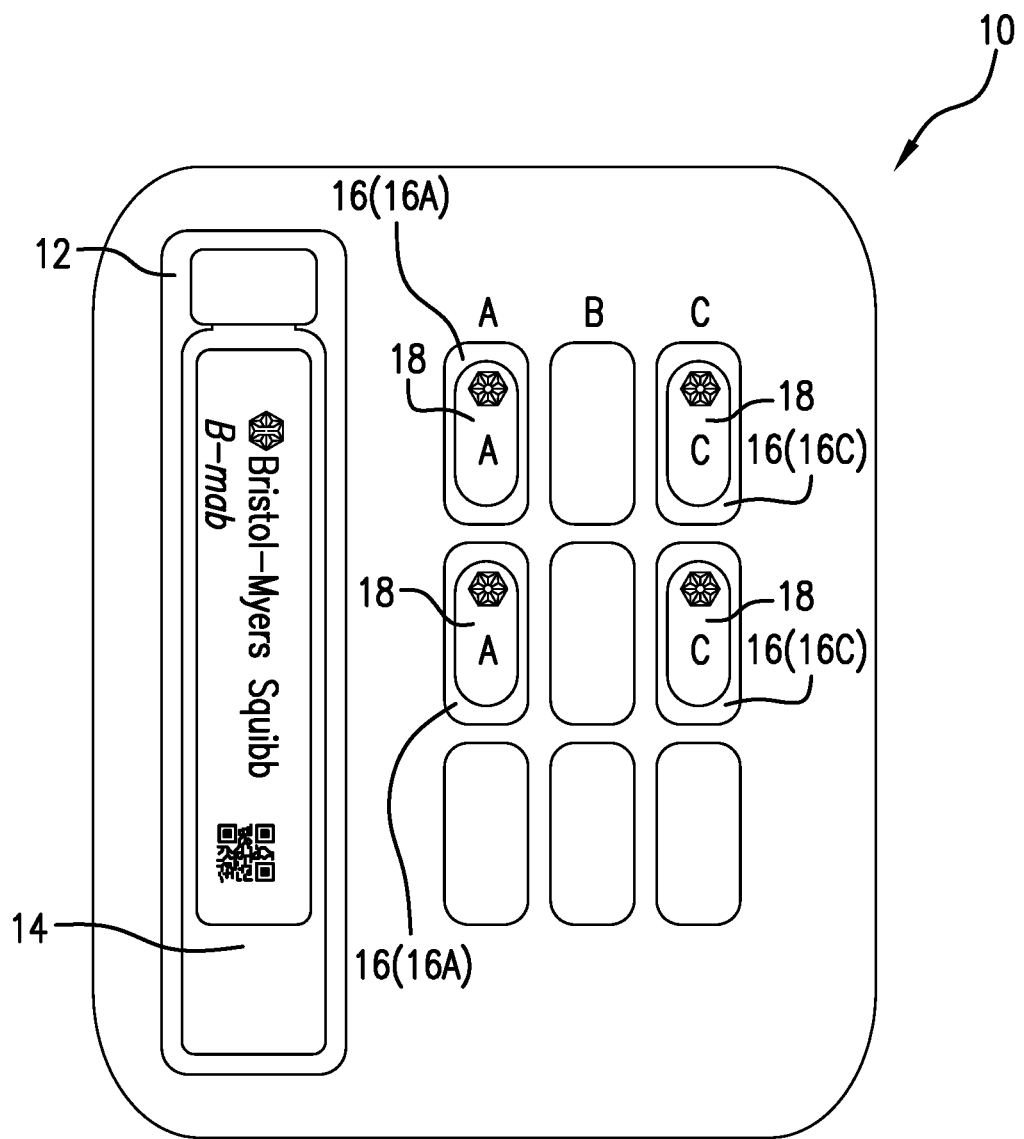
Figure 9C:
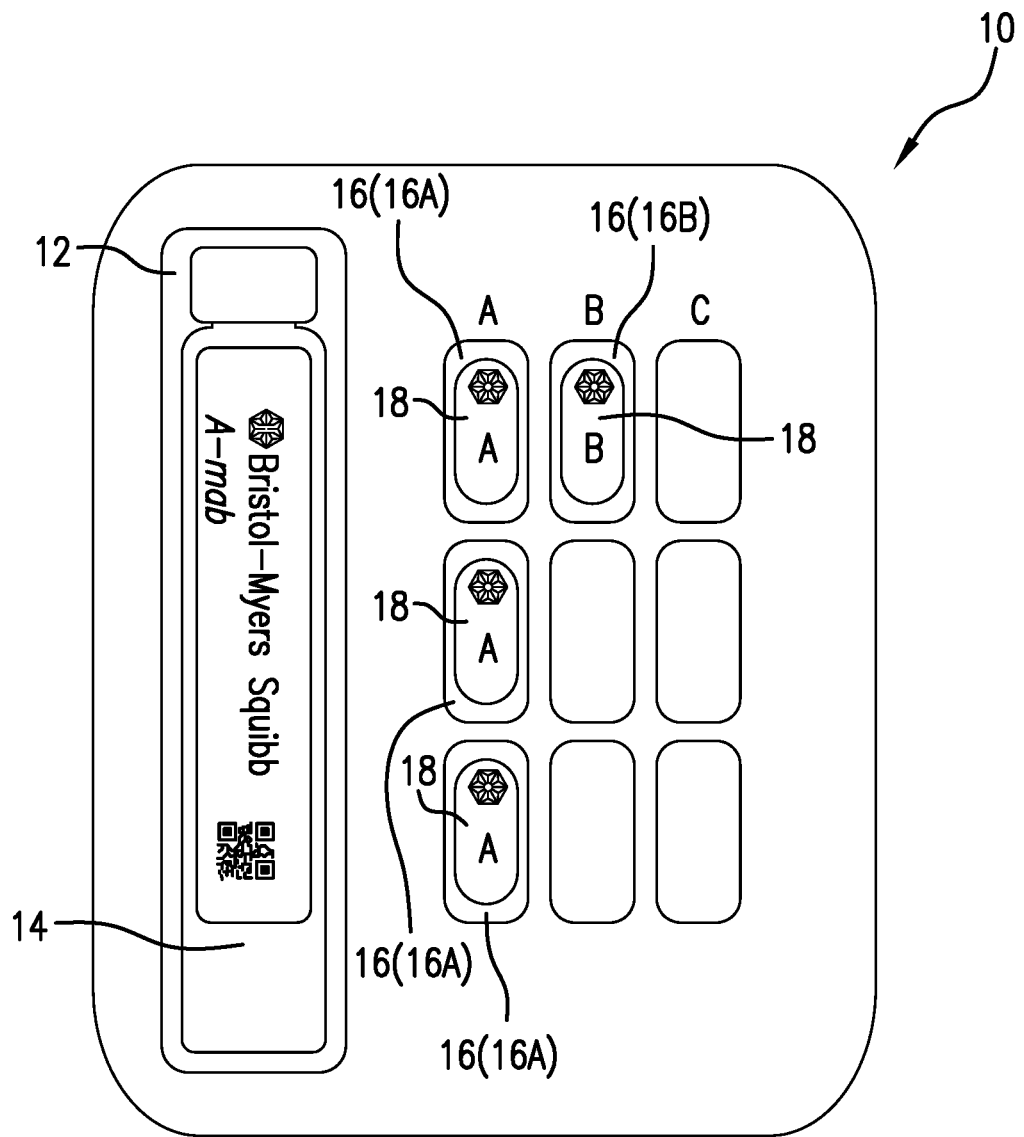
Figure 10A:
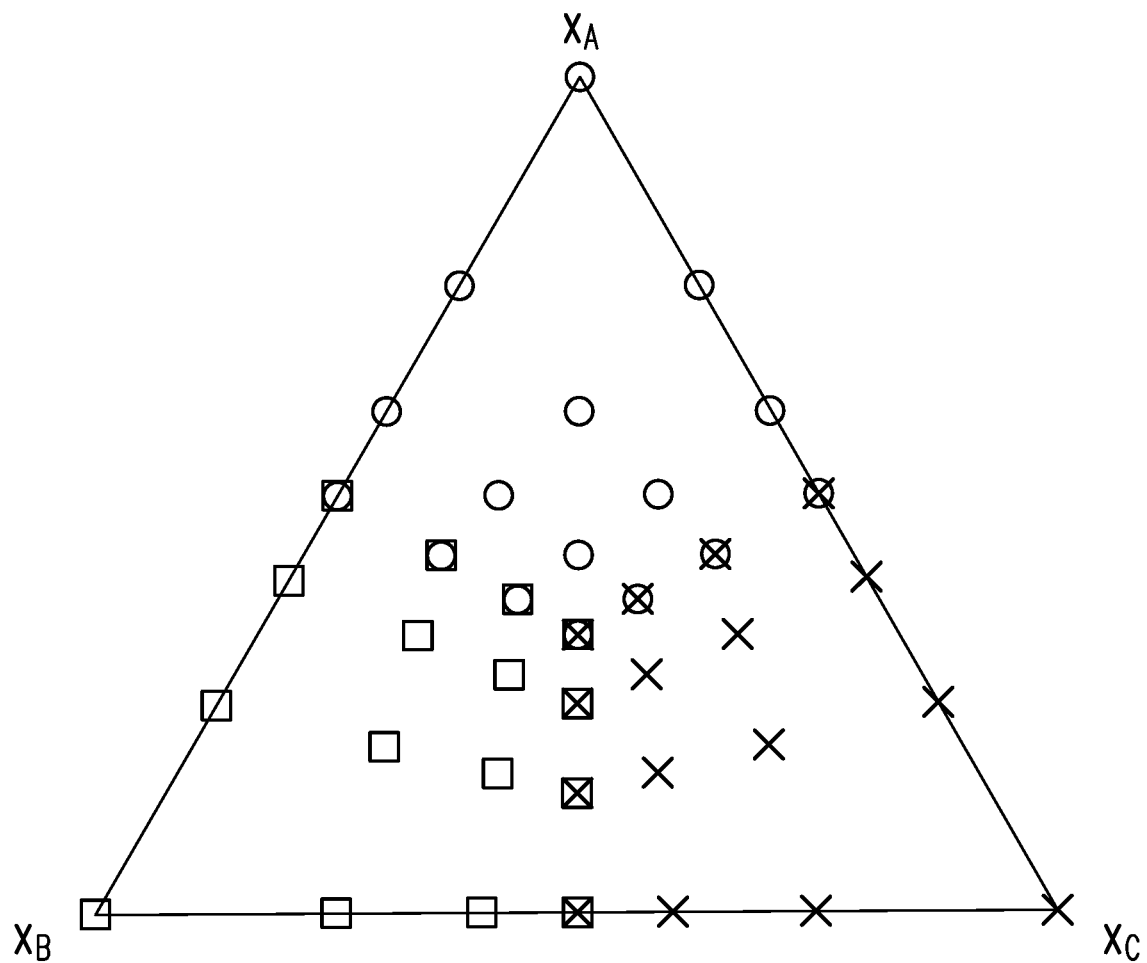
FIG. 10a is a ternary mass fraction composition diagram of the compositions achievable with the device of FIGS. 9a-c when the strength of the drug capsules is one-third the strength of the cartridge.
Figure 10B:
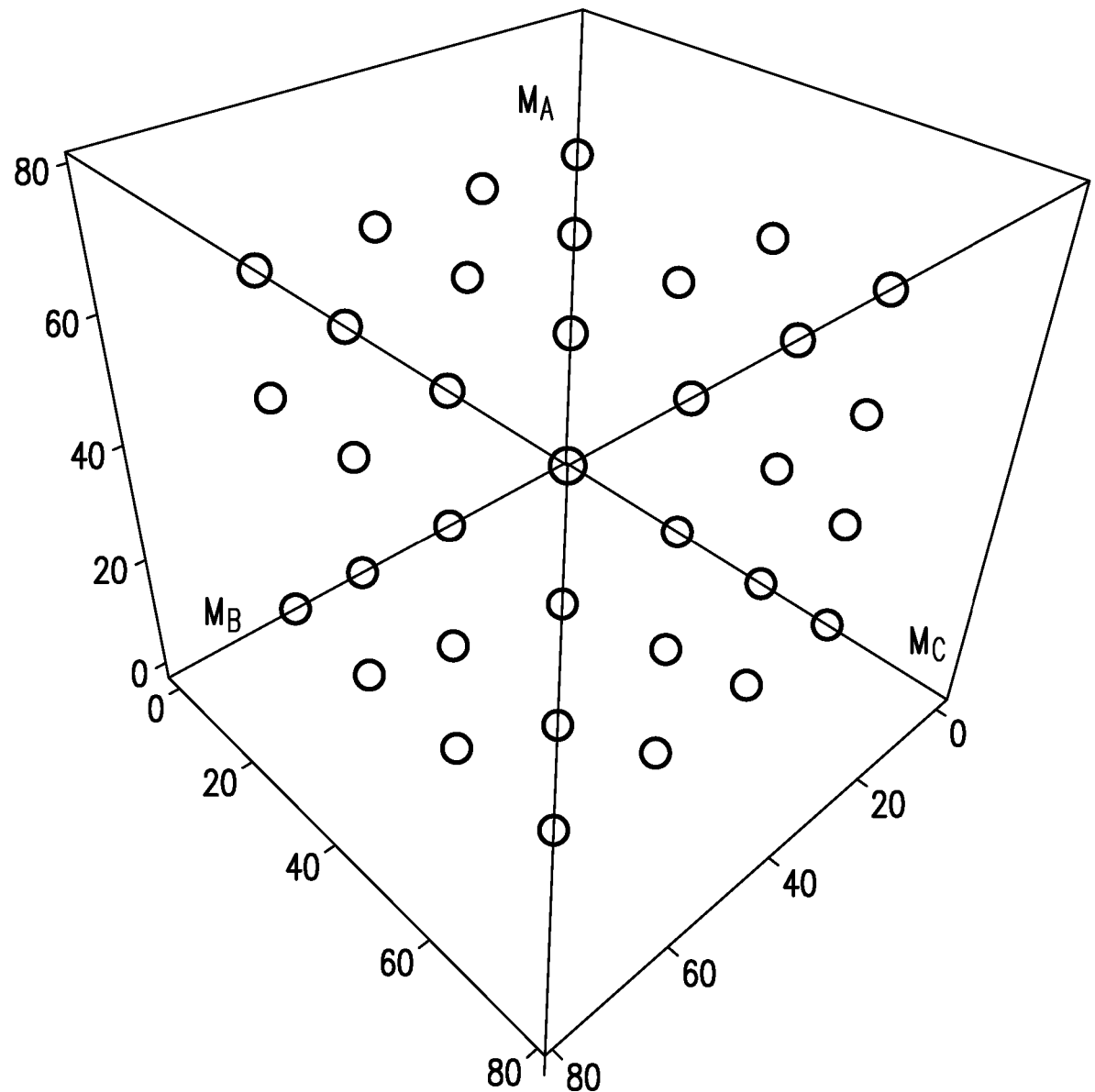
FIG. 10b is a three-dimensional projection of the compositions achievable with the device of FIG. 9a-c when configured with capsules of one-third the strength of the cartridge and the same drug is not allowed to be present in both cartridge and capsule form.

In embodiments such a device can be designed such that the contents of the liquid reservoir and the powdered drug containers can be rotated between configurations. This has the advantage that the composition space can be partitioned between configurations such that the region of the composition space that can be reached depends on how the device is configured. The benefit of this is that a smaller number of nests can access a larger range of the composition space than would otherwise be possible such that the device can be simpler overall whilst the device system can provide considerable complexity. FIGS. 9a, 9b, 9c shows one such embodiment of a device 10 based on this principle. The device 10 comprises a chamber 12 for the receipt of a liquid filled drug reservoir 14 and three groups (A, B, C) of three nests 16 (16A, 16B, 16C) for the receipt of powdered drug containers 18. For the purposes of exposition the liquid reservoir 14 shall be called the cartridge and the powder containers 18 shall be called capsules however it is to be understood that this in no way limits the design of either the liquid reservoir or the powder containers. The rules for nest occupancy are that the nests 16 may be vacant but only capsules 18 of one drug type can occupy each nest group (16A, 16B, 16C). In the example, the device 10 is arranged such that the mass of drug in each capsule 18 is one third of that contained in the liquid reservoir 14 such that three capsules 18 are required to equal the strength of the cartridge 14 however it is to be understood that this is not a limitation and any ratio of the drugs between cartridges 14 and capsules 18 may be selected depending on the particular therapeutic scenario. In use, the solution in the cartridge 14 is pumped through the capsules 18 in the array of nests 16 to reconstitute the powdered drug and pump the resulting combination to the patient. Suppose that the device 10 is configured to deliver combinations of drugs from the ternary system A-B-C. If drug A is provided in liquid form in the cartridge 14 and drugs B and C are provided in powdered form (FIG. 9a) in the capsules 18, then since the mass of B and C individually can never exceed the mass of A in the cartridge 14, then a device 10 configured in this way is limited to reach only A rich compositions. Therefore if a particular therapeutic situation called for a B rich composition, then the device 10 would be configured to provide B in the cartridge 14 and A and C in capsules 18 (FIG. 9b) and likewise if a C rich composition was required then C would be provided in the cartridge 14 and A and B in capsules 18 (FIG. 9c). In this example a further restriction is applied that a drug is not allowed to be present in both liquid and powder form such that if the drug is in the cartridge 14 then its corresponding capsule nests 16 (16A, 16B, 16C) must remain empty. This restriction is a design choice and should not be considered limiting. Despite this limitation, collectively the device 10 can be configured to reach the entire composition range. FIG. 10a shows the mass fractions of the compositions that can be reached from a device 10 configured according to this example depending on which drug is provided in the cartridge 18. Notice that some of the compositions at the boundaries of the composition range for each cartridge 18 configuration are duplicated. FIG. 10b shows a projection of the 3-dimensional composition space for this device 10. It can be seen that the accessible compositions occupy the faces of a cube and the duplicated compositions lie on the edges of the cube.

With the limitation that a drug cannot be simultaneously present in both liquid and powder form, if the design of the capsules 18 were universal such that they could be interchanged between nest groups (16A, 16B, 16C) then in a further embodiment the device 10 could be simplified further still by having only two groups (A, B) of three nests 16 (16A, 16B, 16C) without any reduction in the accessible compositions, however this reduction in complexity must be balanced against the increased risk of configuration errors.

In embodiments the use of capsules 18 interchangeable between nest groups (16A, 16B, 16C) can allow for more compositions to be reached, e.g. by enabling the use of more than three capsules 18 of one of the component drugs across more than one nest group (16A, 16B, 16C).

Figure 11:
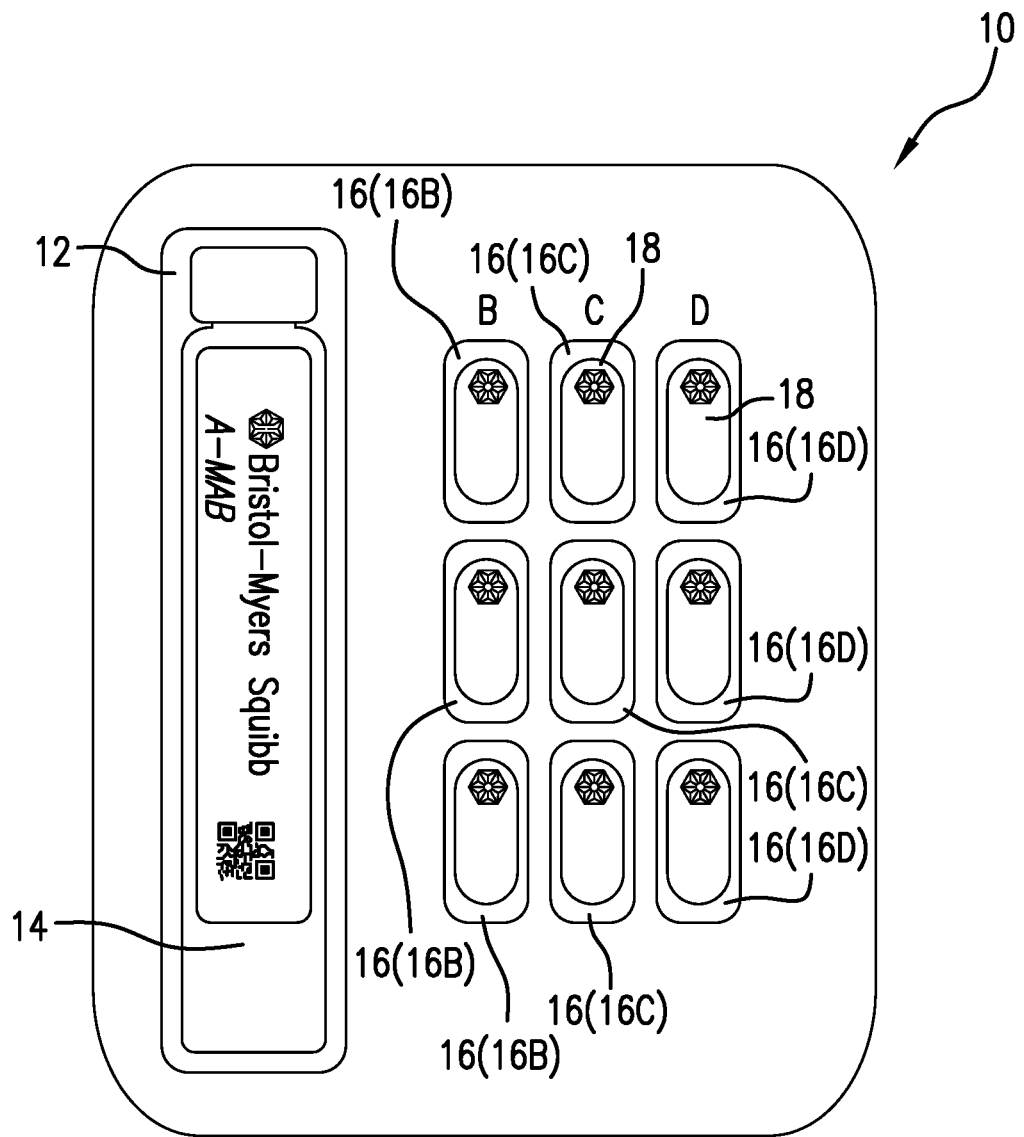
FIG. 11 is a schematic of the device of FIGS. 9a-c configured with four drugs A, B, C, D of which one drug (A illustrated) is in cartridge form and the other drugs are present in capsule form.

In embodiments, a device 10 constructed according to the example could be configured to deliver quaternary drug combinations A, B, C, D, for example by providing drug A in cartridge form and B, C and D in capsules 18 (FIG. 11).

In embodiments the cartridges 14 may contain no drug, only a solvent or diluent for reconstitution of the capsule 18 contents. This may be required for example for solubility reasons. A potential advantage of such embodiments is that avoidance of liquid product may avoid the need for refrigerated storage and distribution.

Inevitably, when emptying containers (cartridges, capsules) there is always some residual volume unused which is wasted. Minimizing the number of containers used is therefore important to minimize waste however doing so reduces the number of accessible compositions that can be reached. Careful design of the number and arrangement of containers and nests is therefore important for optimization of accessible compositions and waste. Preferably, the total volume of the fluid path should be kept to a minimum to minimize the waste associated with the residual volume of the fluid path.

In embodiments drug waste can be reduced by the adoption of certain design features. In one such embodiment, when configurations for which some nests are unused are required, means to block those nests to remove them from the fluid path, e.g. valves, can be incorporated.

In embodiments, collapsible containers (cartridges, capsules) may be used with means to collapse the containers to expel residual drug product and minimize residual volume at the end of delivery.

In embodiments such means may include but are not limited to servo motors, springs, elastomeric elements.

In embodiments, shape memory materials known to the person skilled in the art may be utilized to provide the means to collapse the containers.

In embodiments said shape memory materials may be of the polymeric or metallic alloy type. In embodiments the drug container itself may be comprised of or incorporate the shape memory material.

In embodiments the device may include a diluent reservoir which is used to flush the fluid path for the delivery of residual drug.

It will be apparent to the person skilled in the art that the target composition required from a device constructed according to the present invention is the final composition achieved on complete mixing of the contents of all of the containers used in creating the combination and that during the mixing and reconstitution processes significant transient variations in composition will be present. Depending on the compatibility between the different drugs such transient variations may have deleterious effects. In such circumstances, the physical form of the drugs, the arrangement of nests and their connectivity e.g. in series, in parallel, series-parallel, and the use of diluent reservoirs may all be used to minimize said deleterious effects.

In some therapeutic situations for reasons of safety or efficacy, it may be beneficial or necessary to administer the various drug components sequentially. In some cases a precise temporal structure for the administration of the drugs comprising the combination may be required. Such situations may arise in cases where the safety or efficacy of the drugs is dependent on the order in which they are administered, e.g. because the therapeutic effect is dependent on the order of occupancy of molecular binding sites, or because of a need to regulate the rate of administration e.g. to regulate the peak plasma concentration.

It will be apparent to the person skilled in the art that such sequential administration of the drugs comprising the combination is not possible with co-formulated FRCs. It is therefore an advantage of the present invention that in embodiments, devices may be constructed which allow the programmed, sequential delivery of the drugs comprising the combination.

In embodiments the present invention is also configurable for the stratified dosing of a drug combination for a population of patients based on body weight or some other appropriate physiological measure (e.g. body mass index, biomarker assay) in the cases where the dose of one or more of the drugs comprising the combination is dependent on the physiological measurement or biomarker. In such a scenario, the patient population is divided into groups depending on the result of the measurement and the appropriate dose of each drug in the combination is administered depending on which group the patient belongs to. As described earlier, co-formulated FRCs are insufficiently flexible to allow such patient measure or biomarker based dosing. Alternatively, dose titration from typical vials can lead to waste. According to the composition space model of the drug combination, treatment regimens where one drug dose remains fixed and others may be variable based on the outcome of the measurement, or where all drugs vary based on the outcome of the measurement but at different rates, have variable compositions. The required compositions have a functional dependency on the measurement and hence describe curves in the composition space. By careful selection of the strengths and possible combinations of the integral unit doses in such a scenario, devices can be constructed such that they are configurable for the entire dose range for the population by selection of the count of each integral unit dose of each single agent only such that the same device design is used with different configurations across the population. Such devices will have all of the attendant advantages of devices based on the combinatorial principle such as minimization or elimination of waste.

Figure 12:
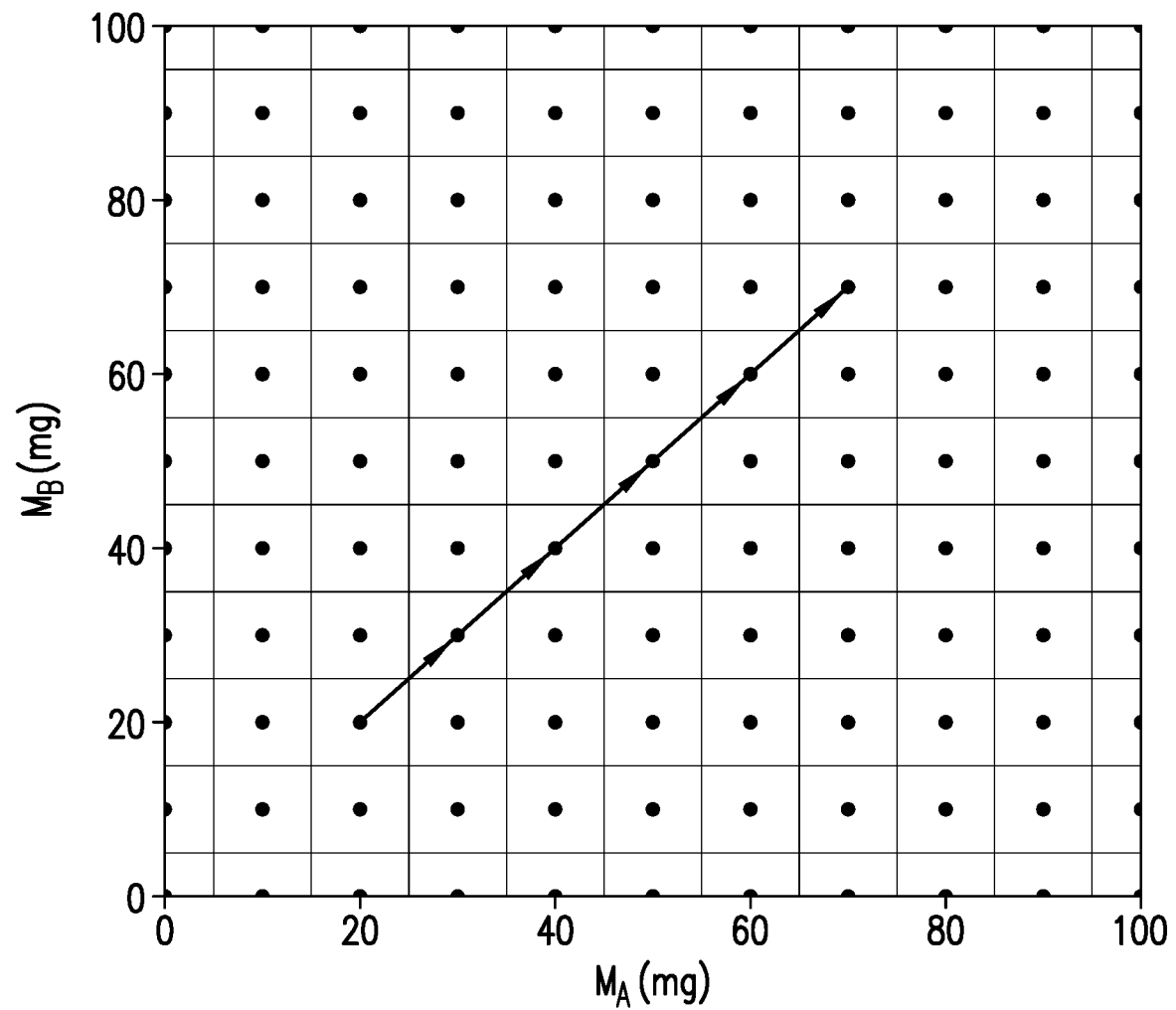
FIG. 12 is an illustration of a two-dimensional composition space for the binary system A, B divided into Voronoi cells according to a biomarker based dosing rule with a set of biomarker based dose vectors superimposed.
Figure 13A:
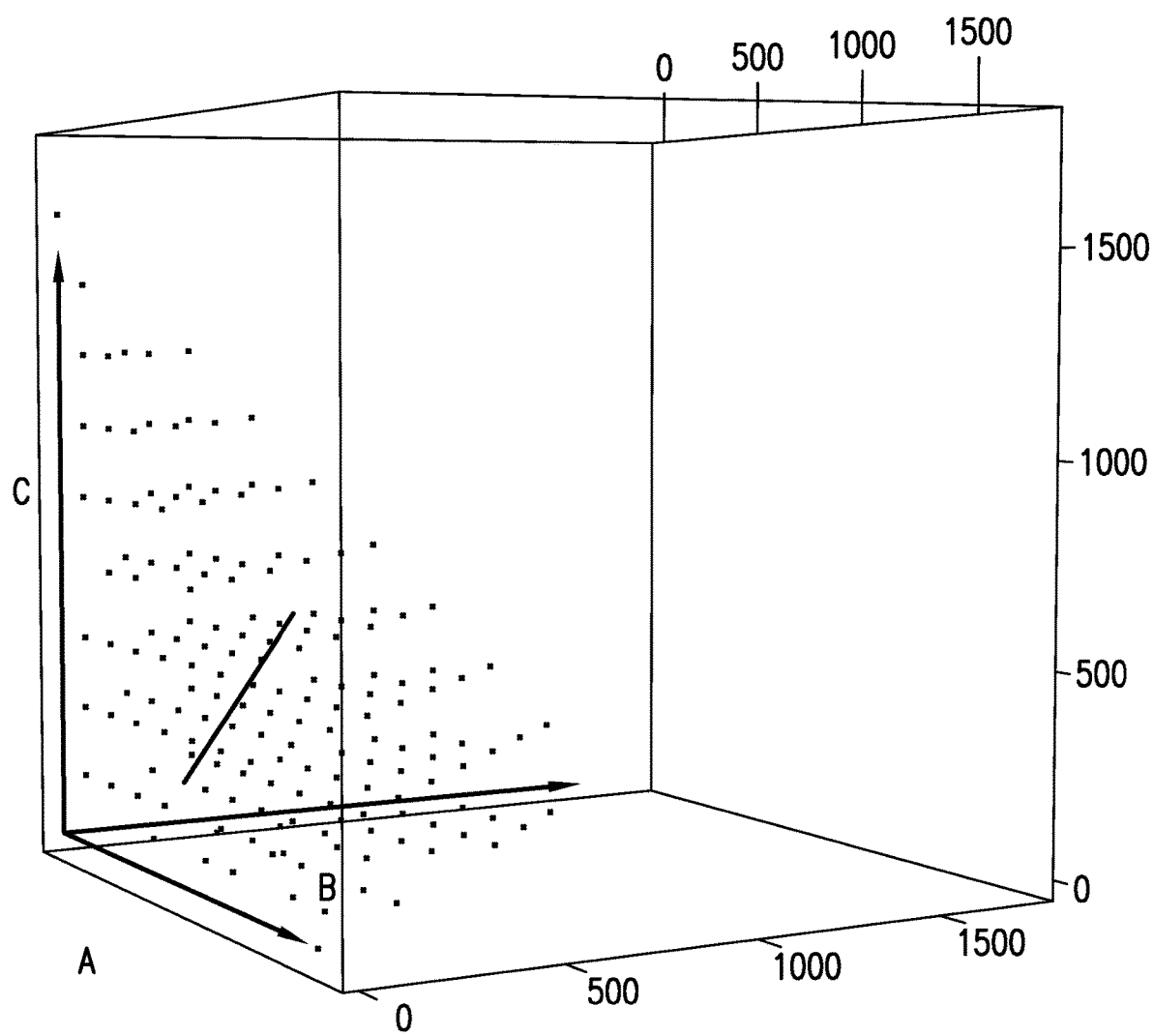
FIG. 13a is a two-dimensional projection of a three-dimensional composition space for the ternary system A, B, C illustrating the target lattice points and biomarker based dosing vectors according to the biomarker dosing rule.
Figure 13B:
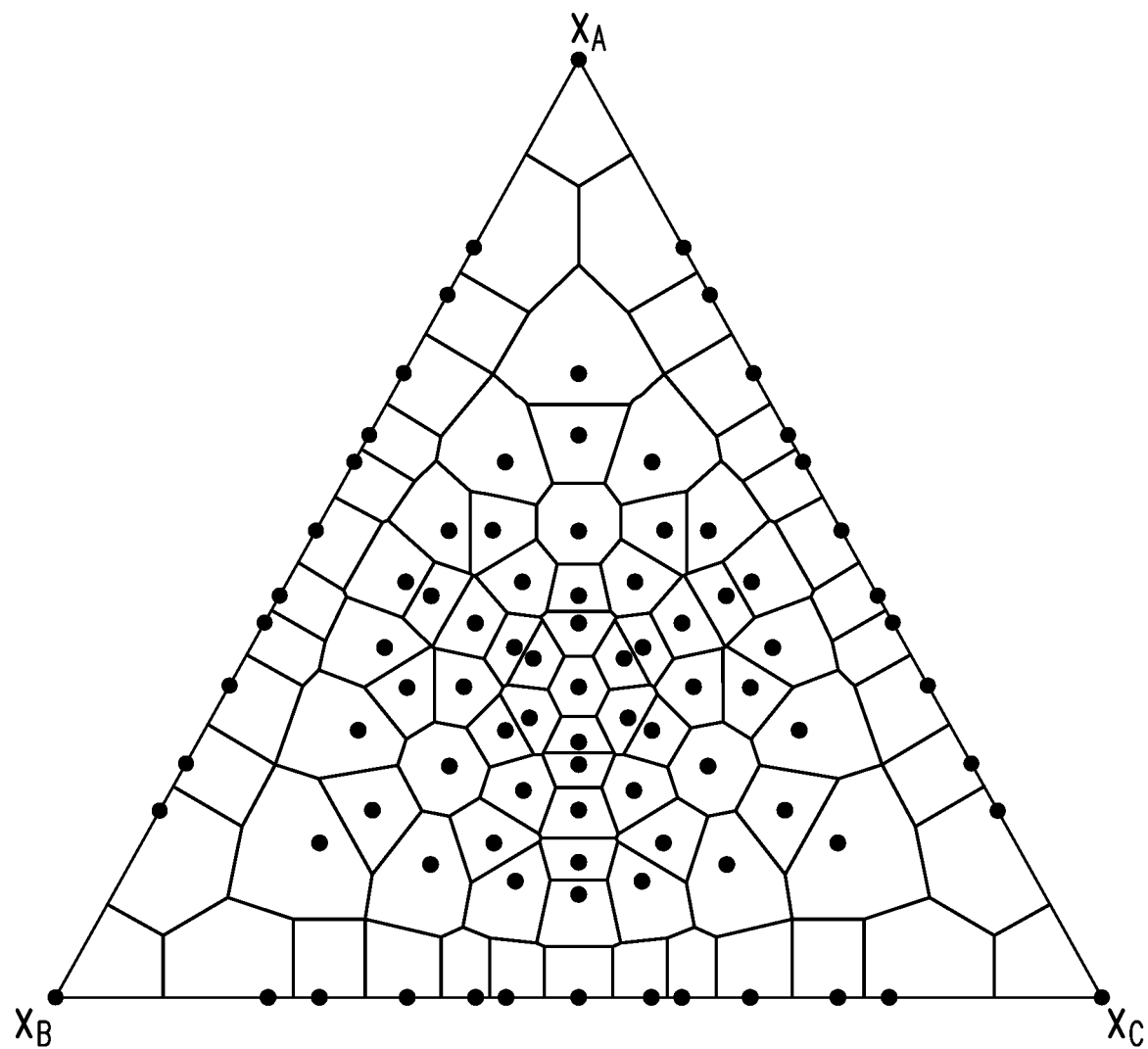
FIG. 13b is a ternary mass fraction composition diagram divided into Voronoi cells illustrating the nearest neighbor compositions.

Such stratification of the composition space by physiological measurement or biomarker result can be described exactly mathematically by the division of the relevant composition space into regions called cells. The cells represent the region of the composition space for which the enclosed lattice point represents the closest accessible composition to a given target composition based on the measurement. For example, if body weight is the biomarker of interest and the patient population is divided into groups based on intervals of 10 kg such that patients within the same 10 kg band will all receive the same dose, patients in the next 10 kg band will receive a higher dose of one or both of the drugs in the combination, then in composition space the target dose for patients within the first 10 kg band will be the composition lattice point for the cell corresponding to their biomarker measurement. The target dose for the next group will be closer to an adjacent composition lattice point and will therefore lie within that point's cell. The cell boundaries are the loci of compositions, which are equidistant from two lattice points. The lattice points represent the doses that the device can be configured for and so depending on their body weight, individual patients would receive a version of the device configured to target the lattice point for the composition closest to their target dose. FIG. 12 illustrates an example of such a sub-division of a 2-dimensional composition space. In FIG. 12, the patient population is stratified by 10 kg body mass increments ranging from 50 kg to 100 kg, resulting in rectangular cells. Patients <50 kg body mass receive a flat 20 mg dose of each drug. For each 10 kg increment over 50 kg, patients receive an extra 10 mg of both A and B in this case, though it should be understood that in embodiments one or more drug doses may remain fixed independently of the biomarker measurement. In FIG. 12, vectors represent the composition increments. The line is diagonal in this case because both drugs have doses dependent on the biomarker measurement. If A or B were fixed doses then the composition increments would respectively trace vertical or horizontal lines in the composition plane. For patients with body mass between two lattice points, they receive a device configured for the composition lattice point for the cell which their body mass lies in. FIG. 13a is a projection of variable compositions in 3-dimensional ternary composition space. The solid vectors represent the composition increments due to the biomarker measurement passing through the ternary composition lattice. FIG. 13b is a Voronoi tessellation of the ternary simplex diagram for mass fractions.

Mathematically the division of the composition space into cells defined by lattice points is a result of a Delaunay triangulation of the composition space and the cells into which the space is divided are called Voronoi cells. Several algorithms for the partitioning of general rectilinear spaces based on the Delaunay triangulation of a set of points are known to the person skilled in the art, for example the packages GEOMETRY and DELDIR for the R-programming language which provide respectively the functions TETRAMESH and DELDIR which respectively return the Voronoi tessellation of the set of points in two and three dimensional spaces.

Geometrically, the region of the composition space that is accessible by a device constructed in accordance with the present invention is defined as the convex hull of the extremal points of the space. The convex hull can be computed using the QHULL library which is known to the person skilled in the art and is implemented in the R-programming language GEOMETRY package function CONVHULLN.

Because of the possibility to configure a device constructed according to the present invention for the specific therapeutic requirements of individual patients P a personalized medicine system 100 based on the present invention can be conceived. In such a system, at the point of diagnosis 102 such as a physician consultation, based on the results of a biomarker measurement, an order 104 for a specific configuration of a device constructed in accordance with the present invention would be raised in an electronic prescription system.

Figure 14:
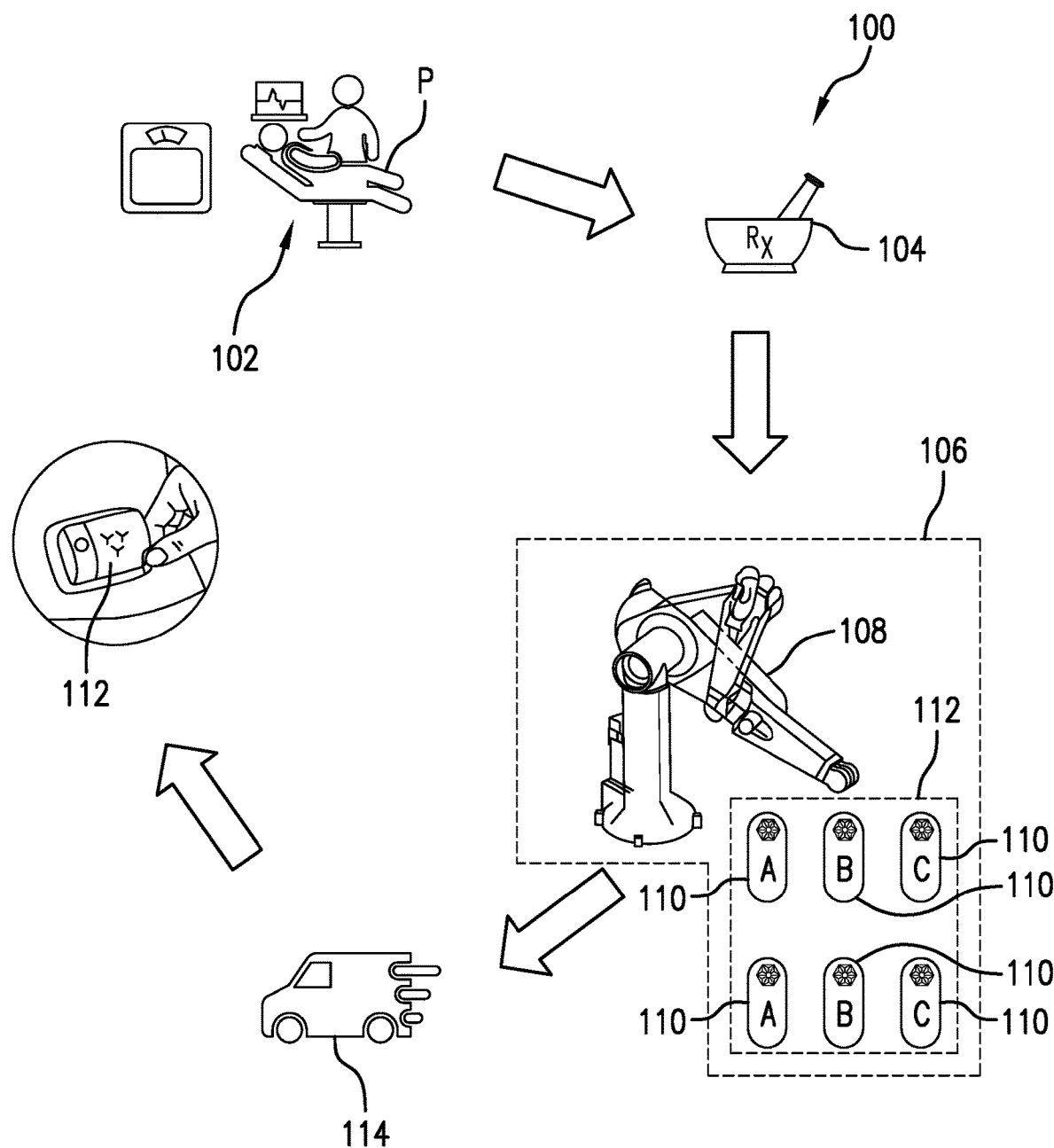
FIG. 14 is a schematic of a manufacturing system for a biomarker based dosing based on devices constructed according to the combinatorial principle.

The order 104 would be received at an advanced manufacturing facility 106 constructed for the automated configuration of devices constructed according to the present invention. The facility 106 may use robotic technology 108 to pick and place integral dosage units (vials, cartridges, capsules) 110 and configure them into drug delivery devices 112 on a per prescription basis, package and label them and ship 114 to the patient, physician or pharmacy. FIG. 14 illustrates schematically how such a personalized medicine system 100 based on the present invention could be configured.

The present invention has broad applicability. The present invention can be incorporated within drug delivery devices as well as the equipment and systems used to manufacture, assemble and distribute them. The present invention can be used by devices, which combine and deliver drug to the patient or by devices which combine and transfer the drug to a separate delivery device. The present invention is compatible with all the commonly used methods and devices used for drug delivery, such as IV, needle syringes, auto-injectors and wearable pumps. The present invention is compatible with all commonly available primary drug containers (such as vials, syringes and cartridges) as well as custom containers. The present invention can be used to combine integral unit doses of drug, which are all in liquid form, or a combination of drugs and diluent in liquid and dry form. The present invention is compatible with all commonly used power sources for devices, such as manual, electrical (AC or DC), magnetic, pressurized gas, vacuum, etc. The present invention can be used by devices, which are monolithic or modular, using disposable and/or reusable components. The present invention is compatible with devices that are final assembled at the point-of-care, at the pharmacy, or at any point within the manufacturing supply chain.

Figure 15:
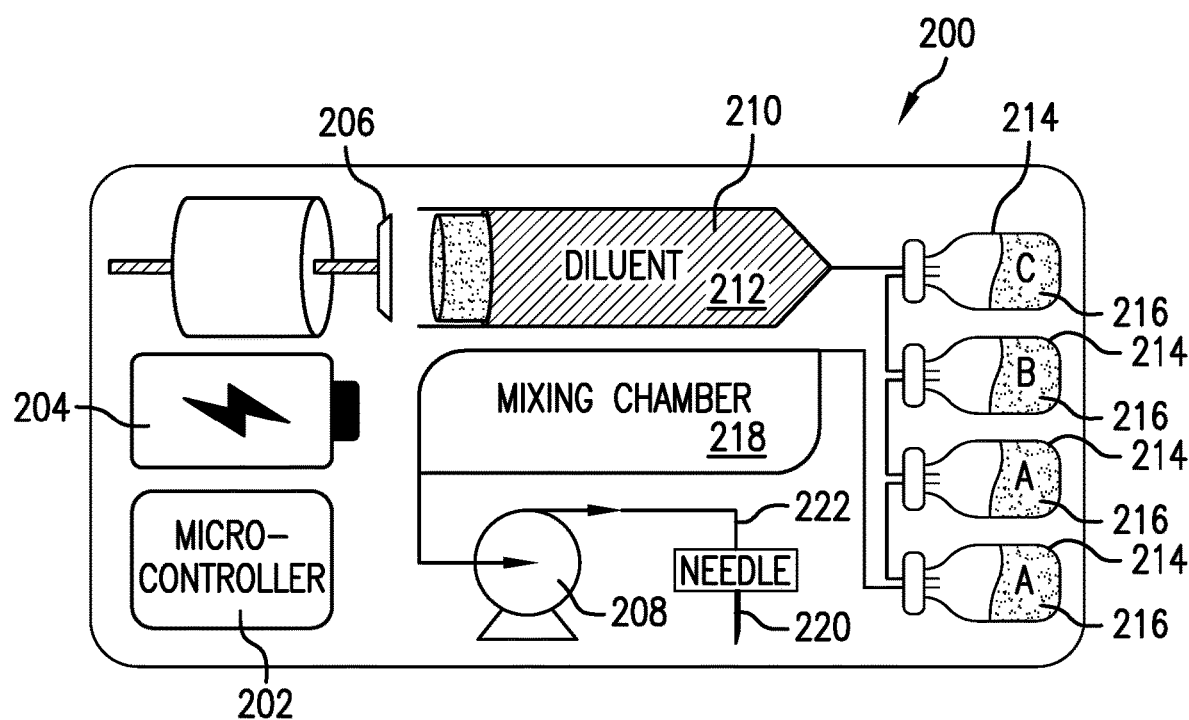
FIGS. 15 and 15b are schematics of a monolithic body worn device comprising a liquid diluent reservoir a mixing chamber and four nests for drugs A, B, C provided in powder form.
Figure 15B:
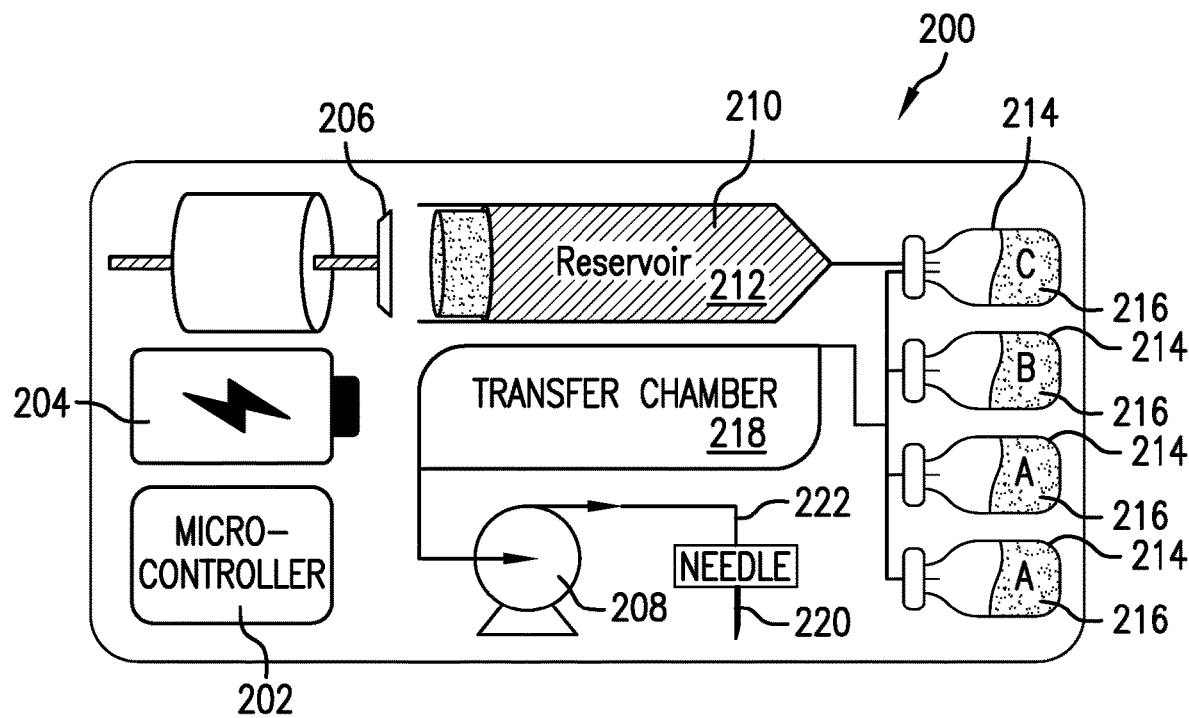

The drug delivery device 200 shown in FIGS. 15 and 15b is but one example of the present invention. FIG. 15 shows a container (e.g., vial) arrangement in series, while FIG. 15b shows a container (e.g., vial) arrangement in parallel. It is a monolithic wearable device, which reconstitutes integral unit doses of dry form drug with a liquid diluent and delivers the resulting combination into tissue. The device 200 is comprised of an electronic micro-controller 202 for the control of the reconstitution and delivery processes, a power source, mechanisms to reconstitute (e.g., driven plunger 206) and deliver (e.g., pump 208) the drug combination, a reservoir 210 holding liquid diluent 212, containers 214 holding drugs 216 in dry form, an integral mixing chamber 218, and an injection needle 220 at a common outlet 222 of the device 200. The entire device 200 can be assembled within the manufacturing supply chain and supplied to the point-of care ready to use. The entire device 200 can be worn on the skin by a patient, using an adhesive patch. The entire device 200 can be disposable. In embodiments the liquid diluent reservoir 210 may contain a drug solution.

Figure 16:
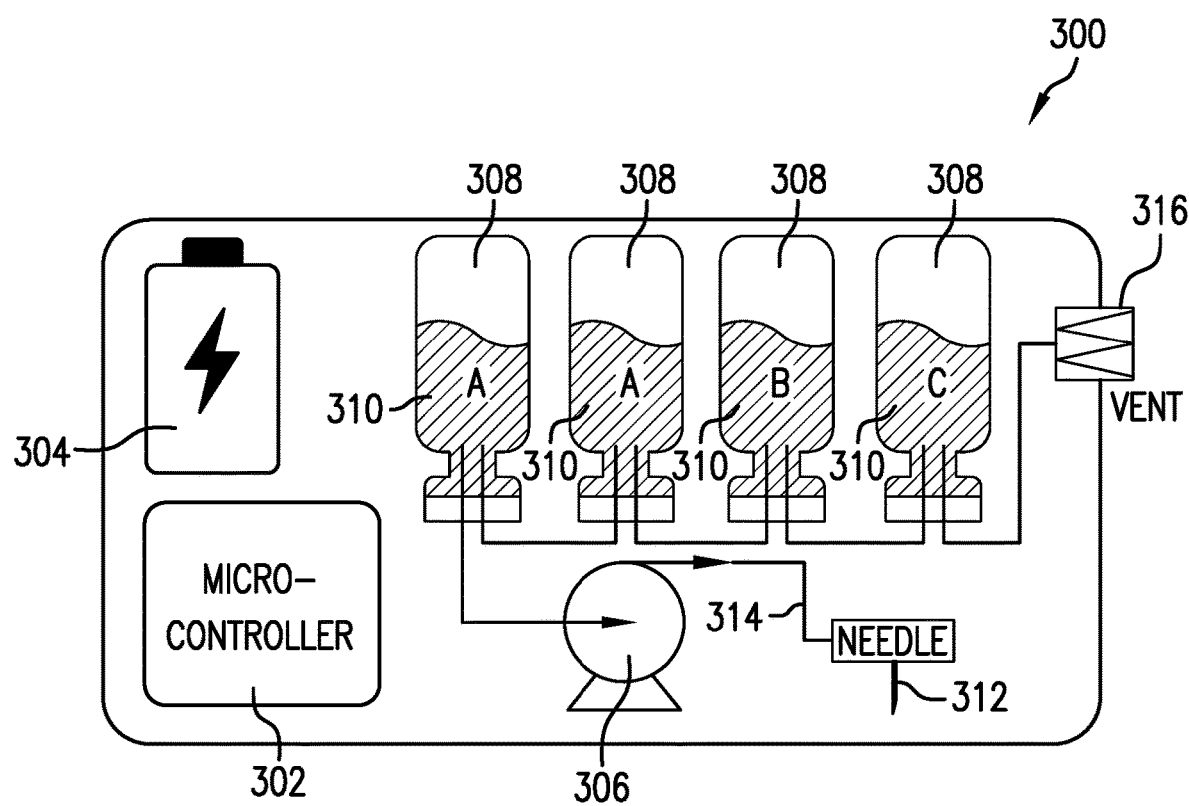
FIGS. 16 and 16b are schematics of a monolithic body worn device comprising nests four nests for liquid filled vials of drugs A, B, C.
Figure 16B:
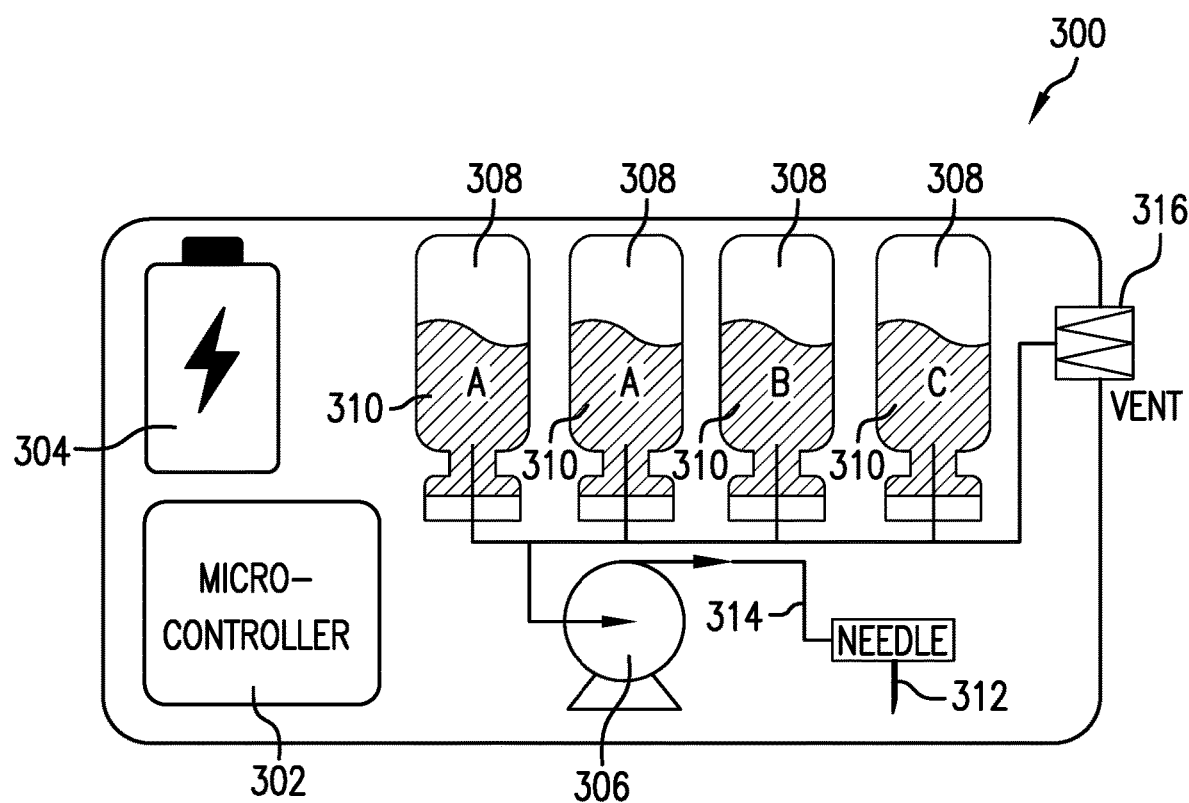

The drug delivery device 300 shown in FIGS. 16 and 16b is but one example of the present invention. FIG. 16 shows a container (e.g., vial) arrangement in series, while FIG. 16b shows a container (e.g., vial) arrangement in parallel. It is a monolithic wearable device, which mixes integral unit doses of liquid drug and delivers the resulting combination into tissue. The device 300 is comprised of an electronic micro-controller 302 for the control of the mixing and delivery processes, a power source 304, mechanisms to mix and deliver (e.g., pump 306) the drug combination, containers 308 holding drugs 310 in liquid form, and an injection needle 312 at a common outlet 314 of the device 300. The entire device 300 can be assembled within the manufacturing supply chain and supplied to the point-of care ready to use. The entire device 300 can be worn on skin, using an adhesive patch. The entire device 300 can be disposable. In embodiments the device 300 may incorporate a micro-filtered vent 316 for the equalization of pressure during mixing and delivery.

Figure 17:
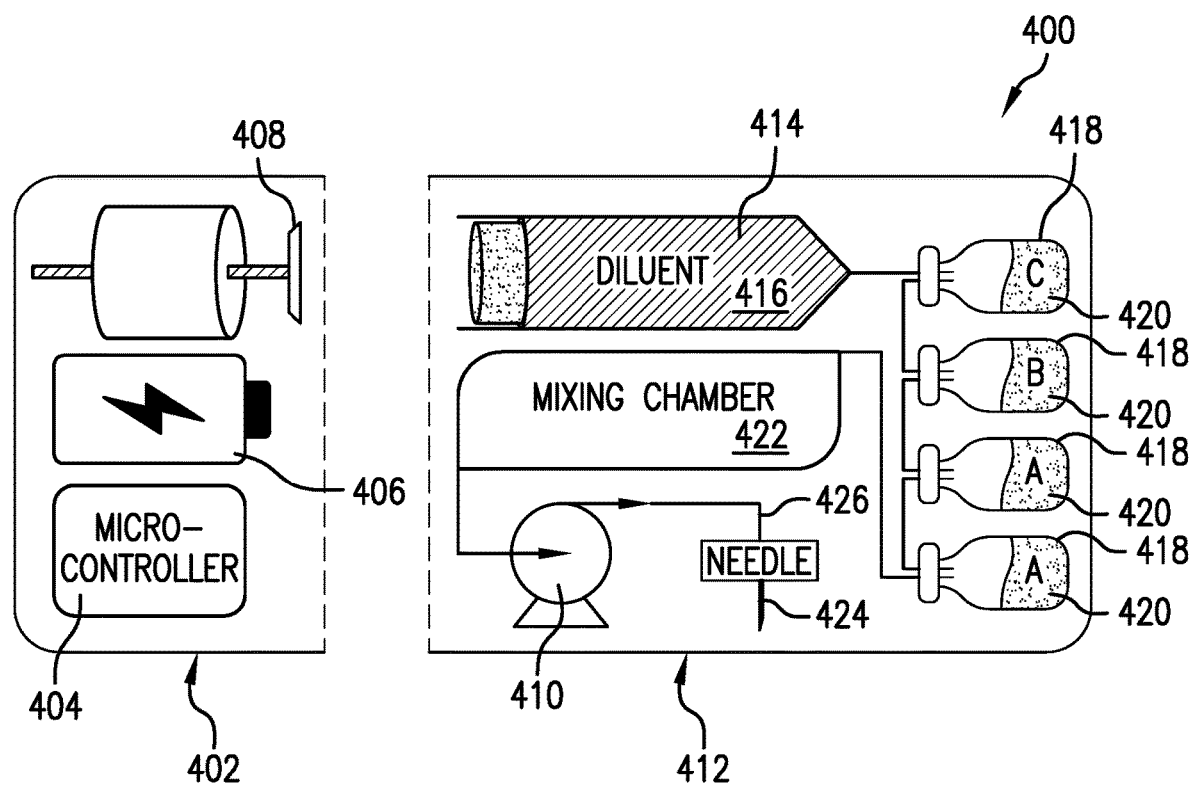
FIGS. 17 and 17b are schematics of a modular body worn device comprising a liquid diluent reservoir a mixing chamber and four nests for drugs A, B, C provided in powder form.
Figure 17B:
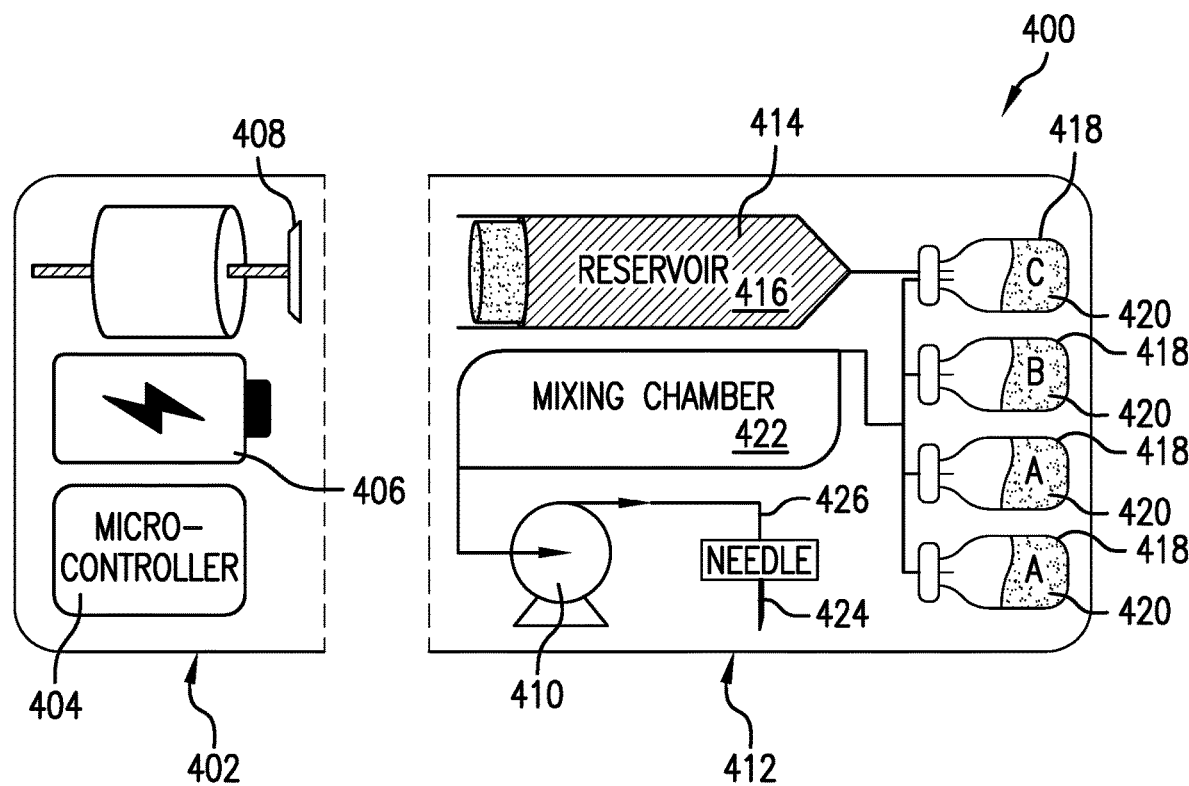

The drug delivery device 400 shown in FIGS. 17 and 17b is but one example of the present invention. FIG. 17 shows a container (e.g., vial) arrangement in series, while FIG. 17b shows a container (e.g., vial) arrangement in parallel. It is a modular wearable device, which reconstitutes integral unit doses of dry form drug with a liquid diluent and delivers the resulting combination into tissue. The device 400 is comprised of a drive module 402 (including an electronic micro-controller 404 for the control of the reconstitution and delivery processes, a power source 406, and mechanisms to reconstitute (e.g., driven plunger 408) and deliver (e.g., pump 410) the drug combination) and a separate drug module 412 (consisting of a reservoir 414 holding liquid diluent 416, containers 418 holding drugs 420 in dry form, an integral mixing chamber 422, and an injection needle 424 at a common outlet 426 of the device 400). The drive module 402 and drug module 412 can each be assembled independently within the manufacturing supply chain and then connected to each other at the point-of-care prior to use. The drive module 402 can be reusable and the drug module 412 can be single-use or reusable. The entire device 400 can be worn on skin, using an adhesive patch. In embodiments the liquid diluent reservoir may contain a drug solution.

Figure 18:
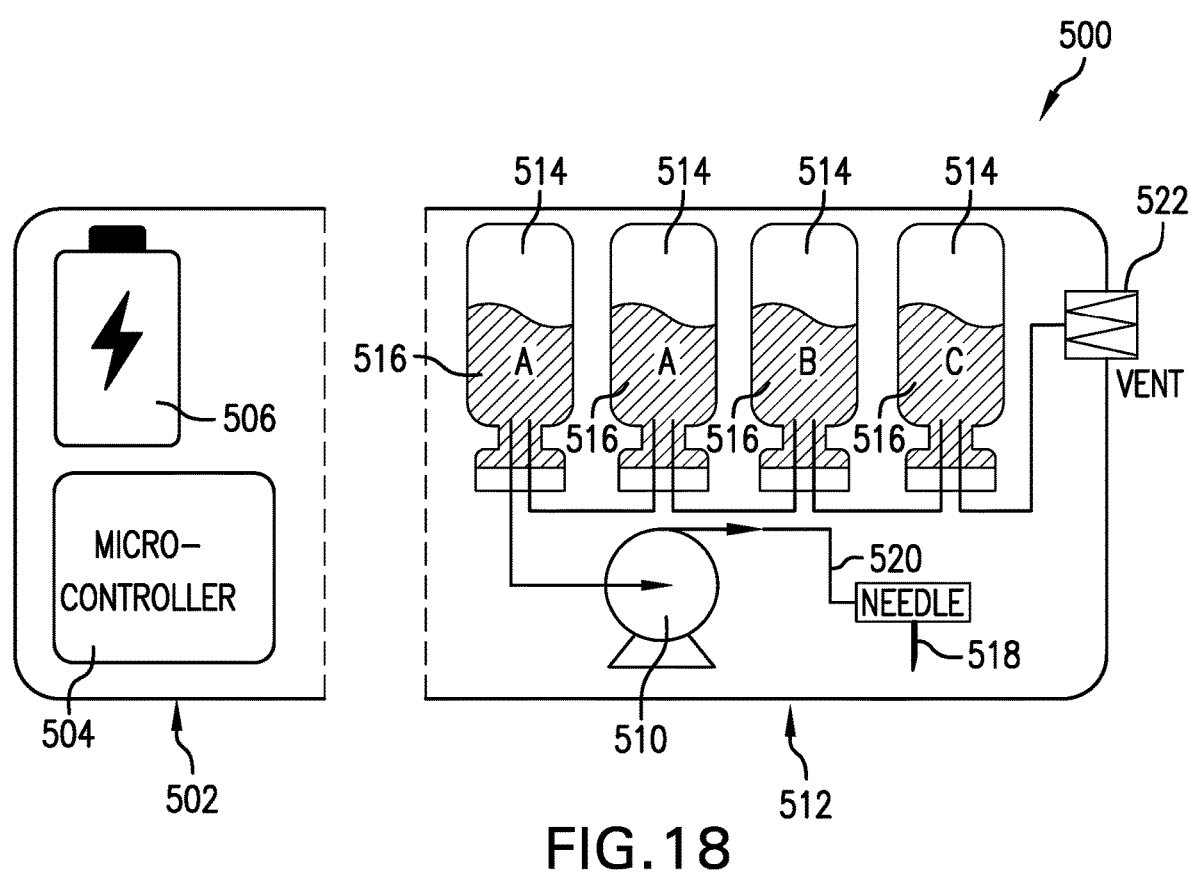
FIGS. 18 and 18b are schematics of a modular body worn device comprising nests four nests for liquid filled vials of drugs A, B, C.
Figure 18B:
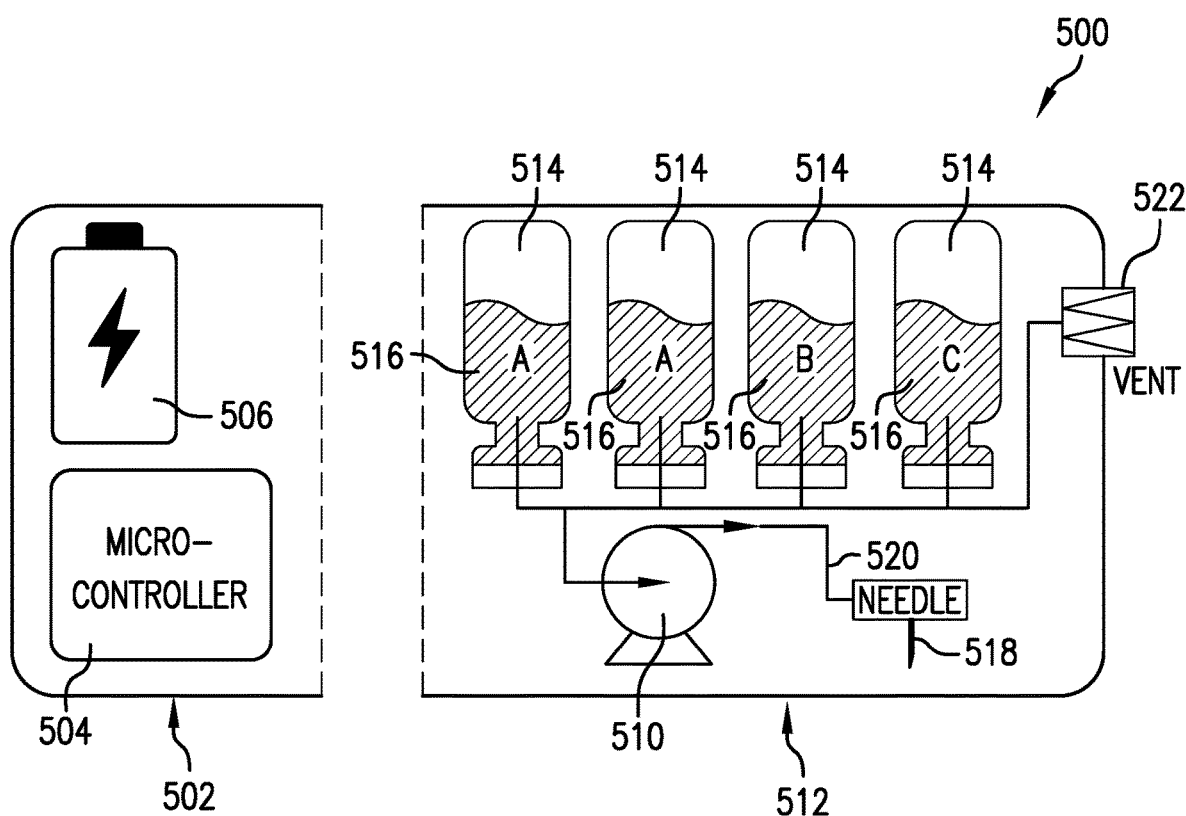

The drug delivery device 500 shown in FIGS. 18 and 18b is but one example of the present invention. FIG. 18 shows a container (e.g., vial) arrangement in series, while FIG. 18b shows a container (e.g., vial) arrangement in parallel. It is a modular wearable device, which reconstitutes integral unit doses of liquid drug and delivers the resulting combination into tissue. The device 500 is comprised of a drive module 502 (including an electronic micro-controller 504 for the control of the mixing and delivery processes, and a power source 506) and a separate drug module 512 (consisting of mechanisms to reconstitute and deliver (e.g., pump 510) the drug combination, containers 514 holding drugs 516 in liquid form, and an injection needle 518 at a common outlet 520 of the device 500). The drive module 502 and drug module 512 can each be assembled independently within the manufacturing supply chain and then connected to each other at the point-of-care prior to use. The drive module 502 can be reusable and the drug module 512 can be single-use or reusable. The entire device 500 can be worn on skin, using an adhesive patch. In embodiments the device 500 may incorporate a micro-filtered vent 522 for the equalization of pressure during mixing and delivery.

Figure 19:
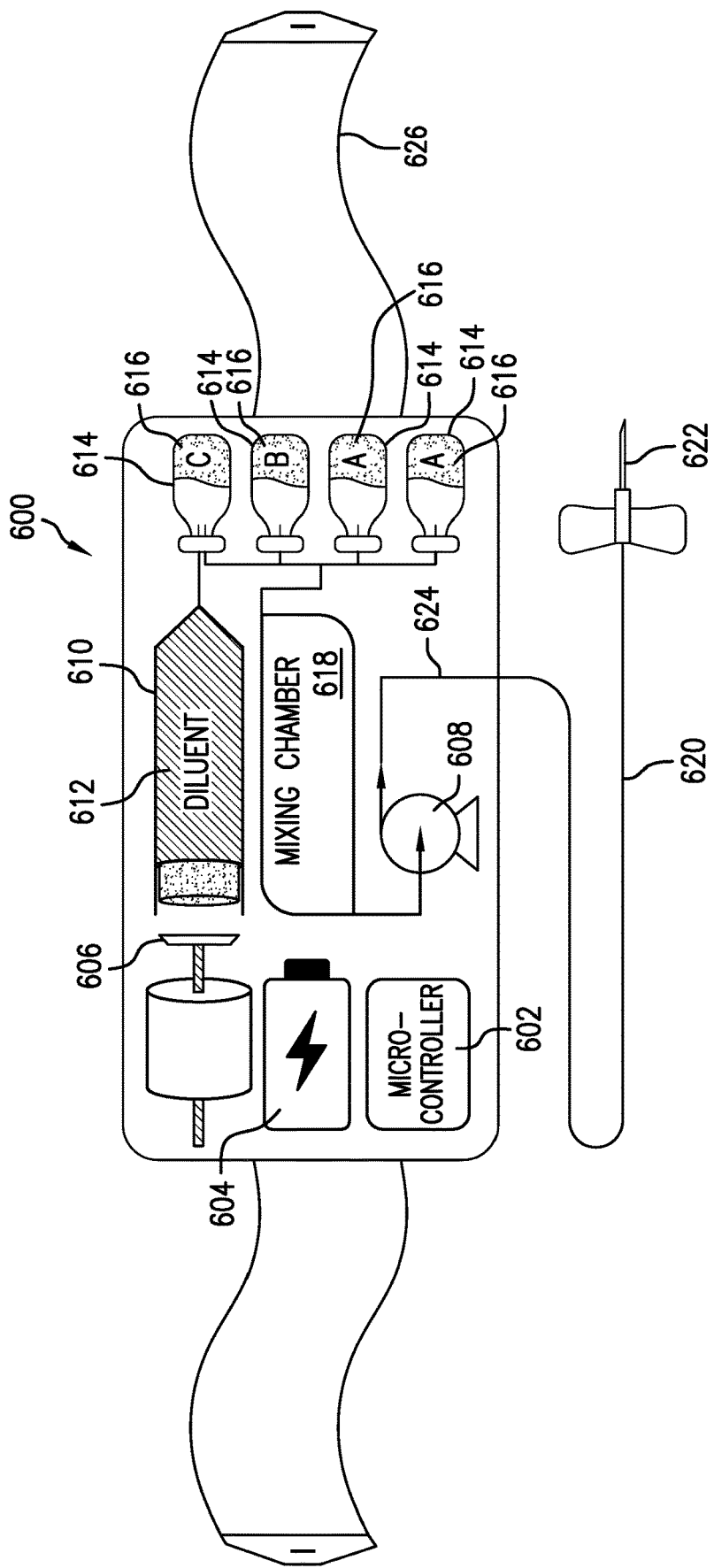
FIGS. 19 and 19b are schematics of the device of FIG. 15 configured for belt worn use.
Figure 19B:
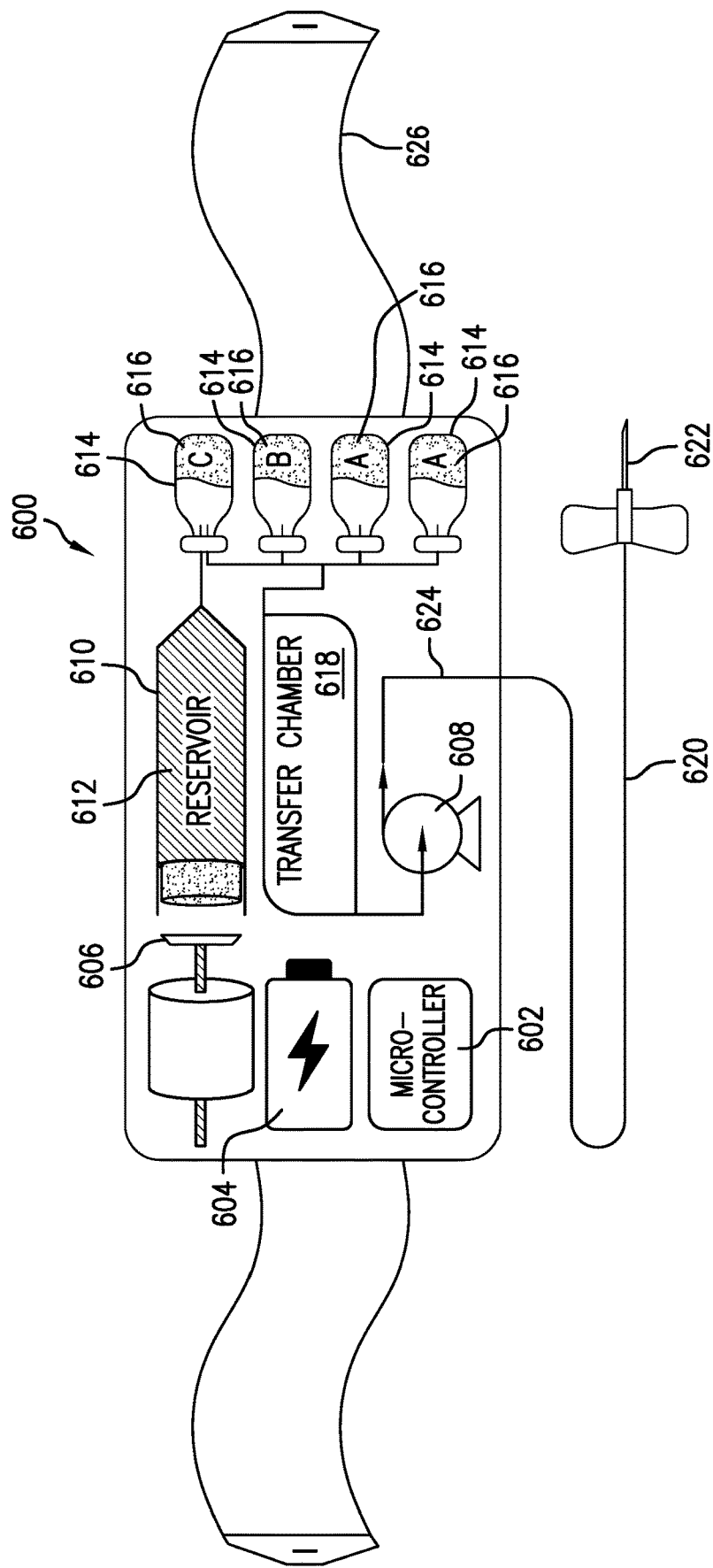

The drug delivery device 600 shown in FIGS. 19 and 19b is but one example of the present invention. FIG. 19 shows a container (e.g., vial) arrangement in series, while FIG. 19b shows a container (e.g., vial) arrangement in parallel. It is a modular wearable device, which reconstitutes integral unit doses of dry form drug with a liquid diluent and delivers the resulting combination into tissue. The device 600 is comprised of an electronic micro-controller 602 for the control of the reconstitution and delivery processes, a power source 604, mechanisms to reconstitute (e.g., driven plunger 606) and deliver (e.g., pump 608) the drug combination, a reservoir 610 holding liquid diluent 612, containers 614 holding drugs 616 in dry form, an integral mixing chamber 618, tubing 620 with injection needle 622 (e.g., butterfly needle) at a common outlet 624 of the device 600, and a mounting belt 626. The various components of the device 600 can be manufactured within the supply chain and then final assembled at the point-of-care prior to use. The mounting belt 626 supports the device 600 on the patient body and can be reusable. The rest of the components can be disposable. In embodiments the liquid diluent reservoir 610 may contain a drug solution.

Figure 20:
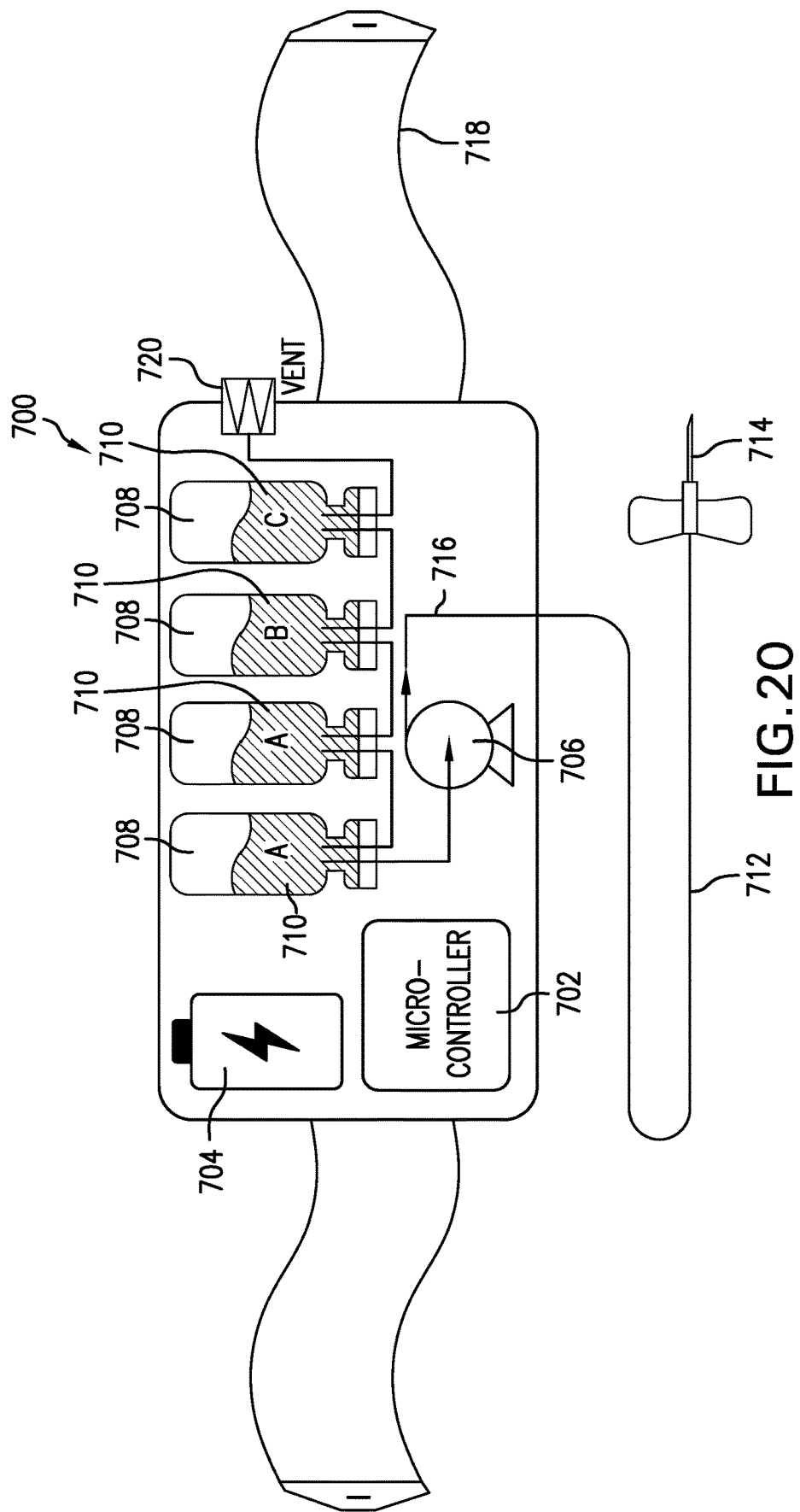
FIGS. 20 and 20b are schematics of the device of FIG. 16 configured for belt worn use.
Figure 20B:
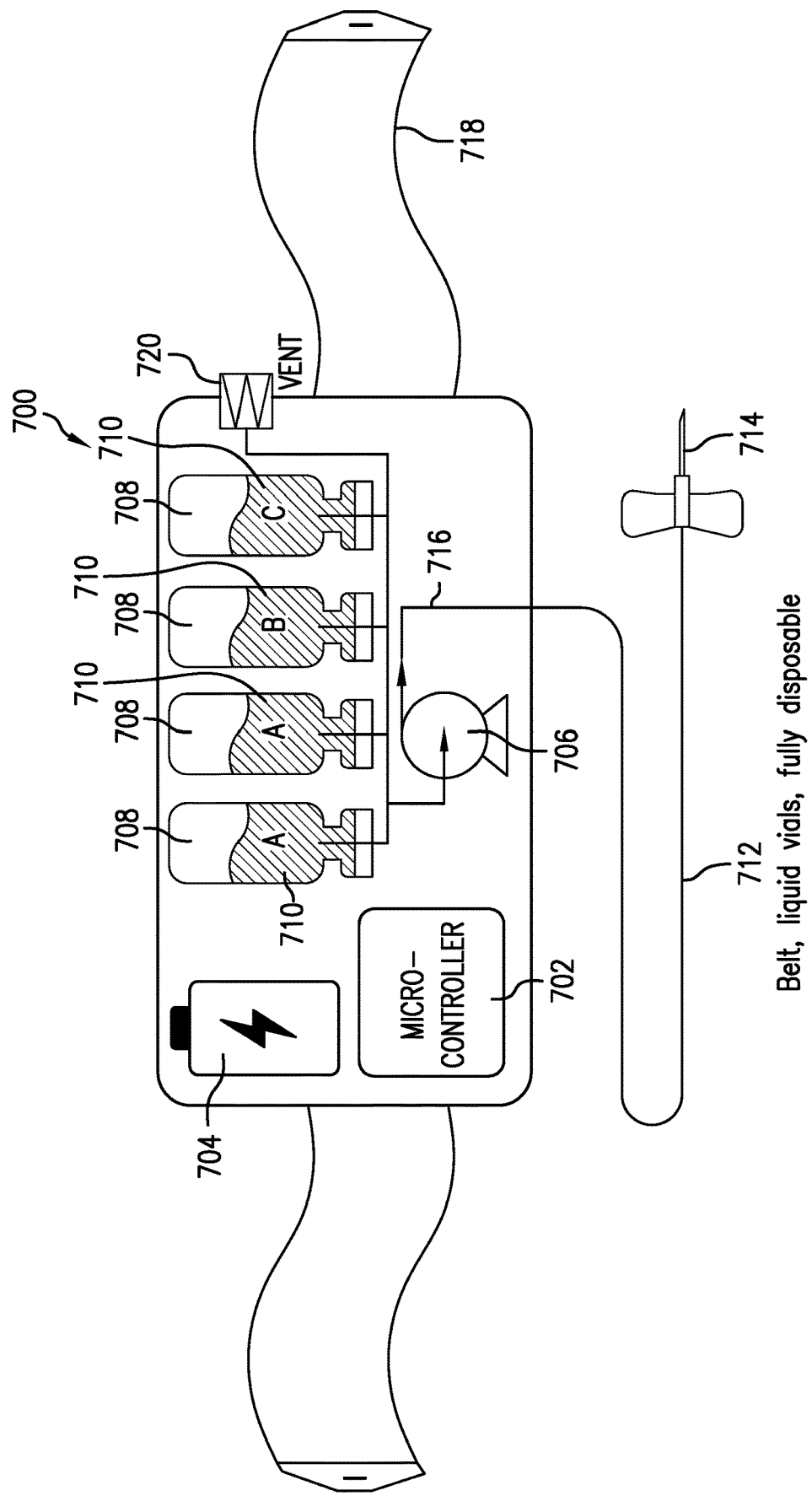

The drug delivery device 700 shown in FIGS. 20 and 20b is but one example of the present invention. FIG. 20 shows a container (e.g., vial) arrangement in series, while FIG. 20b shows a container (e.g., vial) arrangement in parallel. It is a modular wearable device, which reconstitutes integral unit doses of liquid drug and delivers the resulting combination into tissue. The device 700 is comprised of an electronic micro-controller 702 for the control of the reconstitution and delivery processes, a power source 704, mechanisms to mix and deliver (e.g., pump 706) the drug combination, containers 708 holding drugs 710 in liquid form, tubing 712 with injection needle 714 (e.g., butterfly needle) at a common outlet 716 of the device 700, and a mounting belt 718. The various components of the device 700 can be manufactured within the supply chain and then final assembled at the point-of-care prior to use. The mounting belt 718 supports the device 700 on the patient body and can be reusable. The rest of the components can be disposable. In embodiments the device 700 may incorporate a micro-filtered vent 720 for the equalization of pressure during mixing and delivery.

Figure 21:
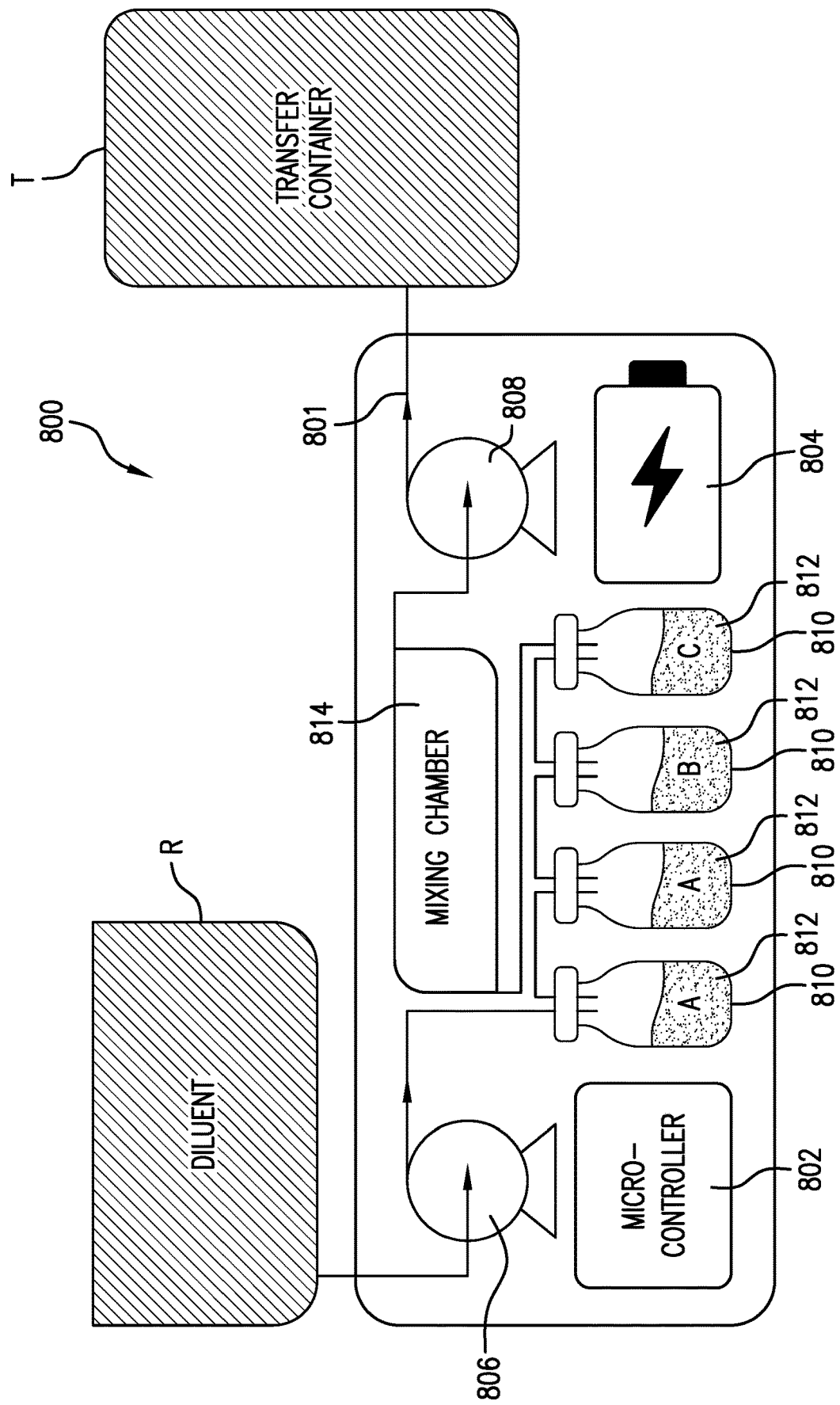

The drug preparation device 800 shown in FIGS. 21 and 21b is but one example of the present invention. FIG. 21 shows a container (e.g., vial) arrangement in series, while FIG. 21b shows a container (e.g., vial) arrangement in parallel. It is a modular device, which reconstitutes integral unit doses of dry form drug with a liquid diluent and transfers the resulting combination into a transfer container T, via a common outlet 801, which then can be used with a separate delivery system such as an intravenous infusion bag, syringe/needle, auto-injector, wearable pump, etc. The device 800 is comprised of an electronic micro-controller 802 for the control of the reconstitution and delivery processes, a power source 804, mechanisms to reconstitute (e.g., diluent pump 806) and transfer (e.g., delivery pump 808) the drug combination, containers 810 holding drugs 812 in dry form, and a mixing chamber 814. The various components of the device 800 can be manufactured within the supply chain and then final assembled at the point-of-care along with a standard reservoir of liquid diluent R (such as a sterile water-for-injection vial or intravenous infusion bag) and a standard transfer container (such as a disposable syringe) prior to use. In embodiments the liquid diluent reservoir R may contain a drug solution.

Figure 21C:
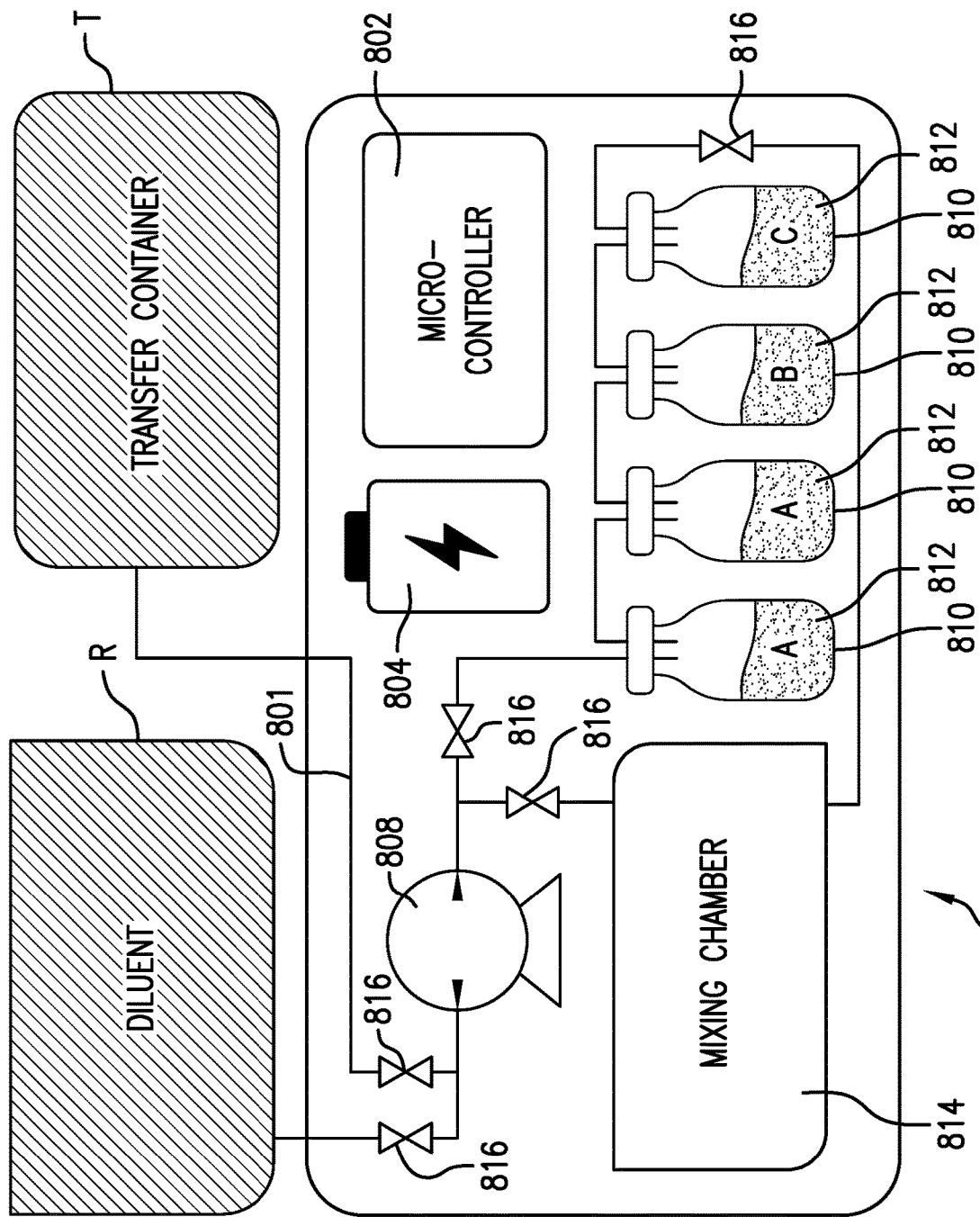
Figure 21D:
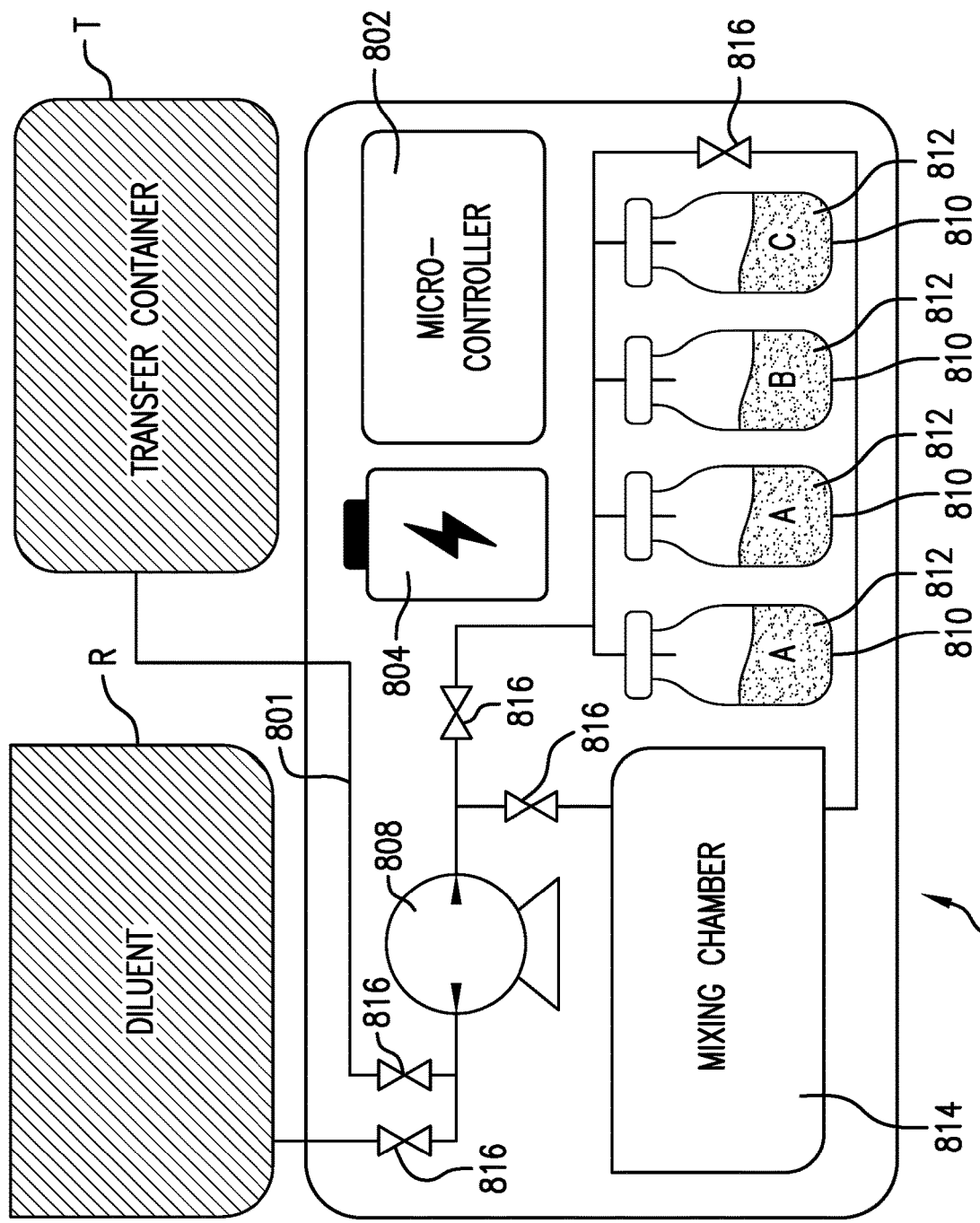

As shown in FIGS. 21c and 21d, the device 800 may be modified to have a single pump, e.g., the delivery pump 800, perform the functions of the diluent pump 806 and the delivery pump 808. In this arrangement, the delivery pump 800 may be configured as a bi-directional pump configured to pump the diluent from the liquid diluent reservoir R to the containers 810 and, separately, be reversed to draw the drugs 812 from the containers 810 to the common outlet 801, including through the mixing chamber 814 if provided (the mixing chamber 814 can be omitted). Control valving 816 may be provided as needed to control the flow to and from the liquid diluent reservoir R, the delivery pump 808, the mixing chamber 814, the containers 810, and the common outlet 801.

Figure 21E:
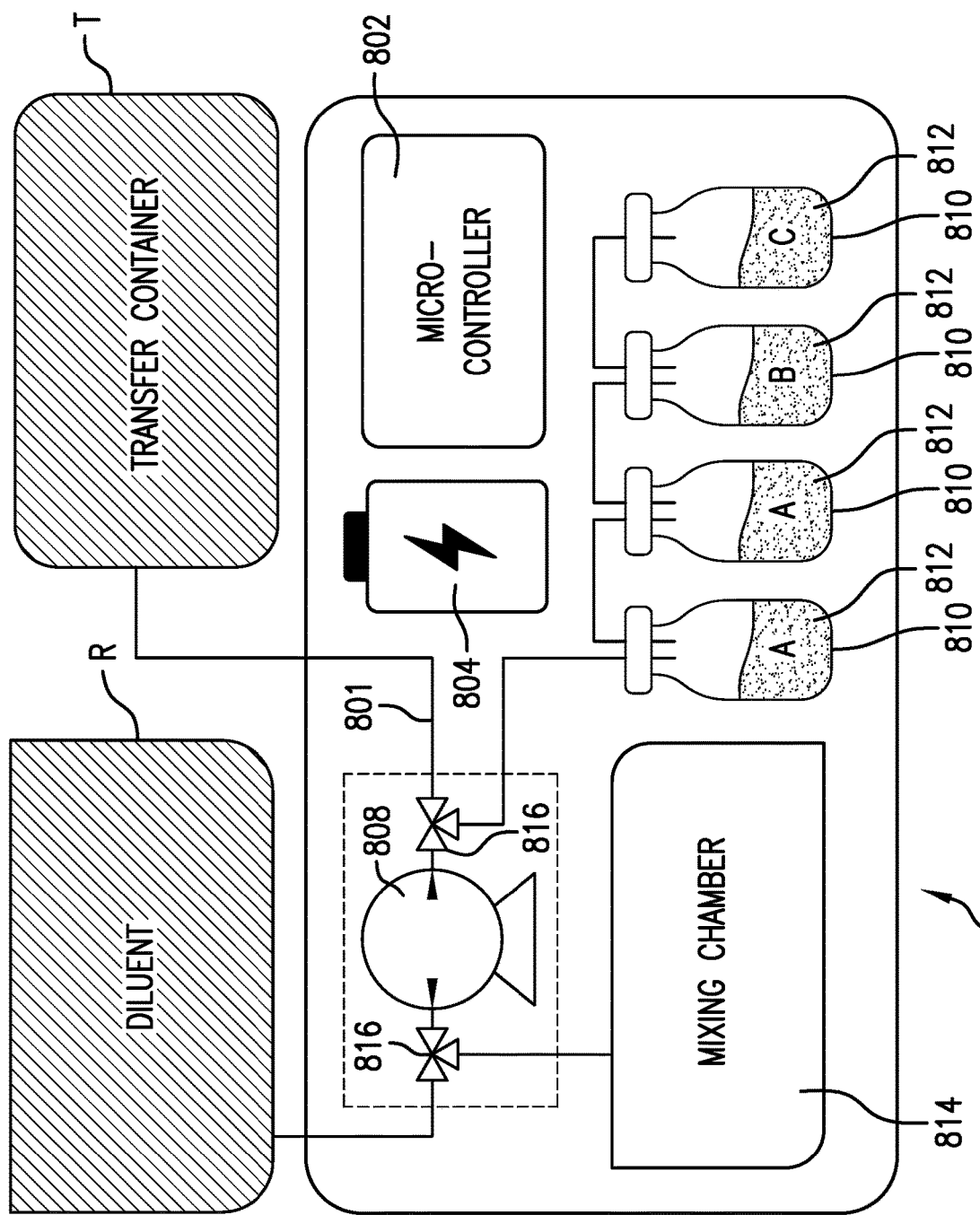
Figure 21F:
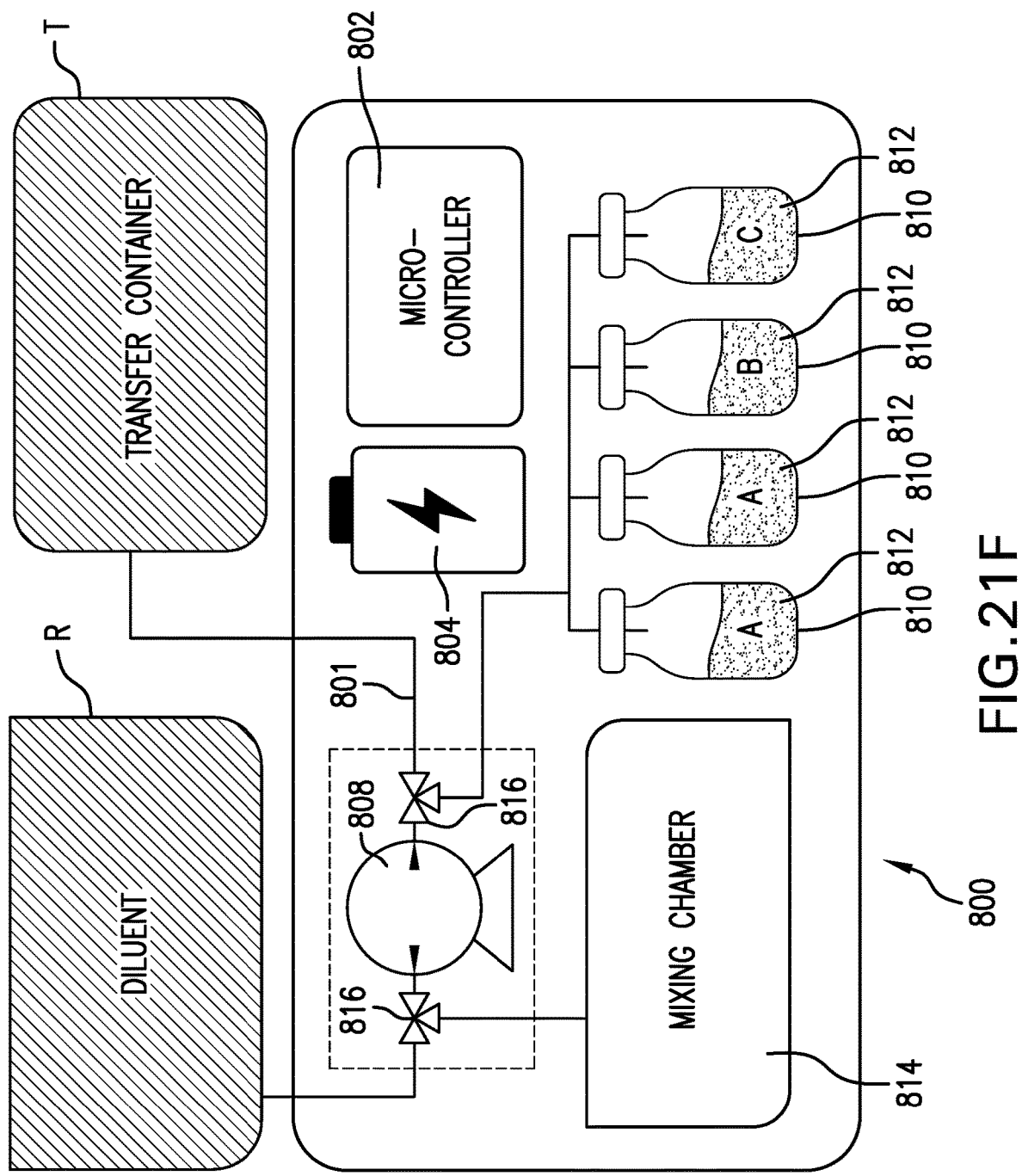

As shown in FIGS. 21e and 21f, the device 800 may be further modified to have a single pump, e.g., the delivery pump 800, perform the functions of the diluent pump 806 and the delivery pump 808. In this arrangement, the delivery pump 800 may be configured as a bi-directional pump configured to: pump the diluent from the liquid diluent reservoir R to the containers 810; then, be reversed to draw the drugs 812 from the containers 810 to the mixing chamber 814; and, then be reversed again to draw the drugs 812 from the mixing chamber 814 and urge the extracted drugs 812 to the common outlet 801. Control valving 816 may be provided as needed to control the flow to and from the liquid diluent reservoir R, the delivery pump 808, the mixing chamber 814, the containers 810, and the common outlet 801.

Figure 22:
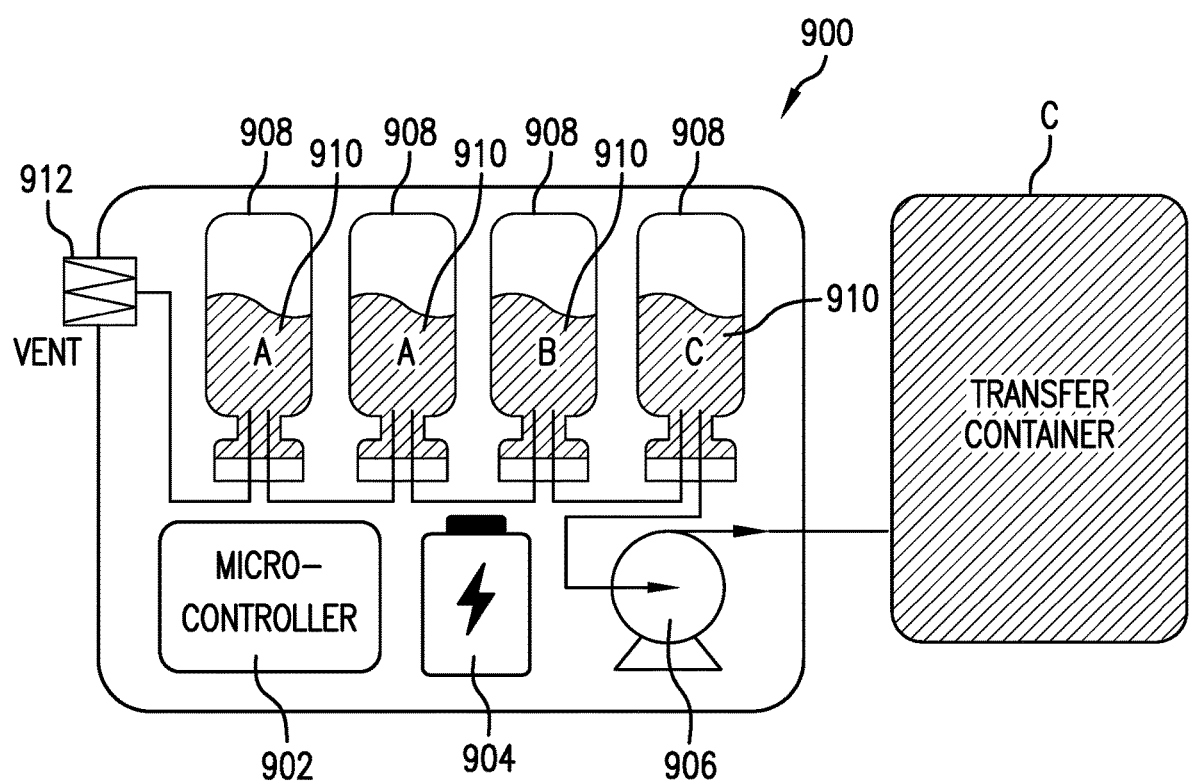
FIGS. 22 and 22b are schematics of a device comprising four nests for receipt of liquid drugs A, B, C with external configured for the reconstitution of the drugs A, B, C using the diluent and subsequent transfer of the final composition to an external transfer container ready for further transfer to another reservoir e.g. an intravenous infusion bag or other administration device for administration to the patient.
Figure 22B:
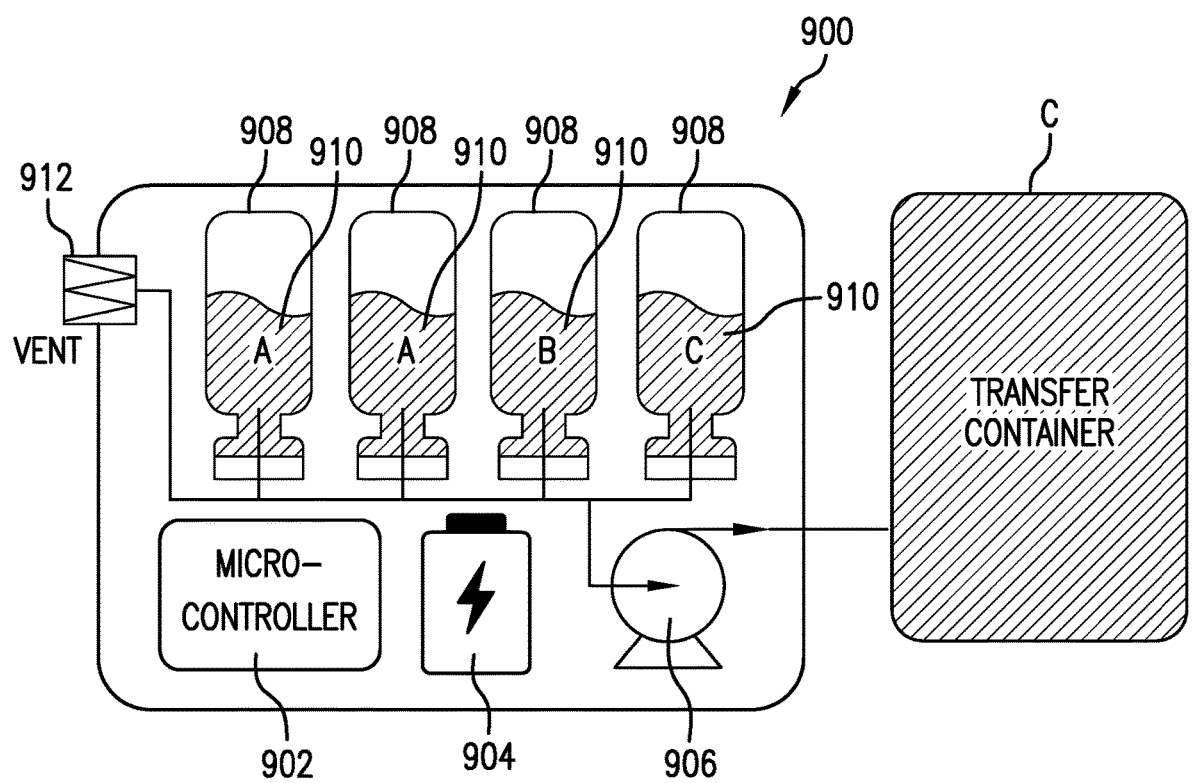

The drug preparation device 900 shown in FIGS. 22 and 22b is but one example of the present invention. FIG. 22 shows a container (e.g., vial) arrangement in series, while FIG. 22b shows a container (e.g., vial) arrangement in parallel. It is a modular device, which mixes integral unit doses of liquid drug and transfers the resulting combination into a transfer container, which then can be used with a separate delivery system such as an intravenous infusion bag, syringe/needle, auto-injector, wearable pump, etc. The device 900 is comprised of an electronic micro-controller 902 for the control of the reconstitution and delivery processes, a power source 904, mechanisms to mix and transfer (e.g., pump 906) the drug combination, and containers 908 holding drugs 910 in liquid form. The various components of the device 900 can be manufactured within the supply chain and then final assembled at the point-of-care along with a standard transfer container C (such as a disposable syringe) prior to use. In embodiments the device 900 may incorporate a micro-filtered vent 912 for the equalization of pressure during mixing and delivery.

Figure 23:
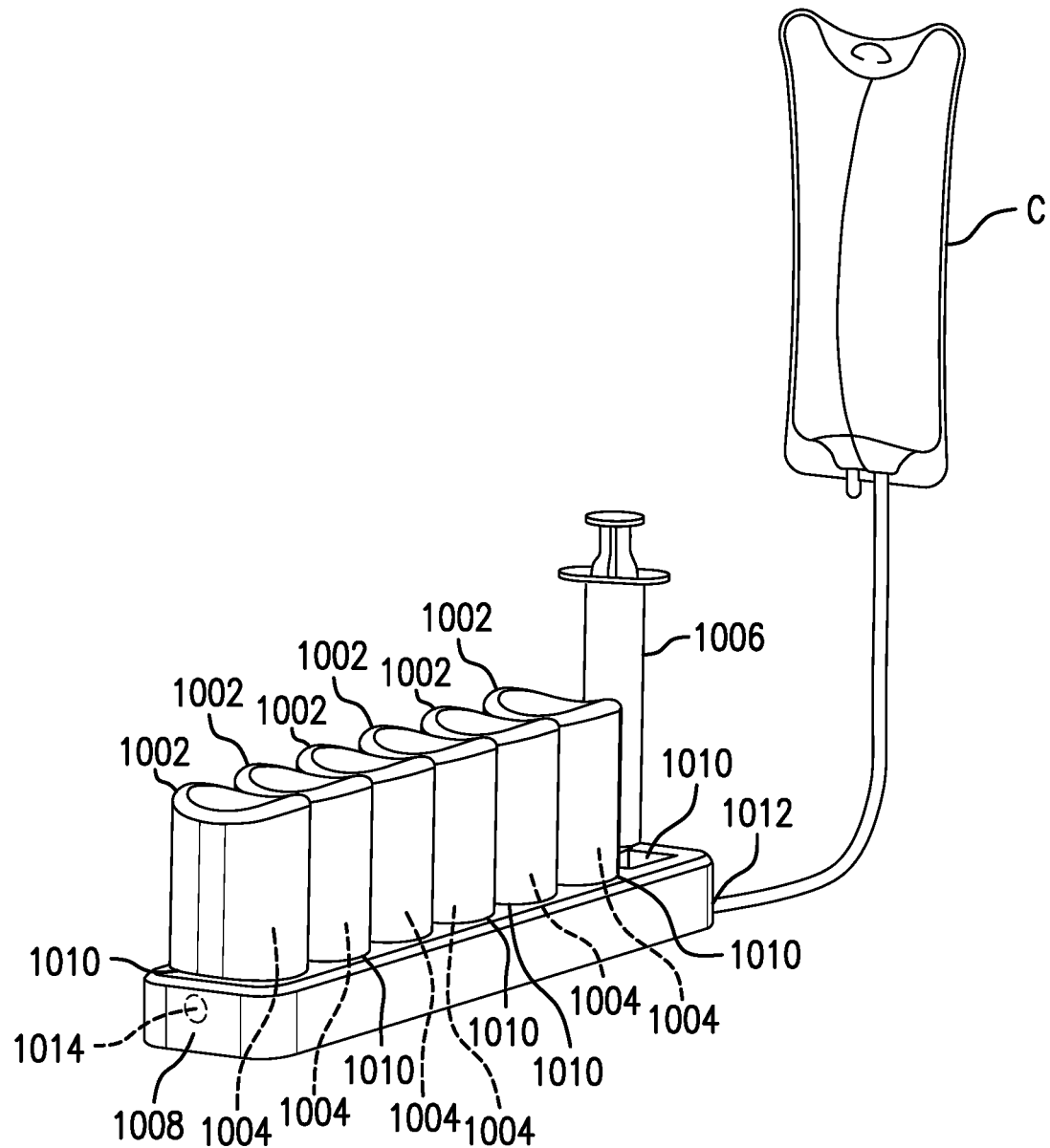
FIG. 23 is a schematic of a device with six nests for configurable receipt of liquid vials of different drugs connected in series. The device comprises a syringe and valve assembly for the manually pumped transfer of the contents of the vials to an external reservoir, e.g., an intravenous infusion bag. The end of the series tubing line is fitted with a micro-filtered vent for pressure equalization.
Figure 24:
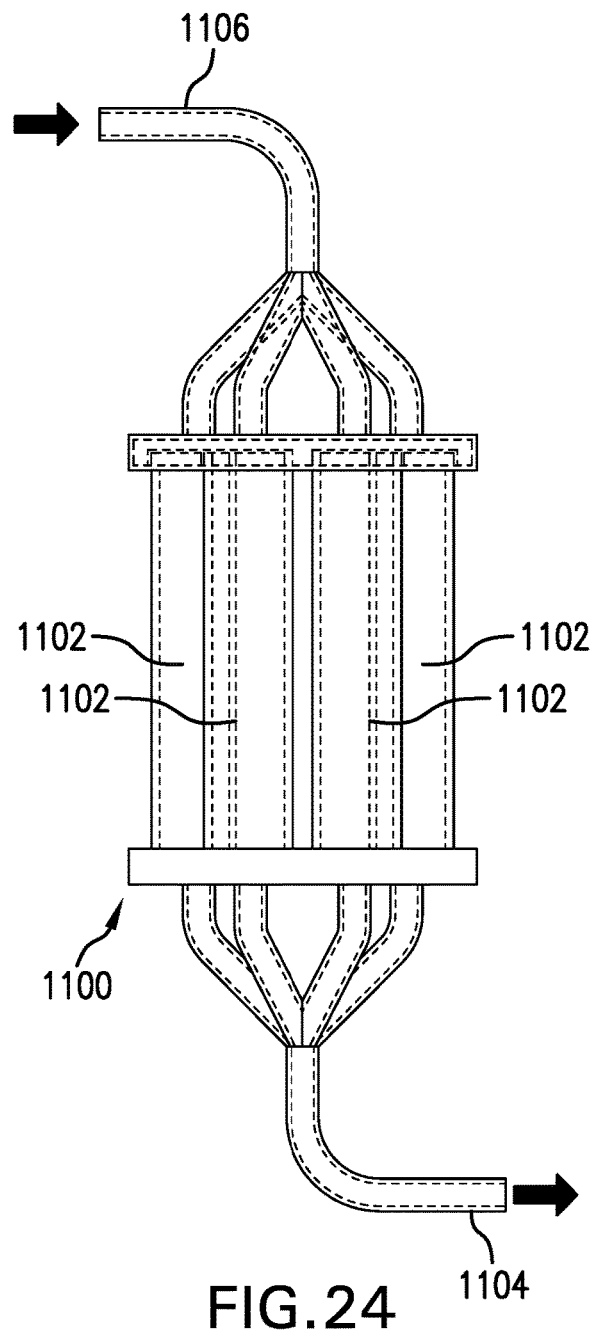
FIGS. 24-27 are schematics of a device with six nests arranged in parallel to discharge to a common outlet.
Figure 25:
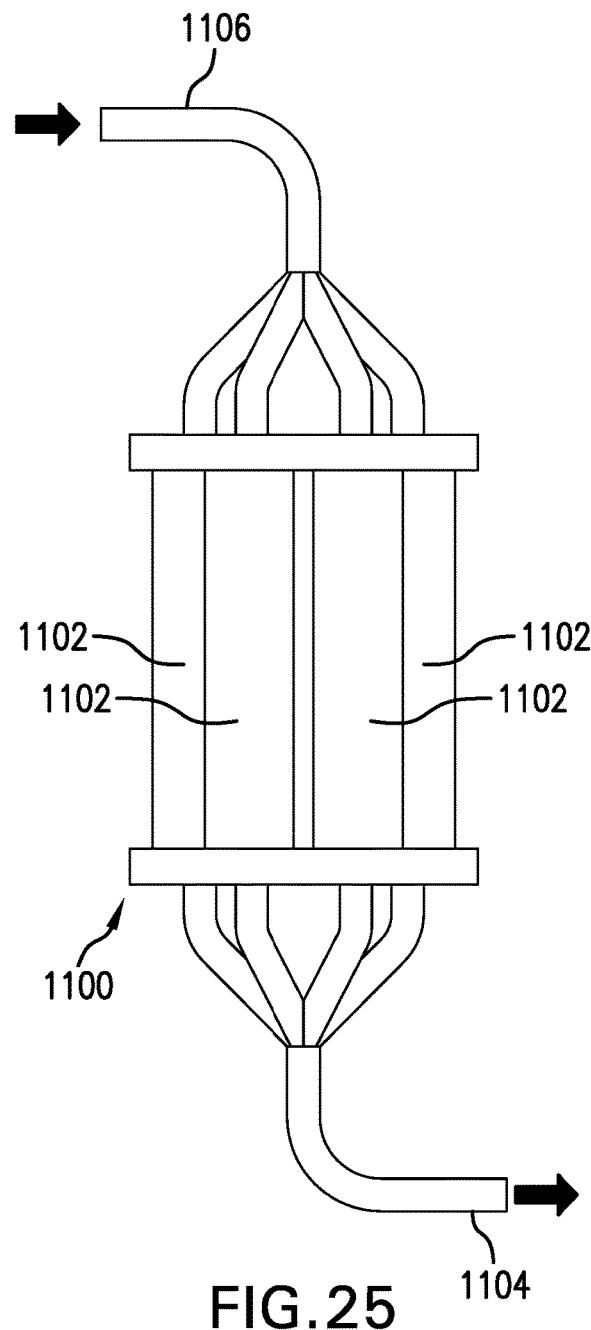
Figure 26:
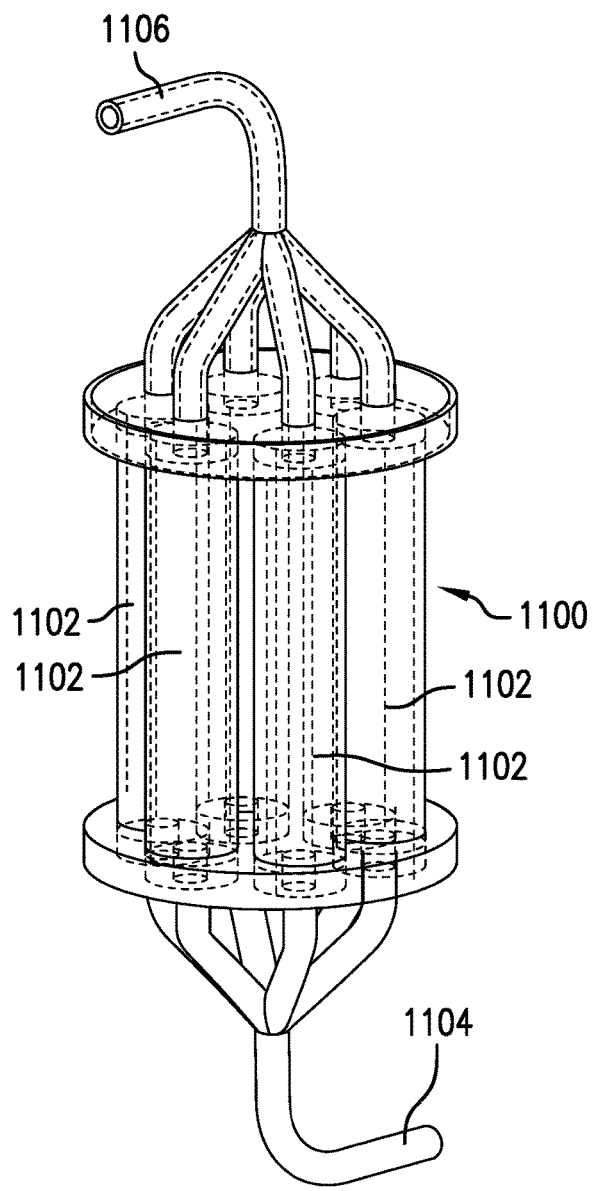
Figure 27:
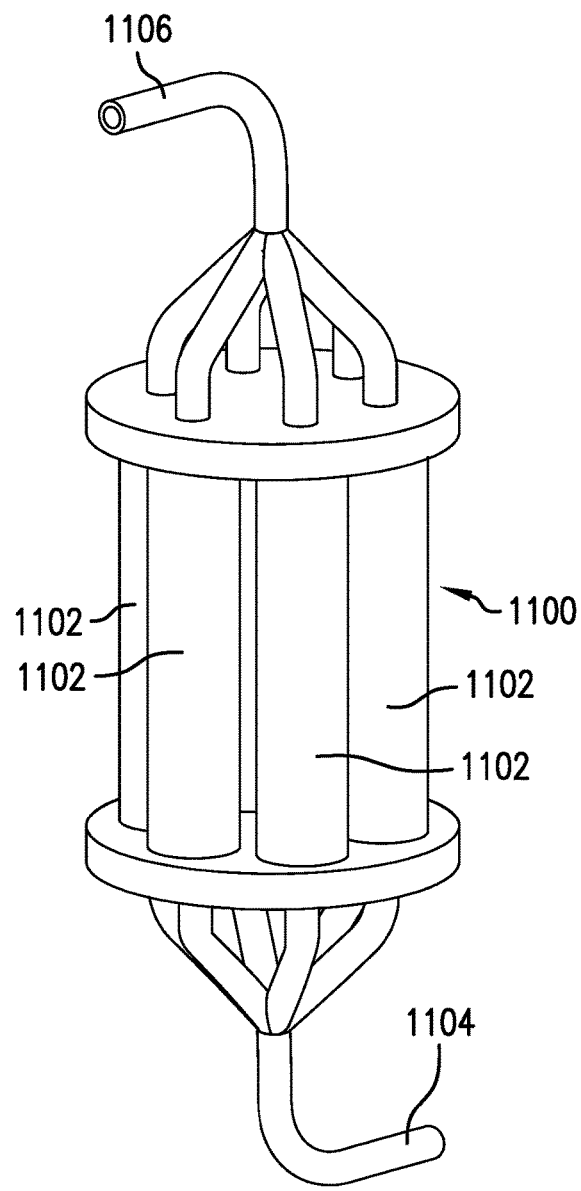
Figure 29:
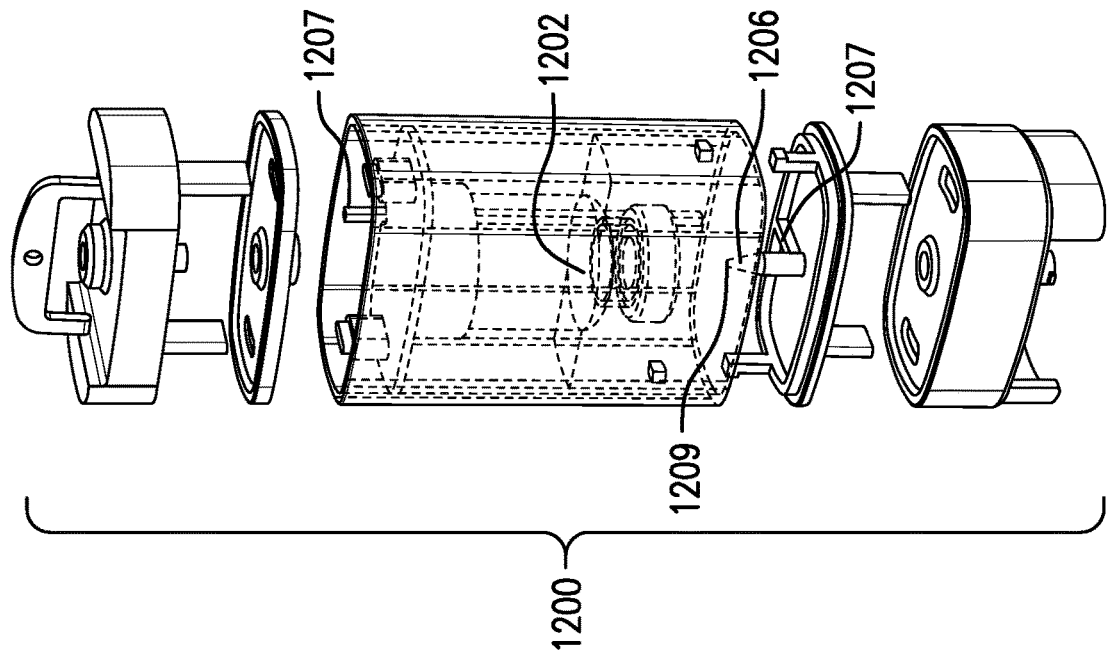
FIGS. 28-33 are schematics of a device utilizing stackable vials.
Figure 28:
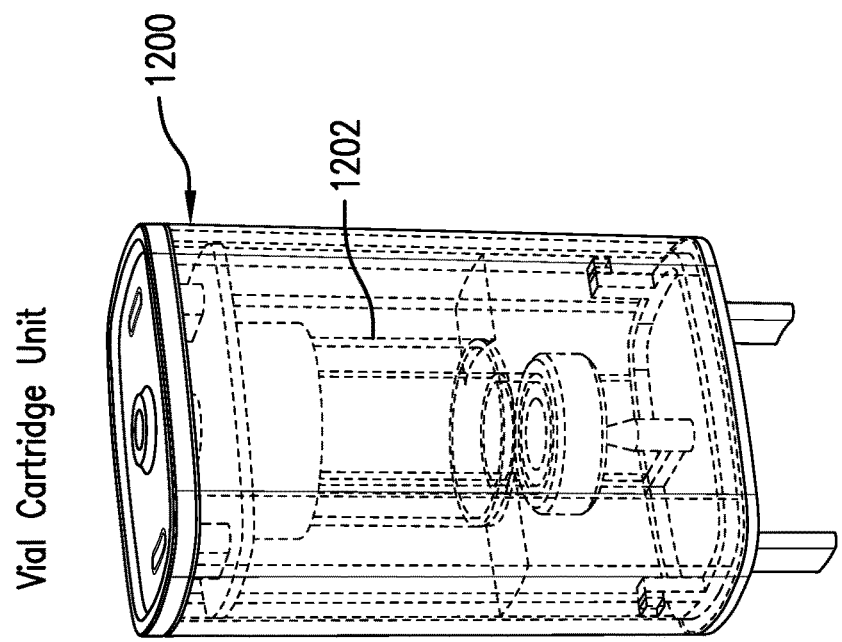
Figure 30:
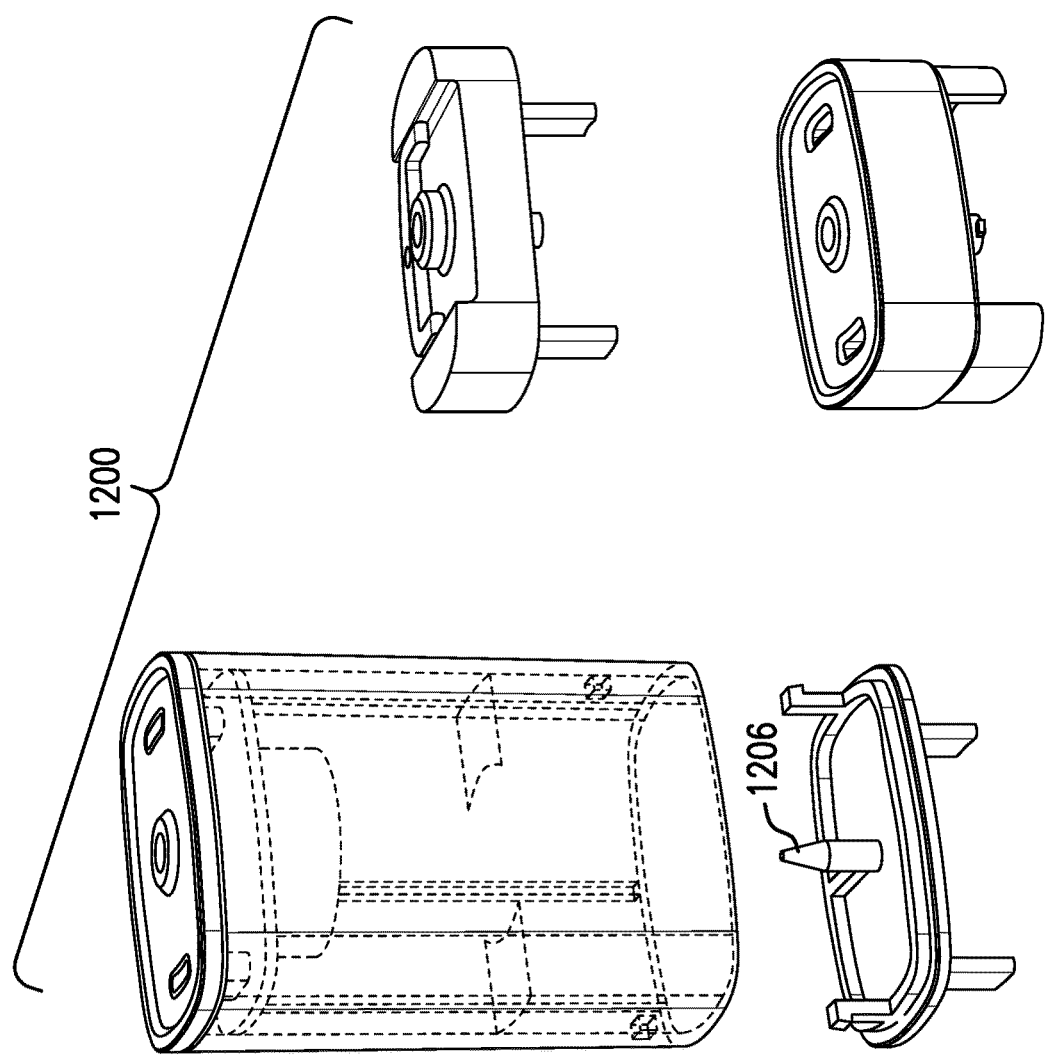
Figure 30:
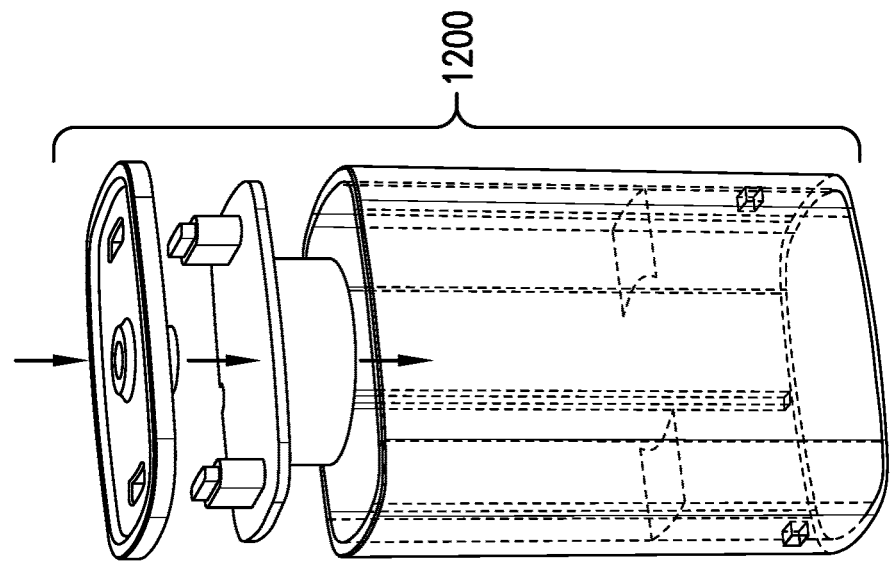

The drug preparation device 1000 shown in FIG. 23 is but one example of the present invention. It is a modular device, which mixes integral unit doses of liquid drug and transfers the resulting combination into a transfer container C, which then can be used with a separate delivery system such as an intravenous infusion bag, syringe/needle, auto-injector, wearable pump, etc. In embodiments the device 1000 comprises containers 1002 for holding drugs 1004 in liquid form, sterile connections between containers 1002 and a mechanism for the mixing and transfer of the drugs (e.g., pump 1006 in the form of an aspirating syringe). The containers 1002 are accessible from outside the device 1000. Said mechanism may comprise any of sterile tubing, valves etc. The pump 1006 is cycled manually by the user to generate a pressure difference for the mixing and transfer of the drugs 1004 and the resulting combination. The device 1000 includes a body 1008 defining a plurality of nests 1010 for accommodating the containers 1002. The nests 1010 are serially connected in the same manner as any of the embodiments herein to allow flow between the containers 1002 when mounted in the nests 1010. Several different arrangements of the connections of the nests 1010 are possible. The various components of the device 1000 can be manufactured within the supply chain and then final assembled at the point-of-care along with a standard transfer container C at a common outlet 1012 of the device 1000, such as an intravenous infusion bag prior to use. In embodiments the device 1000 may incorporate a micro-filtered vent 1014 for the equalization of pressure during mixing and delivery particularly to vent the flow path between the containers 1002. The device shown in FIG. 23 has positions for six containers 1002, although various quantities may be utilized. When connected in series between the vent 1014 and the pump 1006, then the nest connections may be like those shown schematically in FIG. 7a. If the strengths of the individual drugs are always the same and vacant positions are permitted then the compositions accessible from this device are those illustrated in FIGS. 7b-g.

The device 1000 may be internally arranged to include the components of any of the embodiments herein to allow the drugs 1004 of the containers 1002 to combine.

The drug preparation device 1100 shown in FIGS. 24-27 is but one example of the present invention. This arrangement allows for a plurality (e.g., six) nested containers 1102 to be arranged in parallel with a common outlet 1104. Diluent may be introduced via inlet 1106 in parallel to each vial with individual discharges mixing in the common outlet 1104.

The device 10 may be internally arranged to include the components of any of the embodiments herein, particularly to allow the drug components of the capsules 18 to combine with the liquid contents (diluent, drug) of the cartridge 14.

As will be appreciated by those skilled in the art, any number of the containers may be utilized with the subject invention consistent with the disclosure herein.

It is also noted that nests not intended for drug mixing may be left open and by-passed, e.g., with tubing. Alternatively, the non-used nests may be occupied by a container of diluent and/or water, saline, or other benign liquid.

As will be appreciated by those skilled in the art, the pumps disclosed herein may be configured to generate negative pressure to draw out the contents of the containers and urge same towards the common outlet, which may be on the discharge side of the pump.

Any of the devices herein may include one or more bodies (e.g., being modular, such as described with the devices 400, 500) with the various components being distributed between such bodies (or within a single body) in any working arrangement.

Figure 31:
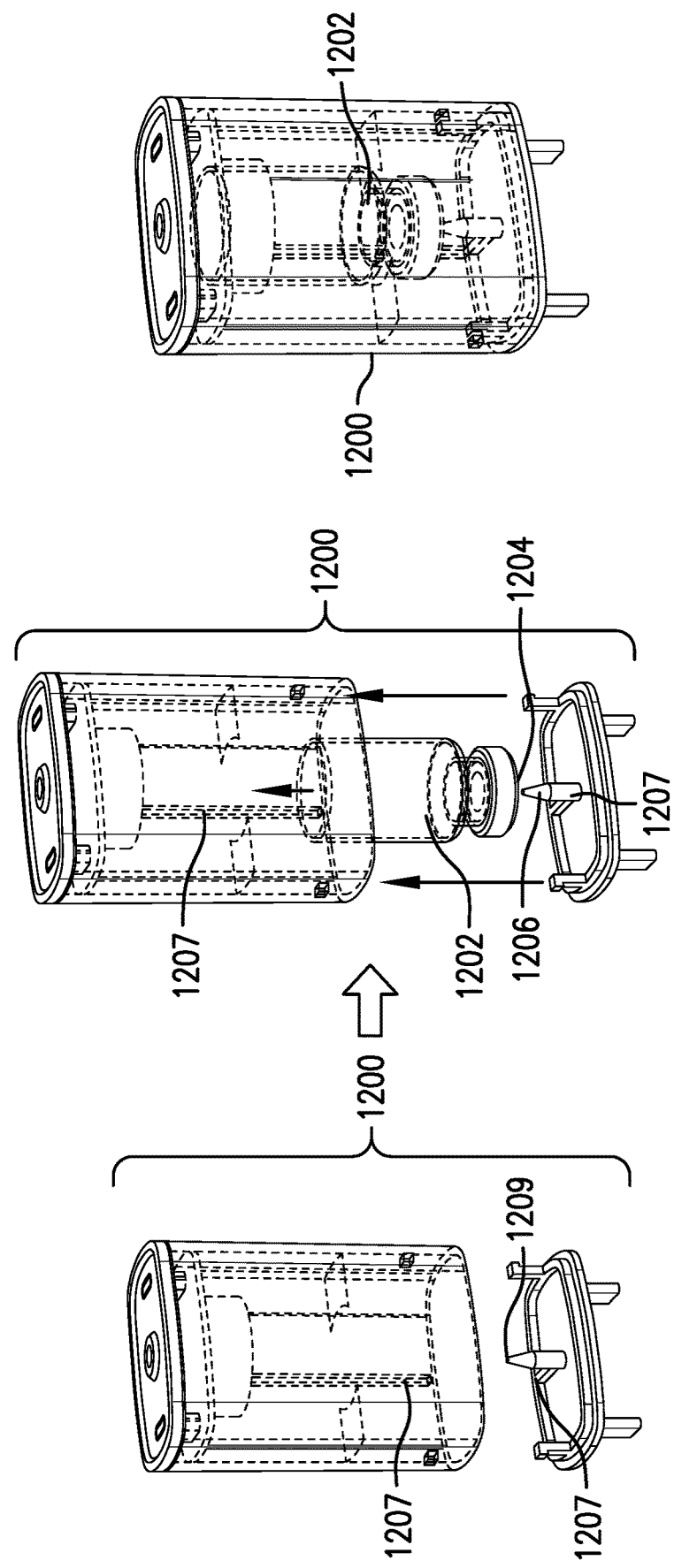
Figure 32:
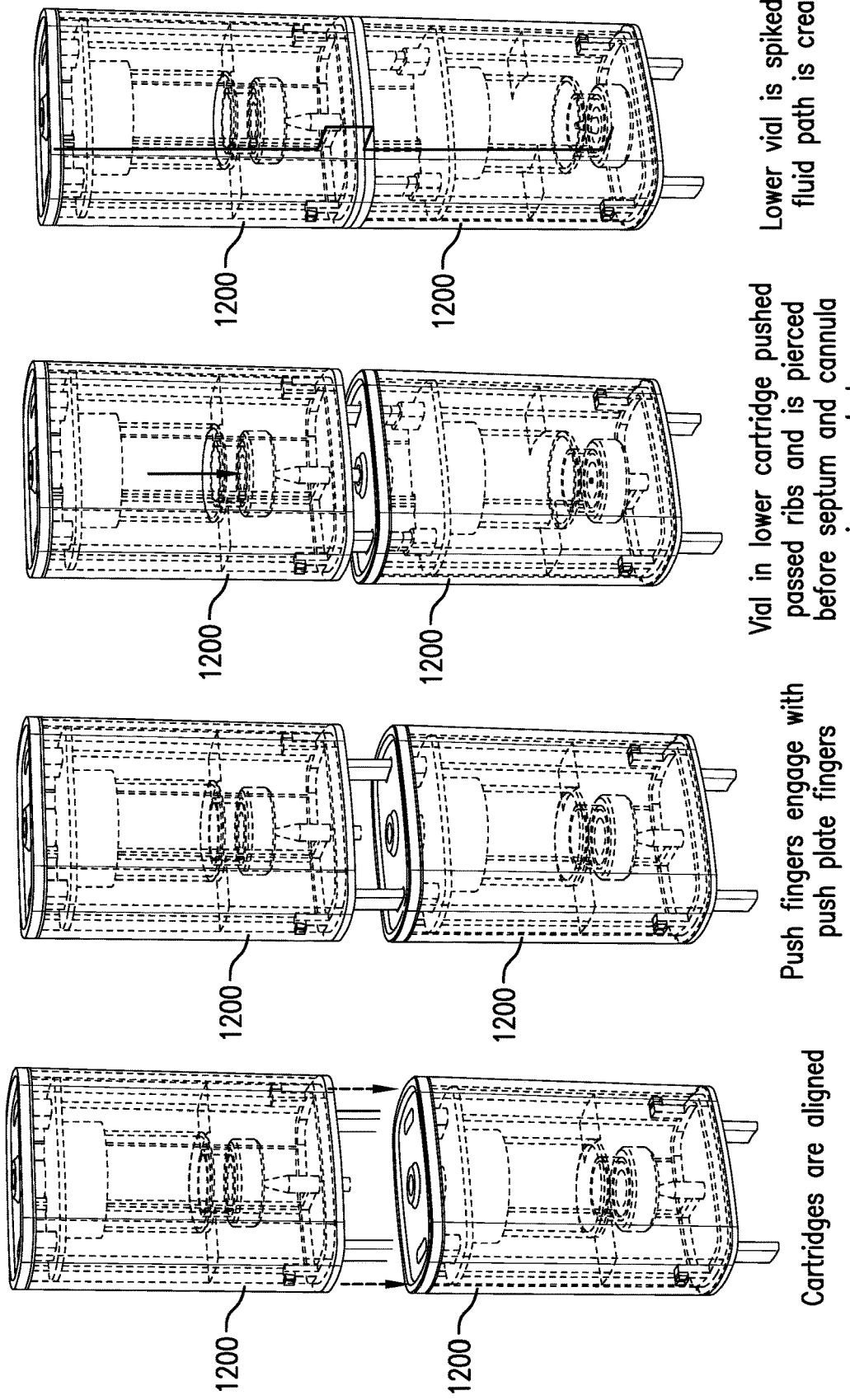
Figure 33:
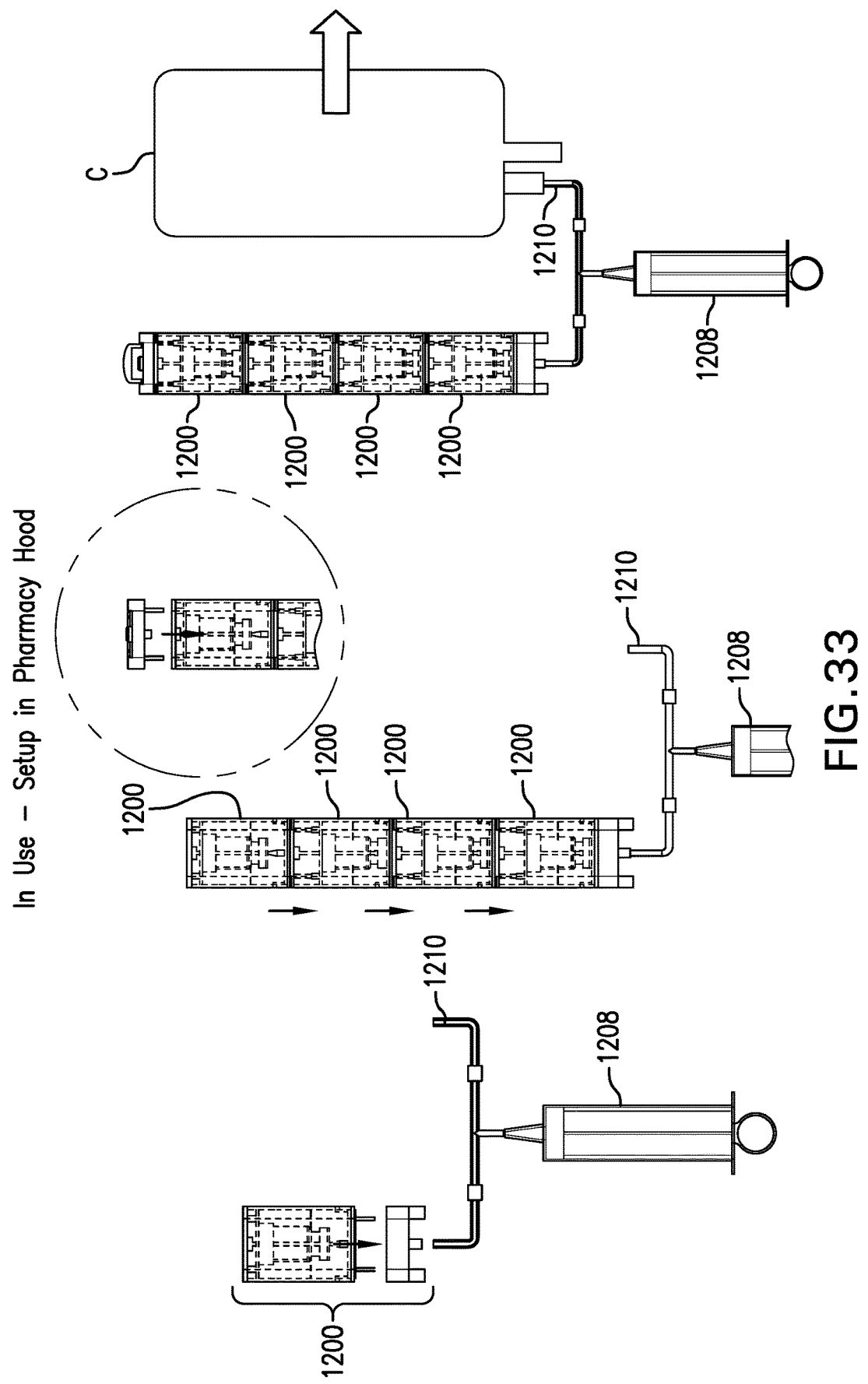

As shown in FIGS. 28-33, the containers (e.g., vials) may be also caused to couple, e.g., in a stack, as a device (or within a device) with connections in between to achieve combinations in accordance with the subject invention. Housings 1200 may be provided for each of the containers 1202 to facilitate coupling. A flow may be created between the containers 1202, with the housings 1200 coupled, using the same principles, as described here for in-series container arrangements, such as shown in FIGS. 7a, 15, 16, 17, 18. 19, 20, 21, and 22. The coupled housing 1200 may be used with any of the devices described herein to replace an in-series set of containers, so that the coupled housings 1200 may be used in combination with a pump 1208 (including aspirating syringe, such as shown in FIG. 33), common outlet 1210, electronic micro-controllers, power sources, diluent reservoirs, transfer containers C, and so forth. The containers 1202 may include pierceable septums 1204 which allow for access to contained contents by breach of a spike 1206 provided on each of the housings 1200. The spikes 1206 are connected by defined fluid paths 1207 to allow for container-to-container flow between the housings 1200. The fluid path 1207 is defined through the spikes 1206 by internal lumens therethrough which terminate at openings 1209. The containers 1202 are mountable in the housings 1200 (FIG. 31). The spikes 1206 may be spaced from the containers 1202 (FIG. 28), particularly the septums 1204, until ready to use, when the spikes 1206 may be urged to breach the septums 1204 to create fluid connections (FIG. 32). The housings 1200 may be made stackable to allow for rigid interconnections with the spikes 1206 accessing vial contents. Various combinations (type and quantity) of the containers 1202 may be used in a "stack" to provide for different drug combinations. The containers 1202 may be stackable dry powder cartridges, which may be coupled with a flow of diluent.

For any of the foregoing embodiments, the contents of the vials may be considered in determining nest or other location on a device. For example, a vial containing relatively large proteins may be located closer to a source of pressure used to generate flow between the vials. In addition, the reactivity between components may be taken into consideration in determining a mixing sequence, particularly where vials are arranged in series.

It shall be understood that the foregoing embodiments are examples of devices constructed according to the present invention and that they are in no way intended to limit the scope of the invention. In embodiments devices constructed in accordance with the present invention may comprise means to assist with the mixing and reconstitution of the drugs. Such means may include but are not limited to shear cells, agitation mechanisms, peristaltic mechanisms, static mixers, constrictions, jet nozzles etc.

In embodiments it may be advantageous for the purposes of complete mixing to reverse the direction of flow within the device, for example to provide shearing action in a shear cell. Mechanisms for the reversal of flow are well known to the person skilled in the art and may include but are not limited to valves, gears, stepper motors.

In embodiments the devices constructed according to the present invention and intended for body worn subcutaneous delivery may comprise means for the automated insertion of the delivery needle into and retraction from the patient.

Especially in situations where there exist incompatibilities between the drug formulations, which restrict their ex-vivo combination, in embodiments devices constructed according to the present invention may be provided with a plurality of needles for the subcutaneous delivery of the drugs individually to avoid ex-vivo combination.

In one embodiment, any of the combinatorial drug delivery devices disclosed herein is able to deliver two or more drugs for the benefit of the patient suffering from any of a wide range of diseases or conditions, e.g., cancer, autoimmune disorder, inflammatory disorder, cardiovascular disease or fibrotic disorder.

In one embodiment, one or more of the drugs of any of the combinatorial drug delivery devices disclosed herein is an immune checkpoint inhibitor. In certain embodiments, the immune checkpoint inhibitor is Programmed Death-1 ("PD-1") pathway inhibitor, a cytotoxic T-lymphocyte-associated antigen 4 ("CTLA-4") antagonist, a Lymphocyte Activation Gene-3 ("LAG3") antagonist, a CD80 antagonist, a CD86 antagonist, a T cell immunoglobulin and mucin domain ("Tim-3") antagonist, a T cell immunoreceptor with Ig and ITIM domains ("TIGIT") antagonist, a CD20 antagonist, a CD96 antagonist, a Indoleamine 2,3-dioxygenase ("IDO1") antagonist, a stimulator of interferon genes ("STING") antagonist, a GARP antagonist, a CD40 antagonist, Adenosine A2A receptor ("A2aR") antagonist, a CEACAM1 (CD66a) antagonist, a CEA antagonist, a CD47 antagonist, a Receptor Related Immunoglobulin Domain Containing Protein ("PVRIG") antagonist, a tryptophan 2,3-dioxygenase ("TDO") antagonist, a V-domain Ig suppressor of T cell activation ("VISTA") antagonist, or a Killer-cell Immunoglobulin-like Receptor ("KIR") antagonist.

In one embodiment, the PD-1 pathway inhibitor is an anti-PD-1 antibody or antigen binding fragment thereof. In certain embodiments, the anti-PD-1 antibody is pembrolizumab (KEYTRUDA; MK-3475), pidilizumab (CT-011), nivolumab (OPDIVO; BMS-936558), PDR001, MEDI0680 (AMP-514), TSR-042, REGN2810, JS001, AMP-224 (GSK-2661380), PF-06801591, BGB-A317, BI 754091, or SHR-1210.

In one embodiment, the PD-1 pathway inhibitor is an anti-PD-L1 antibody or antigen binding fragment thereof. In certain embodiments, the anti-PD-L1 antibody is atezolizumab (TECENTRIQ; RG7446; MPDL3280A; RO5541267), durvalumab (MEDI4736), BMS-936559, avelumab (bavencio), LY3300054, CX-072 (Proclaim-CX-072), FAZ053, KN035, or MDX-1105.

In one embodiment, the PD-1 pathway inhibitor is a small molecule drug. In certain embodiments, the PD-1 pathway inhibitor is CA-170. In another embodiment, the PD-1 pathway inhibitor is a cell based therapy. In one embodiment, the cell based therapy is a MiHA-loaded PD-L1/L2-silenced dendritic cell vaccine. In other embodiments, the cell based therapy is an anti-programmed cell death protein 1 antibody expressing pluripotent killer T lymphocyte, an autologous PD-1-targeted chimeric switch receptor-modified T lymphocyte, or a PD-1 knockout autologous T lymphocyte.

In one embodiment, the PD-1 pathway inhibitor is an anti-PD-L2 antibody or antigen binding fragment thereof. In another embodiment, the anti-PD-L2 antibody is rHIgM12B7.

In one embodiment, the PD-1 pathway inhibitor is a soluble PD-1 polypeptide. In certain embodiments, the soluble PD-1 polypeptide is a fusion polypeptide. In some embodiments, the soluble PD-1 polypeptide comprises a ligand binding fragment of the PD-1 extracellular domain. In other embodiments, the soluble PD-1 polypeptide comprises a ligand binding fragment of the PD-1 extracellular domain. In another embodiment, the soluble PD-1 polypeptide further comprises an Fc domain.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015. In one embodiment, any of the combinatorial drug delivery devices disclosed herein includes a CTLA-4 antagonist, e.g., ipilimumab (YERVOY), a PD-1 pathway inhibitor, e.g., nivolumab (OPDIVO) or pembrolizumab (KEYTRUDA).

In one embodiment, the immune checkpoint inhibitor is an antagonist of LAG3. In certain embodiments, the LAG3 antagonist is an anti-LAG3 antibody or antigen binding fragment thereof. In certain embodiments, the anti-LAG3 antibody is relatlimab (BMS-986016), MK-4280 (28G-10), REGN3767, GSK2831781, IMP731 (H5L7BW), BAP050, IMP-701 (LAG-5250), IMP321, TSR-033, LAG525, BI 754111, or FS-118. In one embodiment, any of the combinatorial drug delivery devices disclosed herein includes a LAG3 antagonist, e.g., relatlimab or MK-4280, and a PD-1 pathway inhibitor, e.g., nivolumab (OPDIVO) or pembrolizumab (KEYTRUDA). In one embodiment, any of the combinatorial drug delivery devices disclosed herein includes a LAG3 antagonist, e.g., relatlimab or MK-4280, and a CTLA-4 antagonist, e.g., ipilimumab (YERVOY). In one embodiment, any of the combinatorial drug delivery devices disclosed herein includes a LAG3 antagonist, e.g., relatlimab or MK-4280, a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the CTLA-4 antagonist is a soluble CTLA-4 polypeptide. In one embodiment, the soluble CTLA-4 polypeptide is abatacept (ORENCIA), belatacept (NULOJIX), RG2077, or RG-1046. In another embodiment, the CTLA-4 antagonist is a cell based therapy. In some embodiments, the CTLA-4 antagonist is an anti-CTLA4 mAb RNA/GITRL RNA-transfected autologous dendritic cell vaccine or an anti-CTLA-4 mAb RNA-transfected autologous dendritic cell vaccine.

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is an IDO1 antagonist. In another embodiment, the IDO1 antagonist is indoximod (NLG8189; 1-methyl-$_D$-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-dinucleotides; 2'3'-di-fluoro substituted mixed linkage 2',5'-3', 5' cyclic-di-nucleotides; 2'-fluoro substituted, bis-3',5' cyclic-di-nucleotides; 2',2"-diF-Rp,Rp,bis-3',5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In certain embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In certain embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cergutuzumab amunaleukin (RG7813, RO-6895882) or RG7802 (RO6958688).

In one embodiment, the immune checkpoint inhibitor is a CD47 antagonist. In some embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

In one embodiment, one or more of the drugs of any of the combinatorial drug delivery devices disclosed herein is an immune checkpoint enhancer or stimulator.

In one embodiment, the immune checkpoint enhancer or stimulator is a CD28 agonist, a 4-1BB agonist, an OX40 agonist, a CD27 agonist, a CD80 agonist, a CD86 agonist, a CD40 agonist, an ICOS agonist, a CD70 agonist, or a GITR agonist.

In one embodiment, the immune checkpoint enhancer or stimulator is an OX40 agonist. In certain embodiments, the OX40 agonist is an anti-OX40 antibody or antigen binding fragment thereof. In some embodiments, the anti-OX40 antibody is tavolixizumab (MEDI-0562), pogalizumab (MOXR0916, RG7888), GSK3174998, ATOR-1015, MEDI-6383, MEDI-6469, BMS 986178, PF-04518600, or RG7888 (MOXR0916). In another embodiment, the OX40 agonist is a cell based therapy. In certain embodiments, the OX40 agonist is a GINAKIT cell (iC9-GD2-CD28-OX40-expressing T lymphocytes).

In one embodiment, the immune checkpoint enhancer or stimulator is a CD40 agonist. In some embodiments, the CD40 agonist is an anti-CD40 antibody or antigen binding fragment thereof. In one embodiment, the anti-CD40 antibody is ADC-1013 (JNJ-64457107), RG7876 (RO-7009789), HuCD40-M2, APX005M (EPI-0050), or Chi Lob 7/4. In another embodiment, the CD40 agonist is a soluble CD40 ligand (CD40-L). In one embodiment, the soluble CD40 ligand is a fusion polypeptide. In certain embodiments, the soluble CD40 ligand is a trimeric CD40-L (AVREND®).

In one embodiment, the immune checkpoint enhancer or stimulator is a GITR agonist. In certain embodiments, the GITR agonist is an anti-GITR antibody or antigen binding fragment thereof. In one embodiment, the anti-GITR antibody is BMS-986156, TRX518, GWN323, INCAGN01876, or MEDI1873. In one embodiment, the GITR agonist is a soluble GITR ligand (GITRL). In some embodiments, the soluble GITR ligand is a fusion polypeptide. In another embodiment, the GITR agonist is a cell based therapy. In one embodiment, the cell based therapy is an anti-CTLA4 mAb RNA/GITRL RNA-transfected autologous dendritic cell vaccine or a GITRL RNA-transfected autologous dendritic cell vaccine.

In one embodiment, the immune checkpoint enhancer or stimulator a 4-1BB agonist. In some embodiments, the 4-1BB agonist is an anti-4-1BB antibody or antigen binding fragment thereof. In one embodiment, the anti-4-1BB antibody is urelumab or PF-05082566.

In one embodiment, the immune checkpoint enhancer or stimulator is a CD80 agonist or a CD86 agonist. In some embodiments, the CD80 agonist or the CD86 agonist is a soluble CD80 or CD86 ligand (CTLA-4). In certain embodiments, the soluble CD80 or CD86 ligand is a fusion polypeptide. In one embodiment, the CD80 or CD86 ligand is CTLA4-Ig (CTLA4-IgG4m, RG2077, or RG1046) or abatacept (ORENCIA, BMS-188667). In other embodiments, the CD80 agonist or the CD86 agonist is a cell based therapy. In one embodiment, the cell based therapy is MGN1601 (an allogeneic renal cell carcinoma vaccine).

In one embodiment, the immune checkpoint enhancer or stimulator is a CD28 agonist. In some embodiments, the CD28 agonist is an anti-CD28 antibody or antigen binding fragment thereof. In certain embodiments, the anti-CD28 antibody is TGN1412.

In one embodiment, the CD28 agonist is a cell based therapy. In certain embodiments, the cell based therapy is JCAR015 (anti-CD19-CD28-zeta modified CAR CD3+T lymphocyte); CD28CAR/CD137CAR-expressing T lymphocyte; allogeneic CD4+ memory Th1-like T cells/microparticle-bound anti-CD3/anti-CD28; anti-CD19/CD28/CD3zeta CAR gammaretroviral vector-transduced autologous T lymphocytes KTE-C19; anti-CEA IgCD28TCR-transduced autologous T lymphocytes; anti-EGFRvIII CAR-transduced allogeneic T lymphocytes; autologous CD123CAR-CD28-CD3zeta-EGFRt-expressing T lymphocytes; autologous CD171-specific CAR-CD28 zeta-4-1-BB-EGFRt-expressing T lymphocytes; autologous CD19CAR-CD28-CD3zeta-EGFRt-expressing Tcm-enriched T cells; autologous PD-1-targeted chimeric switch receptor-modified T lymphocytes (chimera with CD28); CD19CAR-CD28-CD3zeta-EGFRt-expressing Tcm-enriched T lymphocytes; CD19CAR-CD28-CD3zeta-EGFRt-expressing Tn/mem-enriched T lymphocytes; CD19CAR-CD28zeta-4-1BB-expressing allogeneic T lymphocytes; CD19CAR-CD3zeta-4-1BB-CD28-expressing autologous T lymphocytes; CD28CAR/CD137CAR-expressing T lymphocytes; CD3/CD28 costimulated vaccine-primed autologous T lymphocytes; or iC9-GD2-CD28-OX40-expressing T lymphocytes.

In one embodiment, the immune checkpoint enhancer or stimulator is a CD27 agonist. In certain embodiments, the CD27 agonist is an anti-CD27 antibody or antigen binding fragment thereof. In one embodiment, the anti-CD27 antibody is varlilumab (CDX-1127).

In one embodiment, the immune checkpoint enhancer or stimulator is a CD70 agonist. In some embodiments, the CD70 agonist is an anti-CD70 antibody or antigen binding fragment thereof. In one embodiment, the anti-CD70 antibody is ARGX-110.

In one embodiment, the immune checkpoint enhancer or stimulator is an ICOS agonist. In certain embodiments, the ICOS agonist is an anti-ICOS antibody or antigen binding fragment thereof. In some embodiments, the anti-ICOS antibody is BMS986226, MEDI-570, GSK3359609, or JTX-2011. In other embodiments, the ICOS agonist is a soluble ICOS ligand. In some embodiments, the soluble ICOS ligand is a fusion polypeptide. In one embodiment, the soluble ICOS ligand is AMG 750.

In one embodiment, one or more of the drugs of any of the combinatorial drug delivery devices disclosed herein is an anti-CD73 antibody or antigen binding fragment thereof. In certain embodiments, the anti-CD73 antibody is MEDI9447.

In one embodiment, one or more of the drugs of any of the combinatorial drug delivery devices disclosed herein is a TLR9 agonist. In one embodiment, the TLR9 agonist is agatolimod sodium.

In one embodiment, one or more of the drugs of any of the combinatorial drug delivery devices disclosed herein is a cytokine. In certain embodiments, the cytokine is a chemokine, an interferon, an interleukin, lymphokine, or a member of the tumor necrosis factor family. In some embodiments, the cytokine is IL-2, IL-15, or interferon-gamma.

In one embodiment, one or more of the drugs of any of the combinatorial drug delivery devices disclosed herein is a TGF-β antagonist. In some embodiments, the TGF-β antagonist is fresolimumab (GC-1008); NIS793; IMC-TR1 (LY3022859); ISTH0036; trabedersen (AP 12009); recombinant transforming growth factor-beta-2; autologous HPV-16/18 E6/E7-specific TGF-beta-resistant T lymphocytes; or TGF-beta-resistant LMP-specific cytotoxic T-lymphocytes.

In one embodiment, one or more of the drugs of any of the combinatorial drug delivery devices disclosed herein is an iNOS antagonist. In some embodiments, the iNOS antagonist is N-Acetyle-cysteine (NAC), aminoguanidine, L-nitroarginine methyl ester, or S,S-1,4-phenylene-bis(1,2-ethanediyl)bis-isothiourea).

In one embodiment, one or more of the drugs of any of the combinatorial drug delivery devices disclosed herein is a SHP-1 antagonist.

In one embodiment, one or more of the drugs of any of the combinatorial drug delivery devices disclosed herein is a colony stimulating factor 1 receptor ("CSF1R") antagonist. In certain embodiments, the CSF1R antagonist is an anti-CSF1R antibody or antigen binding fragment thereof. In some embodiments, the anti-CSF1R antibody is emactuzumab.

In one embodiment, one or more of the drugs of any of the combinatorial drug delivery devices disclosed herein is an agonist of a TNF family member. In some embodiments, the agonist of the TNF family member is ATOR 1016, ABBV-621, or Adalimumab.

In one embodiment, one or more of the drugs of any of the combinatorial drug delivery devices disclosed herein is aldesleukin, bempegaldesleukin, tocilizumab, or MEDI5083. In one embodiment, any of the combinatorial drug delivery devices disclosed herein includes bempegaldesleukin and a PD-1 pathway inhibitor, e.g., nivolumab (OPDIVO) or pembrolizumab (KEYTRUDA). In one embodiment, any of the combinatorial drug delivery devices disclosed herein includes bempegaldesleukin and a LAG3 antagonist, e.g., relatlimab or MK-4280. In one embodiment, any of the combinatorial drug delivery devices disclosed herein includes bempegaldesleukin, a PD-1 pathway inhibitor, e.g., nivolumab (OPDIVO) or pembrolizumab (KEYTRUDA), and a LAG3 antagonist, e.g., relatlimab or MK-4280. In one embodiment, any of the combinatorial drug delivery devices disclosed herein includes bempegaldesleukin and a CTLA-4 antagonist, e.g., ipilimumab (YERVOY).

In one embodiment, one or more of the drugs of any of the combinatorial drug delivery devices disclosed herein is a CD160 (NK1) agonist. In certain embodiments, the CD160 (NK1) agonist is an anti-CD160 antibody or antigen binding fragment thereof. In one embodiment, the anti-CD160 antibody is BY55.

What is claimed is:
1. A method, utilizing a body-wearable combinatorial drug delivery device, of delivering drug to a patient based on a predetermined selection of drug components, the method comprising:
providing a wearable device having an adhesive patch, for adhering to the skin of the patient, or a mounting belt, for supporting the device on the body of the patient, the wearable device including containers coupled to a common outlet, the common outlet being in communication with each of the coupled containers through a common flow path so that the drug components may be extracted from the coupled containers and dispensed through the common outlet;
securing the wearable device to the patient using the adhesive patch or the mounting belt; and,
applying negative pressure to the common outlet by a pump, externally of the coupled containers, to extract the drug components from the containers and urge the drug components towards the common outlet for delivery of the drug components to the patient, wherein, the pump, the coupled containers, and at least a portion of the common outlet are fully housed within the wearable device.

2. A method as in claim 1, wherein the coupled containers are coupled to the common outlet in parallel.

3. A method as in claim 1, wherein the coupled containers are coupled to the common outlet in series.

4. A method as in claim 1, wherein the coupled containers are indirectly coupled to a support structure.

5. A method as in claim 1, wherein the coupled containers are coupled to one another.

6. A method as in claim 1, wherein the containers are formed to accommodate different volumes of the drug components.

7. A method as in claim 1, wherein the common flow path is defined through at least a portion of the containers.

8. A method as in claim 7, wherein the common flow path is vented.

9. A method as in claim 1, wherein the coupled containers are coupled in a manifold arrangement with the common flow path which leads to the common outlet.

10. A method as in claim 9, wherein the common flow path is vented.

11. A method as in claim 1, wherein the common outlet is in communication with a cannula formed for injection.

12. A method as in claim 1, wherein at least one of the drug components is in powder form.

13. A method as in claim 1, wherein at least one of the drug components is in liquid form.

14. A method as in claim 1, wherein the containers may be in the form of one or more of a vial, cartridge, and capsule.

15. A method as in claim 1, wherein at least one of the containers is collapsible in response to the drug component being extracted therefrom.

16. A method as in claim 1, further comprising introducing a liquid into the coupled containers after the coupled containers are coupled to the common outlet and prior to applying the negative pressure to extract the drug components from the coupled containers.

17. A method as in claim 16, wherein the liquid is a diluent.

18. A method as in claim 16, wherein the liquid includes one or more drug components.

19. A method as in claim 16, wherein the liquid is introduced into the coupled containers under force of positive pressure.

20. A method as in claim 16, wherein the pump is bi-directional, and, wherein the bi-directional pump introduces the liquid into the coupled containers and applies the negative pressure to extract the drug components from the coupled containers.

21. A method as in claim 1, wherein a mixing chamber is located between the coupled containers and the common outlet with the drug components being urged towards the common outlet through the mixing chamber.

22. A method as in claim 1, further comprising mounting the containers into housings.

23. A method as in claim 1, wherein the wearable device further houses a microcontroller and a power source.

* * * * *